United States Patent
Kumar et al.

(10) Patent No.: US 10,988,444 B2
(45) Date of Patent: Apr. 27, 2021

(54) ANTIMICROBIAL COMPOUNDS

(71) Applicant: NEWSOUTH INNOVATIONS PTY LIMITED, Sydney (AU)

(72) Inventors: Naresh Kumar, Maroubra (AU); Mark Duncan Perry Willcox, Balmain (AU); Shashidhar Nizalapur, Liverpool (AU); David Ste Black, Kingsford (AU); Tsz Tin Yu, Carlingford (AU); Rajesh Kuppusamy, Kingsford (AU)

(73) Assignee: NEWSOUTH INNOVATIONS PTY LIMITED, Sydney (AU)

( * ) Notice: Subject to any disclaimer, the term of this patent is extended or adjusted under 35 U.S.C. 154(b) by 0 days.

(21) Appl. No.: 16/347,314

(22) PCT Filed: Nov. 3, 2017

(86) PCT No.: PCT/AU2017/051214
§ 371 (c)(1),
(2) Date: May 3, 2019

(87) PCT Pub. No.: WO2018/081869
PCT Pub. Date: May 11, 2018

(65) Prior Publication Data
US 2019/0256466 A1 Aug. 22, 2019

(30) Foreign Application Priority Data
Nov. 4, 2016 (AU) .................. 2016904509

(51) Int. Cl.
| | | |
|---|---|---|
| *C07D 209/20* | (2006.01) | |
| *C07C 237/22* | (2006.01) | |
| *A61P 31/04* | (2006.01) | |
| *C07C 311/08* | (2006.01) | |
| *A01N 37/46* | (2006.01) | |
| *C07C 279/14* | (2006.01) | |
| *A01N 43/38* | (2006.01) | |
| *C07K 5/02* | (2006.01) | |
| *A01N 47/44* | (2006.01) | |
| *A61K 9/00* | (2006.01) | |

(52) U.S. Cl.
CPC .......... *C07D 209/20* (2013.01); *A01N 37/46* (2013.01); *A01N 43/38* (2013.01); *A61P 31/04* (2018.01); *C07C 237/22* (2013.01); *C07C 279/14* (2013.01); *C07C 311/08* (2013.01); *C07K 5/0202* (2013.01); *A01N 47/44* (2013.01); *A61K 9/0019* (2013.01); *A61K 9/0031* (2013.01); *A61K 9/0053* (2013.01)

(58) Field of Classification Search
CPC .................. C07D 209/20; C07C 237/22
See application file for complete search history.

(56) References Cited

FOREIGN PATENT DOCUMENTS

WO 2014/190096 A1 11/2014

OTHER PUBLICATIONS

Catto, et al. Document No. 98:119156, retrieved from STN, 1983.*
Staph Infection [online] {retrieved on Apr. 10, 2008 from the Internet} {URL: http://www.medicinenet.com/script/main/art.asp?articlekey=1991&pf=3&page2}.*
Pseudomonas [online] {retrieved on Apr. 11, 2008 from the Internet} {URL: http://www.merck.com/m mhe/sect 17/chl 90/ch 1900.html#secl 7-ch 1900-262}.*
Salmonellosis [online] [retrieved on Feb. 27, 2009] and retrieved from URL; http://www.cdc.gov/nczved/dfbmed/disease_listing/salmonellosis_gi.html#4.*
International Search Report dated Dec. 14, 2017, in corresponding PCT/AU2017/051214.
Cranfield, Charles G.; Cornell, Bruce A.; Grage, Stephan L.; Duckworth, P.; Came, S.; Ulrich, Anne S.; Martinac, B. Biophys. J. 2014, 106, 182.
Cranfield, C.; Carne, S.; Martinac, B.; Cornell, B. In Methods in Membrane Lipids; Owen, D. M., Ed.; Springer New York: 2015; vol. 1232, p. 45.
Cranfield, C. G.; Bettler, T.; Cornell, B. Langmuir 2015, 31 (1), 292-298.
Cranfield, C. G.; Berry, T.; Holt, S. A.; Hossain, K. R.; Le Brun, A. P.; Came, S.; Al Khamici, H.; Coster, H.; Valenzuela, S. M.; Cornell, B. Langmuir 2016, 32 (41), 10725-10734.
Ge, Y.; MacDonald, D. L.; Holroyd, K. J.; Thornsberry, C.; Wexler, H.; Zasloff, M. Antimicrob. Agents Chemother. 1999, 43 (4), 782-788.
K. Murzyn, T. Róg and M. Pasenkiewicz-Gierula, Biophys. J., 2005, 88, 1091-1103.
Nizalapur, S.; Ho, K. K.; Kimyon, Ö.; Yee, E.; Berry, T.; Manefield, M.; Cranfield, C. G.; Willcox, M.; Black, D. S.; Kumar, N. Org. Biomol. Chem. 2016, 14, 3623.
O'Brien, J.; Wilson, I.; Orton, T.; Pognan, F. Eur. J. Biochem. 2000, 267 (17), 5421-5426.

(Continued)

*Primary Examiner* — Shawquia Jackson
(74) *Attorney, Agent, or Firm* — Ajay A. Jagtiani; Miles & Stockbridge P.C.

(57) ABSTRACT

The present application relates to compounds of Formula (I) and salts thereof. The compounds of Formula (I) have antibacterial and anti-biofilm activities. The present application also relates to compositions comprising the compounds of Formula (I) or salts thereof, methods of treating or preventing bacterial infections using the compounds of Formula (I) or salts thereof, and methods of inhibiting biofilm formation using the compounds of Formula (I) or salts thereof.

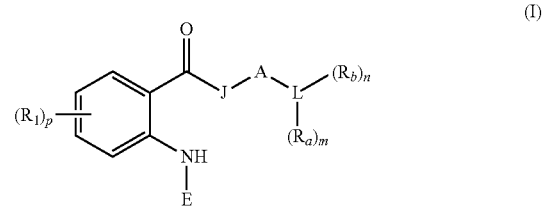

23 Claims, 5 Drawing Sheets

(56) References Cited

OTHER PUBLICATIONS

G. A. O'Toole, J Vis Exp, 2011, (47), pii: 2437, DOI: 10.3791/2437, 2437.
Pasquier, E.; Ciccolini, J.; Carre, M.; Giacometti, S.; Fanciullino, R.; Pouchy, C.; Montero, M.-P.; Serdjebi, C.; Kavallaris, M.; André, N. Oncotarget 2011, 2, 797.
Turner, Y. Cho, N.-N. Dinh, A. J. Waring and R. I. Lehrer, Antimicrob. Agents Chemother., 1998, 42, 2206-2214.
Wales, S. M.; Hammer, K. A.; King, A. M.; Tague, A. J.; Lyras, D.; Riley, T. V.; Keller, P. A.; Pyne, S. G. Org. Biomol. Chem. 2015, 13, 5743.
Wiegand, I.; Hilpert, K.; Hancock, R. E. W. Nat. Protocols 2008, 3 (2), 163-175.
Catto, A. et al, "Synthesis and antisecretory and antiulcerogenic activity of N-(2-acylaminophenyl)glyoxalyl-N'-acylhydrazines and N-(2-benzoylaminophenyl)glyocalylamides", Farmaco, Edizione Scientifica, 1983, vol. 38, No. 1, pp. 45-56 (Cited as D2 in ISR).
Nizalapur, S. et al, "Design, synthesis and evaluation of N-arylglyoxamide derivatives as structurally novel bacterial quorum sensing inhibitors", Organic & Biomolecular Chemistry, 2016, vol. 14, No. 2, pp. 680-693.
Nizalapur, S. et al, "Amphipathic guanidine-embedded glyoxamide-based peptidomimetics as novel antibacterial agents and biofilm disruptors", Organic & Biomolecular Chemistry, 2017, vol. 15, No. 9, pp. 2033-2051.
International Search Report for International Application No. PCT/AU2017/051214 dated Dec. 14, 2017.
Written Opinion for International Application No. PCT/AU2017/051214 dated Dec. 14, 2017.

\* cited by examiner

ANTIMICROBIAL COMPOUNDS

FIELD OF THE INVENTION

The present invention relates to antimicrobial compounds which show antibacterial and anti-biofilm activities. The present invention also relates to compositions comprising the compounds, methods of treating or preventing bacterial infections using the compounds, and methods of inhibiting biofilm formation using the compounds.

BACKGROUND

Antimicrobial resistance is becoming increasingly prevalent, with various Gram-positive and Gram-negative bacteria being resistant to many current antibiotics. This is due to the fact that existing antibiotics generally inhibit bacterial cellular processes that are essential for microbial survival, thus stimulating bacterial evolution by creating a selective pressure for drug-resistant mutations. It has been estimated by the Centers for Disease Control and Prevention (CDC) that drug-resistant bacteria cause 23,000 deaths and 2 million illnesses annually in the United States. The rapid global increase in the number of multidrug resistant strains, combined with the slow development of new antibiotics, presents a challenge for medicinal chemists to develop effective antibacterial therapies. Recent successful approaches have involved the structural modification of existing drugs such as antifungal azoles, antibacterial ß-lactams and quinolones. However, this strategy merely delays the development of bacterial resistance.

Biofilm formation is one of the ways bacteria can develop antibiotic resistance. Biofilms are a large network of bacteria protected by a self-produced matrix of exopolymeric substances, including polysaccharides, proteins and extracellular DNA. Bacteria within these networks are 10-1000 times more resistant to antibiotics than planktonic cells. In addition, the formation of biofilms contributes to 60-80% of chronic infections, such as cystic fibrosis and endocarditis. Biofilms are often formed on medical implants, such as catheters, artificial hips and contact lenses. In the US alone, 17 million new biofilm infections occur every year, which leads to 550,000 fatalities annually. In this context, it is increasingly important to develop novel antimicrobial drugs with different mechanisms of action in order to supplement or assist existing antimicrobial drugs, thereby reducing the rate of development of antibacterial resistance.

Biofilms provide an environment in which the microorganisms are protected from starvation, desiccation and the action of antibiotics. As a consequence, once established, biofilms are very difficult to remove. This can be problematic, particularly when biofilms are associated with the surface of a medical device.

For example, medical device related infections have emerged as an increasingly significant problem. These infections, if not prevented or treated, can lead to significant morbidity and mortality. Unfortunately, while alleviating one problem, a medical device implanted in a patient also provides a surface to which bacteria may attach and proliferate, leading to the formation of biofilm communities, which are exceedingly difficult to extinguish once they are established.

Current treatments and preventative measures rely on the use of antibiotics, quaternary ammonium coatings or antimicrobial compounds such as silver being released from the surface of medical devices. However, concerns about the development of bacterial resistance towards these antibiotics and cytotoxicity of silver and quaternary ammonium compounds limit the application of these techniques.

Natural host-defensive antimicrobial peptides (AMPs) and their mimics are drawing increasing focus as potential alternatives to classical antibiotics. Unlike regular antibiotics, AMPs act by disrupting membranes of the bacteria, which makes it difficult for the bacteria to develop resistance to AMPs. However, AMPs have several intrinsic limitations, namely degradation by proteases or peptidases, in vivo toxicity, non-selective action and high manufacturing costs.

Hence, there is a significant need for the development of novel antimicrobial compounds. It would be desirable to provide novel antimicrobial compounds which can disrupt bacterial biofilms.

SUMMARY OF THE INVENTION

In a first aspect, the present invention provides a compound of Formula (I):

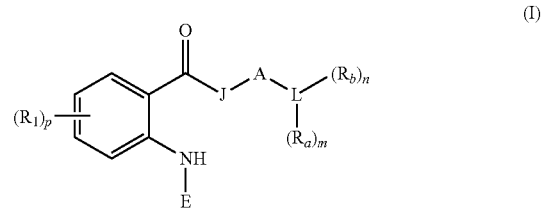

wherein:
J is

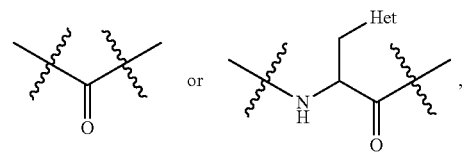

wherein Het is substituted or unsubstituted heteroaryl;

A is —NH—, —O— or —S—;

L is a saturated or unsaturated hydrocarbyl group having 1 to 12 carbon atoms, or L is —$(CH_2-CH_2-O)_r$— wherein r is 2, 3 or 4;

E is a hydrophobic group selected from —C(=O)$R_e$ or —$SO_2R_e$, wherein $R_e$ is $C_{6-18}$alkyl, $C_{6-18}$alkenyl, $C_{6-18}$alkynyl, aryl or heteroaryl, and wherein $R_e$ may optionally be substituted;

$R_a$ is independently selected from a substituted or unsubstituted amino group, a guanidine (—NH—C(=NH)(NH$_2$)) group, a CH$_3$-substituted guanidine (—[NCH$_3$—C(=NH)(NH$_2$)]) group, a substituted or unsubstituted ammonium group, a guanidinium (—[NH—C(=NH)(NH$_3$)]$^+$) group, or a CH$_3$-substituted guanidinium (—[NCH$_3$—C(=NH)(NH$_3$)]$^+$) group;

m is 1, 2 or 3;

$R_b$, when present, is independently selected from: a substituted or unsubstituted amino group, a guanidine (—NH—C(=NH)(NH$_2$)) group, a CH$_3$-substituted guanidine (—[NCH$_3$—C(=NH)(NH$_2$)]) group, a substituted or unsubstituted ammonium group, a guanidinium (—[NH—C(=NH)(NH$_3$)]$^+$) group, a CH$_3$-substituted guanidinium (—[NCH$_3$—C(=NH)(NH$_3$)]$^+$) group, a $R_e$-substituted or unsubstituted triazolyl group, —CONHR$_c$, or —COOR$_c$, wherein $R_c$ is H, a straight or branched $C_{1-12}$alkyl group, substituted or unsubstituted aryl, or substituted or unsubstituted heteroaryl, or $R_e$ is -L-$(R_a)_m$, wherein L, $R_a$ and m are as defined above and wherein L may optionally be substituted with —CONHR$_d$ or —COOR$_d$, wherein $R_d$ is a straight or branched $C_{1-12}$alkyl group;

n is 0, 1, 2 or 3;

$R_1$, when present, is independently selected from Br, Cl, F, —$C_{1-3}$alkyl, —$C_{1-3}$alkoxy, substituted or unsubstituted aryl, substituted or unsubstituted heteroaryl, —$SO_3H$, —$SO_3Na$, —$SO_2(C_{1-3}$alkyl), —$SO_2(OC_{1-3}$alkyl) or —$SO_2(N(C_{1-3}$alkyl)($C_{1-3}$alkyl)); and p is 0, 1, 2, 3 or 4;

or a salt thereof.

The compounds of Formula (I) have antibacterial activity. The compounds of Formula (I) have a range of applications including dermal applications (e.g. in wound care and in combatting skin infections), therapeutic applications (e.g. antibiotics); attachment to a surface (including surfaces of implantable devices in the human or animal body); and in industrial applications where biofilm is a problem (e.g. cleaning agents).

In a second aspect, the present invention provides a composition comprising a compound of Formula (I), or a salt thereof, and a carrier.

In a third aspect, the present invention provides a pharmaceutical composition comprising a compound of Formula (I), or a pharmaceutically acceptable salt thereof, and a pharmaceutically acceptable carrier, adjuvant or diluent.

In a fourth aspect, the present invention provides a method of treating or preventing a bacterial infection in a subject, the method comprising administering to the subject an effective amount of a compound of Formula (I) or a pharmaceutically acceptable salt thereof.

In a fifth aspect, the present invention provides a method of killing bacteria, or inhibiting the proliferation of bacteria, the method comprising contacting the bacteria with an effective amount of a compound of Formula (I) or a salt thereof.

In a sixth aspect, the present invention provides a method of treating a surface to prevent, reduce or inhibit biofilm formation on the surface, the method comprising applying to the surface an effective amount of a compound of Formula (I) or a salt thereof.

In a seventh aspect, the present invention provides a method of treating a surface to prevent, reduce or inhibit biofilm formation on the surface, the method comprising contacting the surface with an effective amount of a compound of Formula (I) or a salt thereof.

In an eighth aspect, the present invention provides a method of preventing, reducing or inhibiting biofilm formation on a surface, the method comprising applying to the surface an effective amount of a compound of Formula (I) or a salt thereof.

In a ninth aspect, the present invention provides a method of preventing, reducing or inhibiting biofilm formation on a surface, the method comprising contacting the surface with an effective amount of a compound of Formula (I) or a salt thereof.

In a tenth aspect, the present invention provides a method of preventing, reducing or inhibiting biofilm formation on a surface, the method comprising exposing a biofilm, or a microorganism capable of forming a biofilm, to a compound of Formula (I) or a salt thereof.

In an eleventh aspect, the present invention provides a compound of Formula (I), or a pharmaceutically acceptable salt thereof, for treating or preventing a bacterial infection in a subject.

In a twelfth aspect, the present invention provides the use of a compound of Formula (I), or a pharmaceutically acceptable salt thereof, in the manufacture of a medicament for treating or preventing a bacterial infection in a subject.

BRIEF DESCRIPTION OF THE FIGURES

Embodiments of the present invention will be further described, by way of example only, with reference to the accompanying drawings, in which.

DETAILED DESCRIPTION OF EMBODIMENTS OF THE INVENTION

Figure 1:
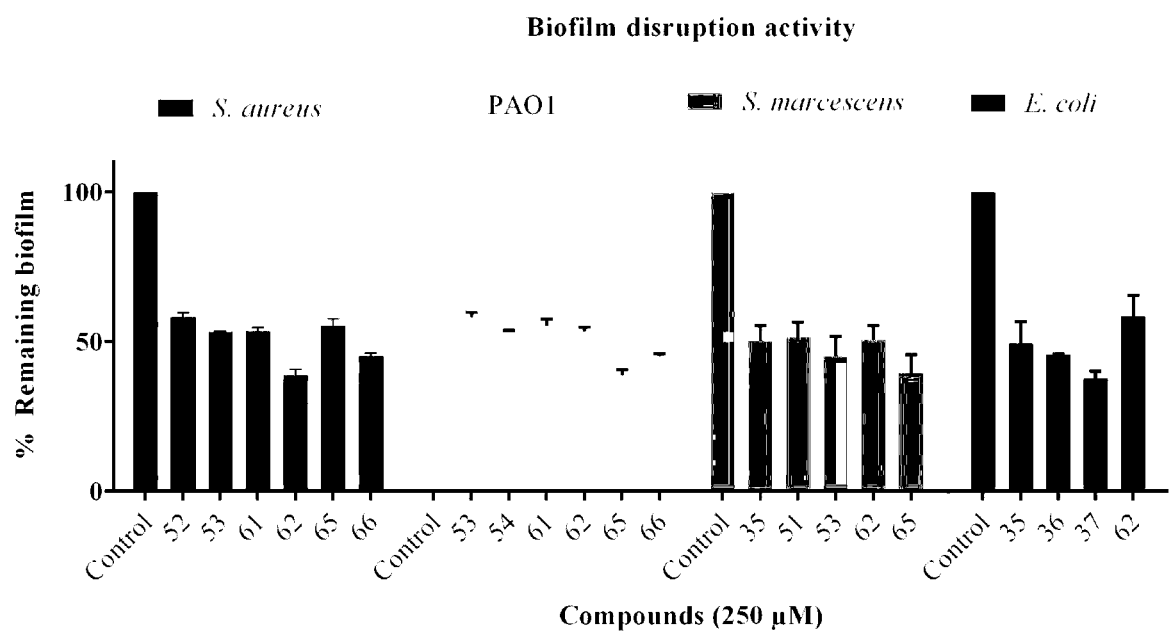
FIG. 1 shows graphs of the "% Remaining biofilm" (i.e. the percentage of biofilm relative to the control as quantified by crystal violet staining) for established biofilms of *S. aureus, Pseudomonas aeruginosa* (PAO1), *S. marcescens* and *E. coli* after 24 h treatment with 250 µM of glyoxamide-based peptidomimetics. The control represents the pre-established biofilms without any compounds. Error bars indicate the standard error of the mean (SEM) of three independent experiments.

Preferred embodiments of the present invention are described below by way of example only.

Definitions

Unless otherwise herein defined, the following terms will be understood to have the general meanings which follow. The terms referred to below have the general meanings which follow when the term is used alone and when the term is used in combination with other terms, unless otherwise indicated. Hence, for example, the definition of "alkyl" applies to "alkyl" as well as the "alkyl" portions of "haloalkyl", "heteroalkyl", "arylalkyl" etc.

The term "alkyl" refers to a straight chain or branched chain saturated hydrocarbyl group. Unless indicated otherwise, preferred are $C_{1-6}$alkyl and $C_{1-4}$alkyl groups. The term "$C_{x-y}$alkyl", where x and y are integers, refers to an alkyl group having x to y carbon atoms. For example, the term "$C_{1-6}$alkyl" refers to an alkyl group having 1 to 6 carbon atoms. Examples of $C_{1-6}$alkyl include methyl (Me), ethyl (Et), propyl (Pr), isopropyl (i-Pr), butyl (Bu), isobutyl (i-Bu), sec-butyl (s-Bu), tert-butyl (t-Bu), pentyl, neopentyl, hexyl and the like. Unless the context requires otherwise, the term "alkyl" also encompasses alkyl groups containing one less hydrogen atom such that the group is attached via two positions, i.e. divalent.

The term "alkenyl" refers to a straight chain or branched chain hydrocarbyl group having at least one double bond of either E- or Z-stereochemistry where applicable. Unless indicated otherwise, preferred are $C_{2-6}$alkenyl and $C_{2-3}$alkenyl groups. The term "$C_{x-y}$alkenyl", where x and y are integers, refers to an alkenyl group having x to y carbon atoms. For example, the term "$C_{2-6}$alkenyl" refers to an alkenyl group having 2 to 6 carbon atoms. Examples of $C_{2-6}$alkenyl include vinyl, 1-propenyl, 1- and 2-butenyl and 2-methyl-2-propenyl. Unless the context requires otherwise, the term "alkenyl" also encompasses alkenyl groups containing one less hydrogen atom such that the group is attached via two positions, i.e. divalent.

The term "alkynyl" refers to a straight chain or branched chain hydrocarbyl group having at least one triple bond. Unless indicated otherwise, preferred are $C_{2-6}$alkynyl and $C_{2-3}$alkynyl groups. The term "$C_{x-y}$alkynyl", where x and y are integers, refers to an alkynyl group having x to y carbon atoms. For example, the term "$C_{2-6}$alkynyl" refers to an alkynyl group having 2 to 6 carbon atoms. Examples of $C_{2-6}$alkynyl include ethynyl, 1-propynyl, 1- and 2-butynyl, 2-pentynyl, 3-pentynyl, 4-pentynyl, 2-hexynyl, 3-hexynyl, 4-hexynyl and 5-hexynyl and the like. Unless the context indicates otherwise, the term "alkynyl" also encompasses alkynyl groups containing one less hydrogen atom such that the group is attached via two positions, i.e. divalent.

The term "$C_{3-8}$cycloalkyl" refers to a non-aromatic cyclic hydrocarbyl group having from 3 to 8 carbon atoms. Such groups include cyclopropyl, cyclobutyl, cyclopentyl, cyclohexyl, cycloheptyl and cyclooctyl. The term "$C_{3-8}$cycloalkyl" encompasses groups where the cyclic hydrocarbyl group is saturated such as cyclohexyl or unsaturated such as cyclohexenyl. $C_{3-6}$cycloalkyl such as cyclopropyl, cyclobutyl, cyclopentyl and cyclohexyl are preferred.

The terms "hydroxy" and "hydroxyl" refer to the group —OH.

The term "oxo" refers to the group =O.

The term "heteroalkyl" refers to an alkyl group as defined above covalently bound via a heteroatom linkage (e.g. via O, N or S). Examples where the "heteroalkyl" group is covalently bound to an $SP^3$ carbon include ethers (e.g. alkoxy), thioethers and amino groups. Unless indicated otherwise, preferred are $C_{1-6}$heteroalkyl, $C_{1-4}$heteroalkyl and $C_{1-3}$heteroalkyl groups.

The term "alkoxy" refers to an alkyl group as defined above covalently bound via an O linkage, such as methoxy, ethoxy, propoxy, isopropoxy, butoxy, tert-butoxy and pentoxy. Unless indicated otherwise, preferred are $C_{1-6}$alkoxy, $C_{1-4}$alkoxy and $C_{1-3}$alkoxy groups.

The term "haloalkyl" refers to a $C_{1-6}$alkyl which is substituted with one or more halogens, such as, for example, —CHF$_2$, —CH$_2$CF$_3$, —CF$_2$CF$_3$ and —CF$_3$. Unless indicated otherwise, halo$C_{1-3}$alkyl groups are preferred.

The term "halo$C_{1-6}$alkoxy" refers to a $C_{1-6}$alkoxy which is substituted with one or more halogens. Halo$C_{1-3}$alkoxy groups are preferred, such as, for example, —OCHF$_2$ and —OCF$_3$.

The term "carboxylate" or "carboxyl" refers to the group —COO⁻ or —COOH.

The term "ester" refers to a carboxyl group having the hydrogen replaced with, for example, an alkyl group ("alkylester" or "alkylcarbonyl"), an aryl or aralkyl group ("arylester" or "aralkylester") and so on. CO$_2$C$_{1-3}$alkyl groups are preferred, such as for example, methylester (—CO$_2$Me), ethylester (—CO$_2$Et) and propylester (—CO$_2$Pr) and reverse esters thereof (e.g. —OC(O)Me, —OC(O)Et and —OC(O)Pr).

The term "cyano" refers to the group —CN.

The term "nitro" refers to the group —NO$_2$.

The term "amino" refers to the group —NH$_2$.

The term "substituted amino" or "secondary amino" refers to an amino group having a hydrogen replaced with, for example, an alkyl group ("alkylamino"), an aryl or aralkyl group ("arylamino", "aralkylamino") and so on. $C_{1-3}$alkylamino groups are preferred, such as for example, methylamino (—NHMe), ethylamino (—NHEt) and propylamino (—NHPr).

The term "disubstituted amino" or "tertiary amino" refers to an amino group having the two hydrogens replaced with, for example, an alkyl group, which may be the same or different ("di(alkyl)amino"), an aryl and alkyl group ("aryl(alkyl)amino") and so on. Di($C_{1-3}$alkyl)amino groups are preferred, such as, for example, dimethylamino (—NMe$_2$), diethylamino (—NEt$_2$), dipropylamino (—NPr$_2$) and variations thereof (e.g. —N(Me)(Et) and so on).

The term "acyl" or "aldehyde" refers to the group —C(=O)H.

The term "substituted acyl" or "ketone" refers to an acyl group having the hydrogen replaced with, for example, an alkyl group ("alkylacyl" or "alkylketone"), an aryl group ("arylketone"), an aralkyl group ("aralkylketone") and so on. Unless indicated otherwise, $C_{1-6}$alkylacyl and $C_{1-3}$alkylacyl groups are preferred.

The term "amido" or "amide" refers to the group —C(O)NH$_2$.

The term "aminoacyl" refers to the group —NHC(O)H.

The term "substituted amido" or "substituted amide" refers to an amido group having a hydrogen replaced with, for example, an alkyl group ("alkylamido" or "alkylamide"), an aryl ("arylamido"), aralkyl group ("aralkylamido") and so on. $C_{1-3}$alkylamide groups are preferred, such as, for example, methylamide (—C(O)NHMe), ethylamide (—C(O)NHEt) and propylamide (—C(O)NHPr) and reverse amides thereof (e.g. —NHC(O)Me, —NHC(O)Et and —NHC(O)Pr).

The term "disubstituted amido" or "disubstituted amide" refers to an amido group having the two hydrogens replaced with, for example, an alkyl group ("di(alkyl)amido" or "di(alkyl)amide"), an aralkyl and alkyl group ("alkyl(aralkyl)amido") and so on. Di($C_{1-3}$alkyl)amide groups are preferred, such as, for example, dimethylamide (—C(O)NMe$_2$), diethylamide (—C(O)NEt$_2$) and dipropylamide (—C(O)NPr$_2$) and variations thereof (e.g. —C(O)N(Me)Et and so on) and reverse amides thereof.

The term "thiol" refers to the group —SH.

The term "$C_{1-6}$alkylthio" refers to a thiol group having the hydrogen replaced with a $C_{1-6}$alkyl group. $C_{1-3}$alkylthio groups are preferred, such as, for example, thiolmethyl, thiolethyl and thiolpropyl.

The term "thioxo" refers to the group =S.

The term "sulfinyl" refers to the group —S(=O)H.

The term "substituted sulfinyl" or "sulfoxide" refers to a sulfinyl group having the hydrogen replaced with, for example, a $C_{1-6}$alkyl group ("$C_{1-6}$alkylsulfinyl" or "$C_{1-6}$alkylsulfoxide"), an aryl ("arylsulfinyl"), an aralkyl ("aralkylsulfinyl") and so on. $C_{1-3}$alkylsulfinyl groups are preferred, such as, for example, —SOmethyl, —SOethyl and —SOpropyl.

The term "sulfonyl" refers to the group —SO$_2$H.

The term "substituted sulfonyl" refers to a sulfonyl group having the hydrogen replaced with, for example, a $C_{1-6}$alkyl group ("$C_{1-6}$alkylsulfonyl"), an aryl ("arylsulfonyl"), an aralkyl ("aralkylsulfonyl") and so on. Sulfonyl$C_{1-3}$alkyl groups are preferred, such as, for example, —SO$_2$Me, —SO$_2$Et and —SO$_2$Pr.

The term "sulfonylamido" or "sulfonamide" refers to the group —SO$_2$NH$_2$.

The term "substituted sulfonamido" or "substituted sulphonamide" refers to a sulfonylamido group having a hydrogen replaced with, for example, a $C_{1-6}$alkyl group ("$C_{1-6}$alkylsulfonylamido"), an aryl ("arylsulfonamide"), aralkyl ("aralkylsulfonamide") and so on. $C_{1-3}$alkylsulfonylamido groups are preferred, such as, for example, —SO$_2$NHMe, —SO$_2$NHEt and —SO$_2$NHPr and reverse sulfonamides thereof (e.g. —NHSO$_2$Me, —NHSO$_2$Et and —NHSO$_2$Pr).

The term "disubstituted sulfonamido" or "disubstituted sulphonamide" refers to a sulfonylamido group having the two hydrogens replaced with, for example, a $C_{1-6}$alkyl group, which may be the same or different ("di($C_{1-6}$alkyl)sulfonylamido"), an aralkyl and alkyl group ("aralkyl(alkyl)sulfonamido") and so on. Di($C_{1-3}$alkyl)sulfonylamido groups are preferred, such as, for example, —SO$_2$NMe$_2$, —SO$_2$NEt$_2$ and —SO$_2$NPr$_2$ and variations thereof (e.g. —SO$_2$N(Me)Et and so on) and reverse sulfonamides thereof.

The term "sulfate" refers to the group —OS(O)$_2$OH and includes groups having the hydrogen replaced with, for example, a $C_{1-6}$alkyl group ("$C_{1-6}$alkylsulfate"), an aryl ("arylsulfate"), an aralkyl ("aralkylsulfate") and so on. $C_{1-3}$alkylsulfates are preferred, such as, for example, —OS(O)$_2$OMe, —OS(O)$_2$OEt and —OS(O)$_2$OPr.

The term "sulfonate" refers to the group —SO$_3$H and includes groups having the hydrogen replaced with, for example, a $C_{1-6}$alkyl group ("$C_{1-6}$alkylsulfonate"), an aryl ("arylsulfonate"), an aralkyl ("aralkylsulfonate") and so on. $C_{1-3}$alkylsulfonates are preferred, such as, for example, —SO$_3$Me, —SO$_3$Et and —SO$_3$Pr.

The term "aryl" refers to a carbocyclic (non-heterocyclic) aromatic ring or mono-, bi- or tri-cyclic ring system. The aromatic ring or ring system is generally composed of 6 to 10 carbon atoms. Examples of aryl groups include but are not limited to phenyl, biphenyl, naphthyl and tetrahydronaphthyl. 6-membered aryls such as phenyl are preferred.

The term "arylalkyl" or "aralkyl" refers to an aryl$C_{1-6}$alkyl- such as benzyl.

The term "arylalkoxy" refers to aryl$C_{1-6}$alkoxy- such as benzyloxy.

The term "heterocyclyl" refers to a moiety obtained by removing a hydrogen atom from a ring atom of a heterocyclic compound which moiety has from 3 to 10 ring atoms (unless otherwise specified), of which 1, 2, 3 or 4 are ring heteroatoms, each heteroatom being independently selected from O, S and N, and the remainder of the ring atoms are carbon atoms. The term "heterocycloalkyl" refers to a heterocyclyl moiety comprising a saturated cyclic group comprising one or more ring carbons and one or more ring heteroatoms. "Heterocycloalkenyl" refers to a heterocyclyl moiety comprising a cyclic group comprising at least one carbon-carbon double bond and one or more ring heteroatoms. "Heterocycloalkynyl" refers to a heterocyclyl moiety comprising a cyclic group comprising at least one carbon-carbon triple bond and one or more ring heteroatoms.

In this context, the prefixs 3-, 4-, 5-, 6-, 7-, 8-, 9- and 10-membered denote the number of ring atoms, or range of ring atoms, whether carbon atoms or heteroatoms. For example, the term "3-10-membered heterocylyl", as used herein, refers to a heterocyclyl group having 3, 4, 5, 6, 7, 8, 9 or 10 ring atoms. Examples of heterocylyl groups include 5-6-membered monocyclic heterocyclyls and 9-10 membered fused bicyclic heterocyclyls.

Examples of monocyclic heterocyclyl groups include, but are not limited to, those containing one nitrogen atom such as aziridine (3-membered ring), azetidine (4-membered ring), pyrrolidine (tetrahydropyrrole), pyrroline (e.g., 3-pyrroline, 2,5-dihydropyrrole), 2H-pyrrole or 3H-pyrrole (isopyrrole, isoazole) or pyrrolidinone (5-membered rings), piperidine, dihydropyridine, tetrahydropyridine (6-membered rings), and azepine (7-membered ring); those containing two nitrogen atoms such as imidazoline, pyrazolidine (diazolidine), pyrazoline (dihydropyrazole) (5-membered rings), piperazine (6-membered ring); those containing one oxygen atom such as oxirane (3-membered ring), oxetane (4-membered ring), oxolane (tetrahydrofuran), oxole (dihydrofuran) (5-membered rings), oxane (tetrahydropyran), dihydropyran, pyran (6-membered rings), oxepin (7-membered ring); those containing two oxygen atoms such as dioxolane (5-membered ring), dioxane (6-membered ring), and dioxepane (7-membered ring); those containing three oxygen atoms such as trioxane (6-membered ring); those containing one sulfur atom such as thiirane (3-membered ring), thietane (4-membered ring), thiolane (tetrahydrothiophene) (5-membered ring), thiane (tetrahydrothiopyran) (6-membered ring), thiepane (7-membered ring); those containing one nitrogen and one oxygen atom such as tetrahydrooxazole, dihydrooxazole, tetrahydroisoxazole, dihydroisoxazole (5-membered rings), morpholine, tetrahydrooxazine, dihydrooxazine, oxazine (6-membered rings); those containing one nitrogen and one sulfur atom such as thiazoline, thiazolidine (5-membered rings), thiomorpholine (6-membered ring); those containing two nitrogen and one oxygen atom such as oxadiazine (6-membered ring); those containing one oxygen and one sulfur such as: oxathiole (5-membered ring) and oxathiane (thioxane) (6-membered ring); and those containing one nitrogen, one oxygen and one sulfur atom such as oxathiazine (6-membered ring).

The term "heterocyclyl" encompasses aromatic heterocyclyls and non-aromatic heterocyclyls.

The term "aromatic heterocyclyl" may be used interchangeably with the term "heteroaromatic" or the term "heteroaryl" or "hetaryl". The heteroatoms in the aromatic heterocyclyl group may be independently selected from N, S and O.

"Heteroaryl" is used herein to denote a heterocyclic group having aromatic character and embraces aromatic monocyclic ring systems and polycyclic (e.g. bicyclic) ring systems containing one or more aromatic rings. The term aromatic heterocyclyl also encompasses pseudoaromatic heterocyclyls. The term "pseudoaromatic" refers to a ring system which is not strictly aromatic, but which is stabilized by means of delocalization of electrons and behaves in a similar manner to aromatic rings. The term aromatic heterocyclyl therefore covers polycyclic ring systems in which all of the fused rings are aromatic as well as ring systems where one or more rings are non-aromatic, provided that at least one ring is aromatic. In polycyclic systems containing both aromatic and non-aromatic rings fused together, the group may be attached to another moiety by the aromatic ring or by a non-aromatic ring.

Examples of heteroaryl groups are monocyclic and bicyclic groups containing from five to ten ring members. The heteroaryl group can be, for example, a five membered or six membered monocyclic ring or a bicyclic structure formed from fused five and six membered rings or two fused six membered rings or two fused five membered rings. Each ring may contain up to four heteroatoms selected from nitrogen, sulphur and oxygen. The heteroaryl group can contain up to 4 heteroatoms, more typically up to 3 heteroatoms, more usually up to 2 heteroatoms. In one embodiment, the heteroaryl group contains at least one ring nitrogen atom. The nitrogen atoms in the heteroaryl group can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Aromatic heterocyclyl groups may be 5-membered or 6-membered mono-cyclic aromatic ring systems.

Examples of 5-membered monocyclic heteroaryl groups include but are not limited to furanyl, thienyl, pyrrolyl, oxazolyl, oxadiazolyl (including 1,2,3- and 1,2,4-oxadiazolyls and furazanyl, i.e. 1,2,5-oxadiazolyl), thiazolyl, isoxazolyl, isothiazolyl, pyrazolyl, imidazolyl, triazolyl (including 1,2,3-, 1,2,4- and 1,3,4-triazolyls), oxatriazolyl, tetrazolyl, thiadiazolyl (including 1,2,3- and 1,3,4-thiadiazolyls) and the like.

Examples of 6-membered monocyclic heteroaryl groups include but are not limited to pyridinyl, pyrimidinyl, pyridazinyl, pyrazinyl, triazinyl, pyranyl, oxazinyl, dioxinyl, thiazinyl, thiadiazinyl and the like. Examples of 6-membered aromatic heterocyclyls containing nitrogen include pyridyl (1 nitrogen), pyrazinyl, pyrimidinyl and pyridazinyl (2 nitrogens).

Aromatic heterocyclyl groups may also be bicyclic or polycyclic heteroaromatic ring systems such as fused ring systems (including purine, pteridinyl, naphthyridinyl, 1H-thieno[2,3-c]pyrazolyl, thieno[2,3-b]furyl and the like) or linked ring systems (such as oligothiophene, polypyrrole and the like). Fused ring systems may also include aromatic 5-membered or 6-membered heterocyclyls fused to carbocyclic aromatic rings such as phenyl, naphthyl, indenyl, azulenyl, fluorenyl, anthracenyl and the like, such as 5-membered aromatic heterocyclyls containing nitrogen fused to phenyl rings, 5-membered aromatic heterocyclyls containing 1 or 2 nitrogens fused to phenyl ring.

A bicyclic heteroaryl group may be, for example, a group selected from: a) a benzene ring fused to a 5- or 6-membered ring containing 1, 2 or 3 ring heteroatoms; b) a pyridine ring fused to a 5- or 6-membered ring containing 1, 2 or 3 ring heteroatoms; c) a pyrimidine ring fused to a 5- or 6-membered ring containing 1 or 2 ring heteroatoms; d) a pyrrole ring fused to a 5- or 6-membered ring containing 1, 2 or 3 ring heteroatoms; e) a pyrazole ring fused to a 5- or 6-membered ring containing 1 or 2 ring heteroatoms; f) an imidazole ring fused to a 5- or 6-membered ring containing 1 or 2 ring heteroatoms; g) an oxazole ring fused to a 5- or 6-membered ring containing 1 or 2 ring heteroatoms; h) an isoxazole ring fused to a 5- or 6-membered ring containing 1 or 2 ring heteroatoms; i) a thiazole ring fused to a 5- or 6-membered ring containing 1 or 2 ring heteroatoms; j) an isothiazole ring fused to a 5- or 6-membered ring containing 1 or 2 ring heteroatoms; k) a thiophene ring fused to a 5- or 6-membered ring containing 1, 2 or 3 ring heteroatoms; l) a furan ring fused to a 5- or 6-membered ring containing 1, 2 or 3 ring heteroatoms; m) a cyclohexyl ring fused to a 5- or 6-membered aromatic ring containing 1, 2 or 3 ring heteroatoms; and n) a cyclopentyl ring fused to a 5- or 6-membered aromatic ring containing 1, 2 or 3 ring heteroatoms.

Particular examples of bicyclic heteroaryl groups containing a five membered ring fused to another five membered ring include but are not limited to imidazothiazole (e.g. imidazo[2,1-b]thiazole) and imidazoimidazole (e.g. imidazo[1,2-a]imidazole).

Particular examples of bicyclic heteroaryl groups containing a six membered ring fused to a five membered ring include but are not limited to benzofuran, benzothiophene, benzimidazole, benzoxazole, isobenzoxazole, benzisoxazole, benzothiazole, benzisothiazole, isobenzofuran, indole, isoindole, indolizine, indoline, isoindoline, purine (e.g., adenine, guanine), indazole, pyrazolopyrimidine (e.g. pyrazolo[1,5-a]pyrimidine), benzodioxole and pyrazolopyridine (e.g. pyrazolo[1,5-a]pyridine) groups. A further example of a six membered ring fused to a five membered ring is a pyrrolopyridine group such as a pyrrolo[2,3-b]pyridine group.

Particular examples of bicyclic heteroaryl groups containing two fused six membered rings include, but are not limited to, quinoline, isoquinoline, chroman, thiochroman, chromene, isochromene, isochroman, benzodioxan, quinolizine, benzoxazine, benzodiazine, pyridopyridine, quinoxaline, quinazoline, cinnoline, phthalazine, naphthyridine and pteridine groups.

Examples of heteroaryl groups containing an aromatic ring and a non-aromatic ring include tetrahydroisoquinoline, tetrahydroquinoline, dihydrobenzothiophene, dihydrobenzofuran, 2,3-dihydro-benzo[1,4]dioxine, benzo[1,3]dioxole, 4,5,6,7-tetrahydrobenzofuran, indoline and isoindoline groups.

Examples of aromatic heterocyclyls fused to carbocyclic aromatic rings may therefore include, but are not limited to, benzothiophenyl, indolyl, isoindolyl, benzofuranyl, isobenzofuranyl, benzimidazolyl, indazolyl, benzoxazolyl, benzisoxazolyl, isobenzoxazoyl, benzothiazolyl, benzisothiazolyl, quinolinyl, isoquinolinyl, quinoxalinyl, quinazolinyl, cinnolinyl, benzotriazinyl, phthalazinyl, carbolinyl and the like.

The term "non-aromatic heterocyclyl" encompasses saturated and unsaturated rings which contain at least one heteroatom selected from the group consisting of N, S and O.

Non-aromatic heterocyclyls may be 3-7 membered mono-cyclic rings.

Examples of 5-membered non-aromatic heterocyclyl rings include 2H-pyrrolyl, 1-pyrrolinyl, 2-pyrrolinyl, 3-pyrrolinyl, pyrrolidinyl, 1-pyrrolidinyl, 2-pyrrolidinyl, 3-pyrrolidinyl, tetrahydrofuranyl, tetrahydrothiophenyl, pyrazolinyl, 2-pyrazolinyl, 3-pyrazolinyl, pyrazolidinyl, 2-pyrazolidinyl, 3-pyrazolidinyl, imidazolidinyl, 3-dioxalanyl, thiazolidinyl, isoxazolidinyl, 2-imidazolinyl and the like.

Examples of 6-membered non-aromatic heterocyclyls include piperidinyl, piperidinonyl, pyranyl, dihyrdopyranyl, tetrahydropyranyl, 2H-pyranyl, 4H-pyranyl, thianyl, thianyl oxide, thianyl dioxide, piperazinyl, diozanyl, 1,4-dioxinyl, 1,4-dithianyl, 1,3,5-triozalanyl, 1,3,5-trithianyl, 1,4-morpholinyl, thiomorpholinyl, 1,4-oxathianyl, triazinyl, 1,4-thiazinyl and the like.

Examples of 7-membered non-aromatic heterocyclyls include azepanyl, oxepanyl, thiepanyl and the like.

Non-aromatic heterocyclyl rings may also be bicyclic heterocyclyl rings such as linked ring systems (for example uridinyl and the like) or fused ring systems. Fused ring systems include non-aromatic 5-membered, 6-membered or 7-membered heterocyclyls fused to non-aromatic carbocyclic rings.

The term "halo" refers to fluoro, chloro, bromo or iodo.

Unless otherwise defined, the term "optionally substituted", or "substituted or unsubstituted", as used herein indicates a group may or may not be substituted with 1, 2, 3, 4 or more groups, preferably 1, 2 or 3 groups, more preferably 1 or 2 groups, independently selected from the group consisting of alkyl (e.g. $C_{1-6}$alkyl), alkenyl (e.g. $C_{2-6}$alkenyl), alkynyl (e.g. $C_{2-6}$alkynyl), cycloalkyl (e.g. $C_{3-8}$cycloalkyl), hydroxyl, oxo, heteroalkyl, alkoxy (e.g. $C_{1-6}$alkoxy), aryloxy, aryl$C_{1-6}$alkoxy, halo, halo$C_{1-6}$alkyl (such as —$CF_3$ and —$CHF_2$), halo$C_{1-6}$alkoxy (such as —$OCF_3$ and —$OCHF_2$), carboxyl, esters, cyano, nitro, amino, substituted amino, disubstituted amino, acyl, substituted acyl, ketones, amides, aminoacyl, substituted amides, disubstituted amides, thiol, alkylthio, thioxo, sulfates, sulfonates, sulfinyl, substituted sulfinyl, sulfonyl, substituted sulfonyl, sulfonylamides, substituted sulfonamides, disubstituted sulfonamides, aryl, aryl$C_{1-6}$alkyl, heterocyclyl$C_{1-6}$alkyl, aryl$C_{2-6}$alkenyl, heterocyclyl$C_{2-6}$alkenyl, aryl$C_{2-6}$alkynyl, heterocyclyl$C_{2-6}$alkynyl, heteroaryl$C_{1-6}$alkyl, heteroaryl$C_{2-6}$alkenyl, heteroaryl$C_{2-6}$alkynyl, heterocyclyl and heteroaryl, wherein each alkyl, alkenyl, alkynyl, cycloalkyl, aryl and heterocyclyl and groups containing them may be further optionally substituted. Optional substituents in the case of heterocycles containing N may also include but are not limited to $C_{1-6}$alkyl i.e. N—$C_{1-6}$alkyl.

For optionally substituted "alkyl", "alkenyl" and "alkynyl", the optional substituent or substituents are preferably selected from amino, substituted amino, disubstituted amino, aryl, halo (e.g. F, Cl, Br, I), heterocyclyl, $C_{3-8}$cycloalkyl, $C_{1-6}$alkoxy, hydroxyl, oxo, aryloxy, halo$C_{1-6}$alkyl, halo$C_{1-6}$alkoxyl and carboxyl. Each of these optional substituents may also be optionally substituted with any of the optional substituents referred to above, where nitro, amino, substituted amino, cyano, heterocyclyl (including non-aromatic heterocyclyl and heteroaryl), $C_{1-6}$alkyl, $C_{2-6}$alkenyl, $C_{2-6}$alkynyl, $C_{1-6}$alkoxy, halo$C_{1-6}$alkyl, halo$C_{1-6}$alkoxy, halo, hydroxyl and carboxyl are preferred.

For substituted or unsubstituted "ammonium", the optional substituent or substituents are preferably selected from $C_{1-3}$alkyl, such as $C_1$alkyl, $C_2$alkyl or $C_3$alkyl. More preferably, the optional substituent or substituents are $CH_3$.

For substituted or unsubstituted "amino", the optional substituent or substituents are preferably selected from $C_{1-3}$alkyl, such as $C_1$alkyl, $C_2$alkyl or $C_3$alkyl. More preferably, the optional substituent or substituents are $CH_3$.

It will be understood that suitable derivatives of aromatic heterocyclyls containing nitrogen include N-oxides thereof.

As a person skilled in the art will appreciate, drawings of chemical structures in this document follow the generally accepted conventions. For example, for compounds of Formula (I) as described herein, when p is 0, 1, 2 or 3, a person skilled in the art will appreciate that the phenyl ring will contain —H at the unsubstituted positions (i.e. for carbon atoms not having an $R_1$ group attached, the valence will be satisfied by —H). For example, when p=0, the compound of Formula (I) will be represented by:

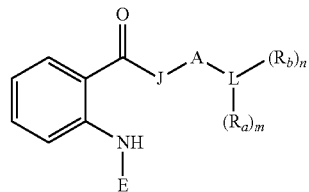

Compounds of Formula (I)

In one aspect, the present invention provides a compound of Formula (I):

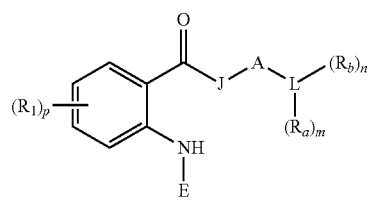

(I)

wherein:
J is

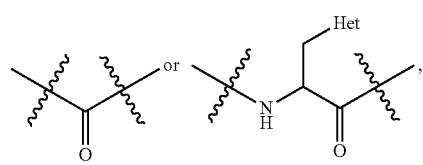

wherein Het is substituted or unsubstituted heteroaryl;

A is —NH—, —O— or —S—;

L is a saturated or unsaturated hydrocarbyl group having 1 to 12 carbon atoms, or L is —$(CH_2—CH_2—O)_r$— wherein r is 2, 3 or 4;

E is a hydrophobic group selected from —C(=O)$R_e$ or —$SO_2R_e$, wherein $R_e$ is $C_{6-18}$alkyl, $C_{6-18}$alkenyl, $C_{6-18}$alkynyl, aryl or heteroaryl, and wherein $R_e$ may optionally be substituted;

$R_a$ is independently selected from a substituted or unsubstituted amino group, a guanidine (—NH—C(=NH)(NH$_2$)) group, a $CH_3$-substituted guanidine (—[NCH$_3$—C(=NH)(NH$_2$)]) group, a substituted or unsubstituted ammonium group, a guanidinium (—[NH—C(=NH)(NH$_3$)]$^+$) group or a $CH_3$-substituted guanidinium (—[NCH$_3$—C(=NH)(NH$_3$)]$^+$) group;

m is 1, 2 or 3;

$R_b$, when present, is independently selected from: a substituted or unsubstituted amino group, a guanidine (—NH—C(=NH)(NH$_2$)) group, a CH$_3$-substituted guanidine (—[NCH$_3$—C(=NH)(NH$_2$)]) group, a substituted or unsubstituted ammonium group, a guanidinium (—[NH—C(=NH)(NH$_3$)]$^+$) group, a CH$_3$-substituted guanidinium (—[NCH$_3$—C(=NH)(NH$_3$)]$^+$) group, a $R_e$-substituted or unsubstituted triazolyl group, —CONHR$_c$ or —COOR$_c$, wherein $R_c$ is H, a straight or branched C$_{1-12}$alkyl group, substituted or unsubstituted aryl, or substituted or unsubstituted heteroaryl, or $R_e$ is -L-(R$_a$)$_m$, wherein L, R$_a$ and m are as defined above and wherein L may optionally be substituted with —CONHR$_d$ or —COOR$_d$, wherein $R_d$ is a straight or branched C$_{1-12}$alkyl group;

n is 0, 1, 2 or 3;

$R_1$, when present, is independently selected from Br, Cl, F, —C$_{1-3}$alkoxy, substituted or unsubstituted aryl, substituted or unsubstituted heteroaryl, —SO$_3$H, —SO$_3$Na, —SO$_2$(C$_{1-3}$alkyl), —SO$_2$(OO$_{1-3}$alkyl) or —SO$_2$(N(C$_{1-3}$alkyl)(C$_{1-3}$alkyl)); and p is 0, 1, 2, 3 or 4;

or a salt thereof.

In some embodiments of Formula (I), J is

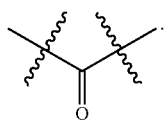 [SMILES: *C(*)=O]

In some embodiments of Formula (I), J is

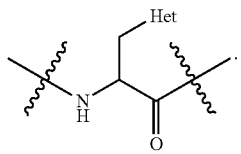

In some embodiments of Formula (I), Het is a substituted or unsubstituted indolyl, e.g. 3-indolyl.

In some embodiments of Formula (I), J is

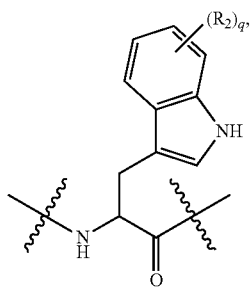

wherein R$_2$ is independently selected from C$_{1-6}$alkyl, C$_{2-6}$alkenyl, C$_{2-6}$alkynyl, C$_{3-8}$cycloalkyl, hydroxyl, C$_{1-6}$alkoxy), arylC$_{1-6}$alkoxy, halo, haloC$_{1-6}$alkyl, haloC$_{1-6}$alkoxy, cyano and amino, and q is 0, 1, 2, 3 or 4. In some embodiments, q is 1 and R$_2$ is C$_{1-6}$alkyl, hydroxyl or C$_{1-6}$alkoxy.

In some embodiments of Formula (I), J is

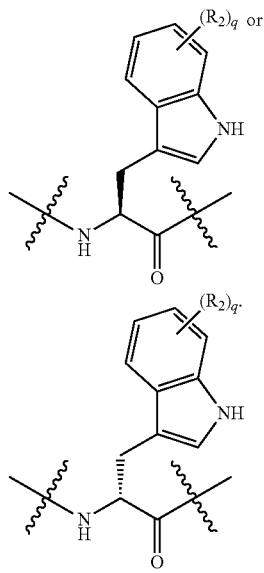

In some embodiments of Formula (I), q is 0. Thus, in these embodiments, J is

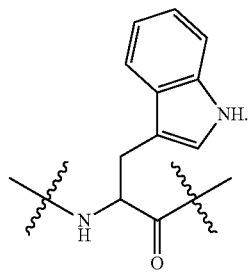 [SMILES: *NC(Cc1c[nH]c2ccccc12)C(*)=O]

In some embodiments of Formula (I), J is

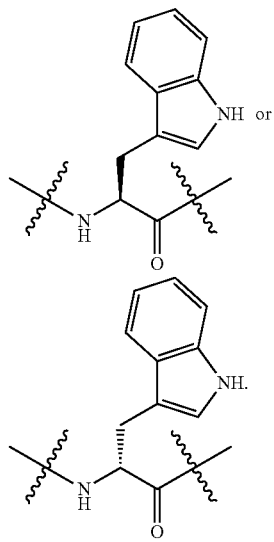

Preferably, J is

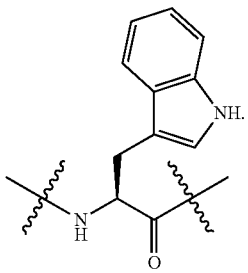 [SMILES: *N[C@@H](Cc1c[nH]c2ccccc12)C(*)=O]

In some embodiments of Formula (I), A is —NH—.

L is a linking group. In some embodiments of Formula (I), L is a straight chain or branched $C_{1-12}$alkyl, $C_{2-12}$alkenyl or $C_{2-12}$alkynyl. In some embodiments, L contains a cyclic group. In some embodiments, L is a $C_{1-12}$alkyl, $C_{2-12}$alkenyl or $C_{2-12}$alkynyl, which may optionally contain an aromatic or non-aromatic carbocyclic group. For example, L may be —CH$_2$—, $C_2$alkyl, $C_2$alkenyl, $C_2$alkynyl, $C_3$alkyl, $C_3$alkenyl, $C_3$alkynyl, $C_4$alkyl, $C_4$alkenyl, $C_4$alkynyl, $C_5$alkyl, $C_5$alkenyl, $C_5$alkynyl, $C_6$alkyl, $C_6$alkenyl, $C_6$alkynyl, $C_7$alkyl, $C_7$alkenyl, $C_7$alkynyl, $C_8$alkyl, $C_8$alkenyl, $C_8$alkynyl, $C_9$alkyl, $C_9$alkenyl, $C_9$alkynyl, $C_{10}$alkyl, $C_{10}$alkenyl, $C_{10}$alkynyl, $C_{11}$alkyl, $C_{11}$alkenyl, $C_{11}$alkynyl, $C_{12}$alkyl, $C_{12}$alkenyl, $C_{12}$alkynyl,

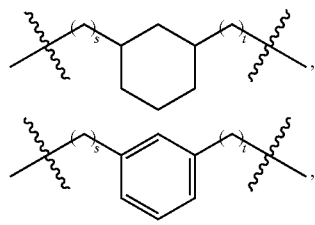

wherein each of s and t is 1, 2, 3, 4 or 5 provided that s+t≤6. In some embodiments, L is —CH$_2$CH$_2$—, —CH$_2$CH$_2$CH$_2$—, —CH$_2$CH$_2$CH$_2$CH$_2$—, —CH(CH$_3$)CH$_2$CH$_2$— or —CH$_2$CH(CH$_3$)CH$_2$—. In some embodiments, L is —CH$_2$CH$_2$— or —CH$_2$CH$_2$CH$_2$—.

In some embodiments of Formula (I), L is —(CH$_2$—CH$_2$—O)$_r$— wherein r is 2, 3 or 4, and L is substituted with 1, 2 or 3 $R_b$ groups.

In some embodiments of Formula (I), E is —C(═O)R$_e$ or —SO$_2$R$_e$, wherein R$_e$ is $C_6$alkyl, $C_6$alkenyl, $C_6$alkynyl, $C_7$alkyl, $C_7$alkenyl, $C_7$alkynyl, $C_8$alkyl, $C_8$alkenyl, $C_8$alkynyl, $C_9$alkyl, $C_9$alkenyl, $C_9$alkynyl, $C_{10}$alkyl, $C_{10}$alkenyl, $C_{10}$alkynyl, $C_{11}$alkyl, $C_{11}$alkenyl, $C_{11}$alkynyl, $C_{12}$alkyl, $C_{12}$alkenyl, $C_{12}$alkynyl, $C_{13}$alkyl, $C_{13}$alkenyl, $C_{13}$alkynyl, $C_{14}$alkyl, $C_{14}$alkenyl, $C_{14}$alkynyl, $C_{15}$alkyl, $C_{15}$alkenyl, $C_{15}$alkynyl, $C_{16}$alkyl, $C_{16}$alkenyl, $C_{16}$alkynyl, $C_{17}$alkyl, $C_{17}$alkenyl, $C_{17}$alkynyl, $C_{18}$alkyl, $C_{18}$alkenyl, $C_{18}$alkynyl, phenyl, naphthyl, anthracenyl or phenanthrenyl. In some embodiments, E is —C(═O)R$_e$ or —SO$_2$R$_e$, wherein R$_e$ is octyl, phenyl or naphthyl. In some embodiments, E is —SO$_2$R$_e$, wherein R$_e$ is octyl. In some embodiments, E is —C(═O)R$_e$ wherein R$_e$ is naphthyl.

In some embodiments of Formula (I), when $R_a$ is —[N(CH$_3$)$_3$]$^+$ or —[NH(CH$_3$)$_2$]$^+$, E is not —C(═O)R$_e$ wherein R$_e$ is 2-naphthyl, phenyl or —(CH$_2$)$_4$CH$_3$.

In some embodiments of Formula (I), $R_a$ is a substituted or unsubstituted amino group. When $R_a$ is a substituted amino group, $R_a$ may be a primary, secondary or tertiary amino group.

In some embodiments of Formula (I), $R_a$ is a guanidine (—NH—C(═NH)(NH$_2$)) group or a CH$_3$-substituted guanidine (—[NCH$_3$—C(═NH)(NH$_2$)]) group.

In some embodiments of Formula (I), $R_a$ is selected from —NH$_2$, —NH(CH$_3$), and —N(CH$_3$)$_2$.

In some embodiments of Formula (I), $R_a$ is a substituted or unsubstituted ammonium group. When $R_a$ is a substituted ammonium group, $R_a$ may be a secondary, tertiary or quaternary ammonium group.

In some embodiments of Formula (I), $R_a$ is selected from —NH$_3^+$, [—NH$_2$(CH$_3$)]$^+$, [—NH(CH$_3$)$_2$]$^+$ and [—N(CH$_3$)$_3$]$^+$.

In some embodiments of Formula (I), $R_a$ is selected from a guanidinium (—[NH—C(═NH)(NH$_3$)]$^+$) group and a CH$_3$-substituted guanidinium (—[NCH$_3$—C(═NH)(NH$_3$)]$^+$) group.

In some embodiments of Formula (I), $R_b$ is absent.

In some embodiments of Formula (I), $R_b$ is present and is independently selected from: —NH$_2$, —NH(CH$_3$), —N(CH$_3$)$_2$, a guanidine (—NH—C(═NH)(NH$_2$)) group, a CH$_3$-substituted guanidine (—[NCH$_3$—C(═NH)(NH$_2$)]) group, —NH$_3^+$, [—NH$_2$(CH$_3$)]$^+$, [—NH(CH$_3$)$_2$]$^+$, [—N(CH$_3$)$_3$]$^+$, a guanidinium (—[NH—C(═NH)(NH$_3$)]$^+$) group, a CH$_3$-substituted guanidinium (—[NCH$_3$—C(═NH)(NH$_3$)]$^+$) group, triazolyl

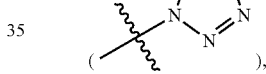

$R_c$-substituted triazolyl

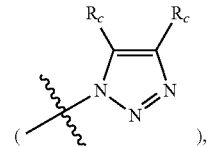

—CONHR$_c$ or —COOR$_c$, wherein each R$_c$ is independently selected from H, $C_1$alkyl, $C_2$alkyl, $C_3$alkyl, $C_4$alkyl, $C_5$alkyl, $C_6$alkyl, $C_7$alkyl, $C_8$alkyl, $C_9$alkyl, $C_{10}$alkyl, $C_{11}$alkyl, $C_{12}$alkyl, substituted or unsubstituted aryl, or substituted or unsubstituted heteroaryl, or R$_c$ is -L-(R$_a$)$_m$. In some embodiments, R$_c$ is H. In some embodiments, R$_c$ is CH$_3$. In some embodiments, R$_c$ is -L-(R$_a$)$_m$. When R$_c$ is -L-(R$_a$)$_m$, L, R$_a$ and m are as defined above and L may optionally be substituted with —CONHR$_d$ or —COOR$_d$, wherein R$_d$ is a straight or branched $C_{1-12}$alkyl.

In some embodiments of Formula (I), $R_1$ is absent.

In some embodiments of Formula (I), $R_1$ is present and is independently selected from Br, Cl, F, —CH$_3$, —CH$_2$CH$_3$, —OCH$_3$, —OCH$_2$CH$_3$, —C$_6$H$_5$, —SO$_3$H, —SO$_3$Na, —SO$_2$(CH$_3$), —SO$_2$(CH$_2$CH$_3$), —SO$_2$(OCH$_3$), —SO$_2$(OCH$_2$CH$_3$), —SO$_2$N(CH$_3$)$_2$, —SO$_2$N(CH$_3$)(CH$_2$CH$_3$), or —SO$_2$N(CH$_2$CH$_3$)$_2$. In some embodiments, R$_1$ is Br. In some embodiments, R$_1$ is Cl. In some embodiments, R$_1$ is F. In some embodiments, R$_1$ is —CH$_3$. In some embodiments, R₁ is Br and is in the para-position to the amino group. In some embodiments, R₁ is —C₆H₅.

When m is 2 or 3, each $R_a$ is independently selected. That is, each $R_a$ may be the same or different.

In some embodiments of Formula (I), m is 1 or 2. In some embodiments of Formula (I), m is 1.

When n is 2 or 3, each $R_b$ is independently selected. That is, each $R_b$ may be the same or different.

In some embodiments of Formula (I), n is 1 or 2. In some embodiments of Formula (I), n is 1.

In some embodiments of Formula (I), m is 1 and n is 1.

When p is 2, 3 or 4, each R₁ is independently selected. That is, each R₁ may be the same or different.

In some embodiments of Formula (I), p is 1 or 2. In some embodiments of Formula (I), p is 1 and R₁ is in the para-position to the amino group.

E, together with the NH to which E is bound, forms a hydrophobic amide or sulfonamide group. E is selected from —NHC(=O)$R_e$ or —NHSO₂$R_e$, wherein $R_e$ is C₆₋₁₈alkyl, C₆₋₁₈alkenyl, C₆₋₁₈alkynyl, aryl (e.g. mono, di, and tricyclic aromatic rings, such as phenyl, 1-naphthyl or 2-naphthyl), or heteroaryl (e.g. five-membered and six-membered heteroaromatic rings, and fused ring systems comprising five-membered and six-membered heteroaromatic rings), and wherein $R_e$ may optionally be substituted, provided that E is a hydrophobic group. E is typically a non-polar group. Examples of optional substituents on the $R_e$ group include, for example, C₁₋₁₂alkyl, C₂₋₁₂alkenyl, C₂₋₁₂alkynyl, aryl (e.g. mono, di, and tricyclic aromatic rings, such as phenyl, 1-naphthyl or 2-naphthyl), substituted aryl (e.g. substituted mono, di, and tricyclic aromatic rings, such as substituted phenyl, substituted 1-naphthyl or substituted 2-naphthyl), or heteroaryl (e.g. five-membered and six-membered heteroaromatic rings, and fused ring systems comprising five-membered and six-membered heteroaromatic rings), and substituted heteroaryl (e.g. substituted five-membered and six-membered heterocyclic rings, and substituted fused ring systems comprising five-membered and six-membered heterocyclic rings).

In some embodiments, E is unsubstituted or substituted benzoyl, unsubstituted or substituted 1-naphthoyl, or unsubstituted or substituted 2-naphthoyl. In some embodiments, E is benzoyl, 1-naphthoyl or 2-naphthoyl.

In some embodiments, the salt of the compound of Formula (I) is a hydrochloride salt, a hydrobromide salt or an iodide salt. In some embodiments, the salt of the compound of Formula (I) is an acid addition salt of a trihaloacetic acid (e.g. trifluoroacetic acid).

In some embodiments, the compound of Formula (I) is a compound of Formula (Ia):

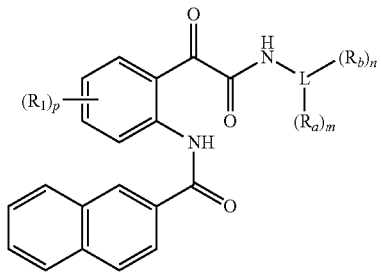

wherein:

L is C₂alkyl, C₃alkyl, C₄alkyl, C₅alkyl, C₆alkyl or C₇alkyl;

$R_a$ is —NH₃⁺, [—NH₂(CH₃)]⁺, [—NH(CH₃)₂]⁺, [—N(CH₃)₃]⁺, a guanidinium (—[NH—C(=NH)(NH₃)]⁺) group or a CH₃-substituted guanidinium (—[NCH₃—C(=NH)(NH₃)]⁺) group;

m is 1;

$R_b$, when present, is independently selected from: —NH₃⁺, [—NH₂(CH₃)]⁺, [—NH(CH₃)₂]⁺, [—N(CH₃)₃]⁺, a guanidinium (—[NH—C(=NH)(NH₃)]⁺) group, a CH₃-substituted guanidinium (—[NCH₃—C(=NH)(NH₃)]⁺) group, triazolyl

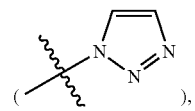

$R_c$-substituted triazolyl

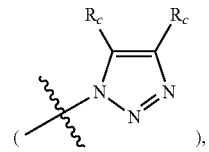

—CONHR$_c$ or —COOR$_c$, wherein each R$_c$ is independently selected from H, C₁alkyl, C₂alkyl, C₃alkyl, C₄alkyl, C₅alkyl, C₆alkyl, C₇alkyl, C₈alkyl, C₉alkyl, C₁₀alkyl, C₁₁alkyl, C₁₂alkyl, substituted or unsubstituted aryl, or substituted or unsubstituted heteroaryl; or R$_c$ is -L-(R$_a$)$_m$, wherein L, R$_a$ and m are as defined above and wherein L may optionally be substituted with —CONHR$_d$ or —COOR$_d$, wherein R$_d$ is a straight or branched C₁₋₁₂alkyl group;

n is 0 or 1;

R₁ is Br, Cl, F or —CH₃; and p is 0 or 1.

The compounds of Formula (Ia) are glyoxamide-based compounds comprising a hydrophobic group and an ammonium or guanidinium moiety.

In some embodiments of Formula (Ia), L is C₃alkyl, C₄alkyl or C₅alkyl.

In some embodiments of Formula (Ia), R$_a$ is a guanidinium (—[NH—C(=NH)(NH₃)]⁺) group.

In some embodiments of Formula (Ia), n is 0.

In some embodiments of Formula (Ia), n is 1 and R$_b$ is —CONHR$_c$ or —COOR$_c$, wherein R$_c$ is H, C₁alkyl, C₂alkyl, C₃alkyl, C₄alkyl, C₅alkyl, C₆alkyl, C₇alkyl, C₈alkyl, C₉alkyl, C₁₀alkyl, C₁₁alkyl, C₁₂alkyl, substituted or unsubstituted aryl, or substituted or unsubstituted heteroaryl, or R$_c$ is -L-(R$_a$)$_m$, wherein L, R$_a$ and m are as defined above and wherein L may optionally be substituted with —CONHR$_d$ or —COOR$_d$, wherein R$_d$ is a straight or branched C₁₋₁₂alkyl group. In some embodiments, R$_b$ is —CONHR$_c$ or —COOR$_c$, and R$_c$ is -L-(R$_a$)$_m$, wherein L is C₃alkyl, C₄alkyl or C₅alkyl, R$_a$ is a guanidinium (—[NH—C(=NH)(NH₃)]⁺) group, m is 1, and L is optionally substituted with —CONHCH₃ or —COOCH₃.

In some embodiments of Formula (Ia), $R_b$ is selected from:

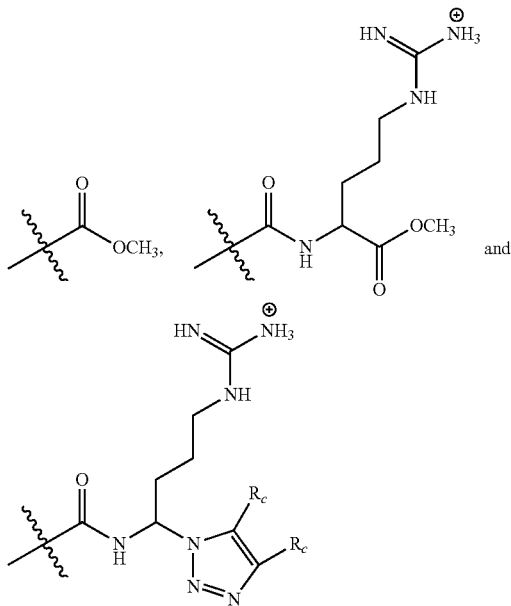

wherein each $R_c$ is independently selected from H, $C_1$alkyl, $C_2$alkyl, $C_3$alkyl, $C_4$alkyl, $C_5$alkyl, $C_6$alkyl, $C_7$alkyl, $C_8$alkyl, $C_9$alkyl, $C_{10}$alkyl, $C_{11}$alkyl, $C_{12}$alkyl, branched $C_{3-5}$alkyl (e.g. isopropyl, isobutyl or isoamyl), substituted or unsubstituted aryl (e.g. phenyl or substituted phenyl), and substituted or unsubstituted heteroaryl (e.g. substituted or unsubstituted pyrrolyl, substituted or unsubstituted pyrazolyl, substituted or unsubstituted imidazolyl, substituted or unsubstituted oxazolyl, substituted or unsubstituted isoxazolyl, substituted or unsubstituted thiazolyl, substituted or unsubstituted indolyl, substituted or unsubstituted benzimidazolyl, substituted or unsubstituted benzthiazolyl, substituted or unsubstituted benzoxazolyl, substituted or unsubstituted benzofuranyl, substituted or unsubstituted pyridinyl, substituted or unsubstituted quinolonyl or substituted or unsubstituted isoquinolinyl).

In some embodiments of Formula (Ia), $R_1$ is Br.

In some embodiments of Formula (Ia), p is 1.

In some embodiments of Formula (Ia), p is 1 and $R_1$ is Br in the para-position to the amino group.

In some embodiments, the compound of Formula (Ia) is a compound of Formula (Ib):

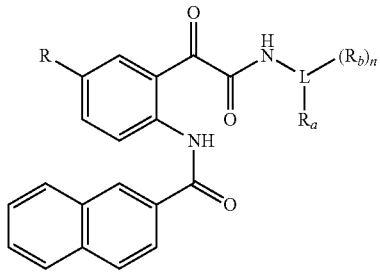

(Ib)

wherein:

L is $C_3$alkyl, $C_4$alkyl, $C_5$alkyl or $C_6$alkyl;

$R_a$ is an ammonium group, a guanidinium ($-[NH-C(=NH)(NH_3)]^+$) group or a $CH_3$-substituted guanidinium ($-[NCH_3-C(=NH)(NH_3)]^+$) group;

$R_b$, when present, is independently selected from: a guanidinium ($-[NH-C(=NH)(NH_3)]^+$) group, a $CH_3$-substituted guanidinium ($-[NCH_3-C(=NH)(NH_3)]^+$) group, triazolyl

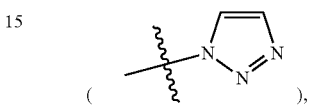

$R_e$-substituted triazolyl

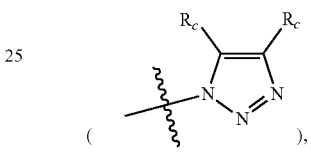

$-CONHR_c$ or $-COOR_c$, wherein each $R_c$ is independently selected from H, $C_1$alkyl, $C_2$alkyl, $C_3$alkyl, $C_4$alkyl, $C_5$alkyl, $C_6$alkyl, $C_7$alkyl, $C_8$alkyl, $C_9$alkyl, $C_{10}$alkyl, $C_{11}$alkyl, $C_{12}$alkyl, substituted or unsubstituted aryl, or substituted or unsubstituted heteroaryl; or $R_c$ is -L-$(R_a)_m$, wherein L, $R_a$ and m are as defined above and wherein L may optionally be substituted with $-CONHR_d$ or $-COOR_d$, wherein $R_d$ is a straight or branched $C_{1-12}$alkyl group;

n is 0 or 1; and

R is H, Br, Cl, F or $-CH_3$.

In some embodiments, the compound of Formula (Ib) is a compound of Formula (Ic):

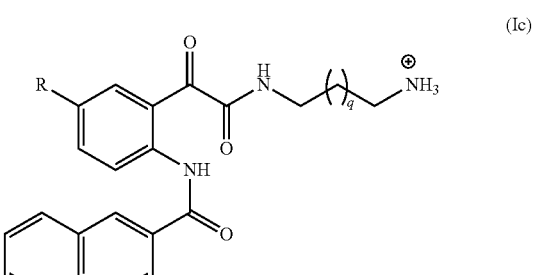

(Ic)

wherein:

q is 0 or 1; and

R is H, Br, Cl, F or $-CH_3$.

In some embodiments of Formula (Ic), q is 1.

In some embodiments of Formula (Ic), R is Br.

In some embodiments, the compound of Formula (Ic) is a compound of Formula (Ic'):

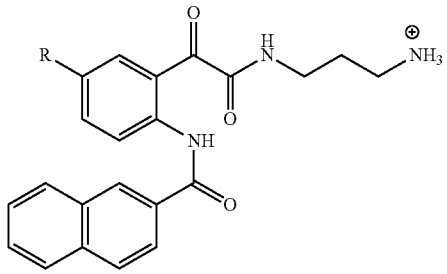
(Ic')

wherein R is H, Br, Cl, F or —CH$_3$.

In some embodiments of Formula (Ic'), R is Br.

In some embodiments, the compound of Formula (Ib) is a compound of Formula (Id) (also referred to herein as "Series-I" compounds):

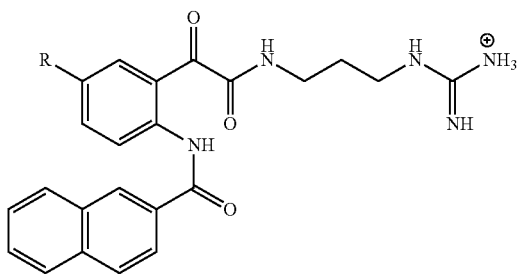
(Id)

wherein R is H, Br, Cl, F or —CH$_3$.

In some embodiments of Formula (Id), R is H.

In some embodiments of Formula (Id), R is Br. Preferably, R is Br.

In some embodiments of Formula (Id), R is Cl.

In some embodiments of Formula (Id), R is F.

In some embodiments of Formula (Id), R is —CH$_3$.

Examples of compounds of Formula (Id) include the following:

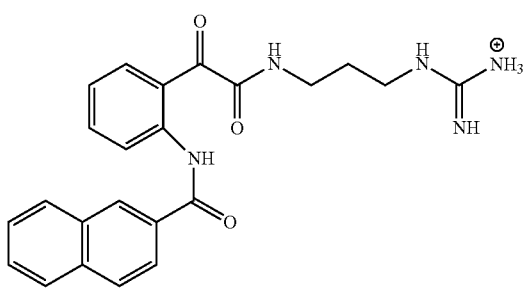

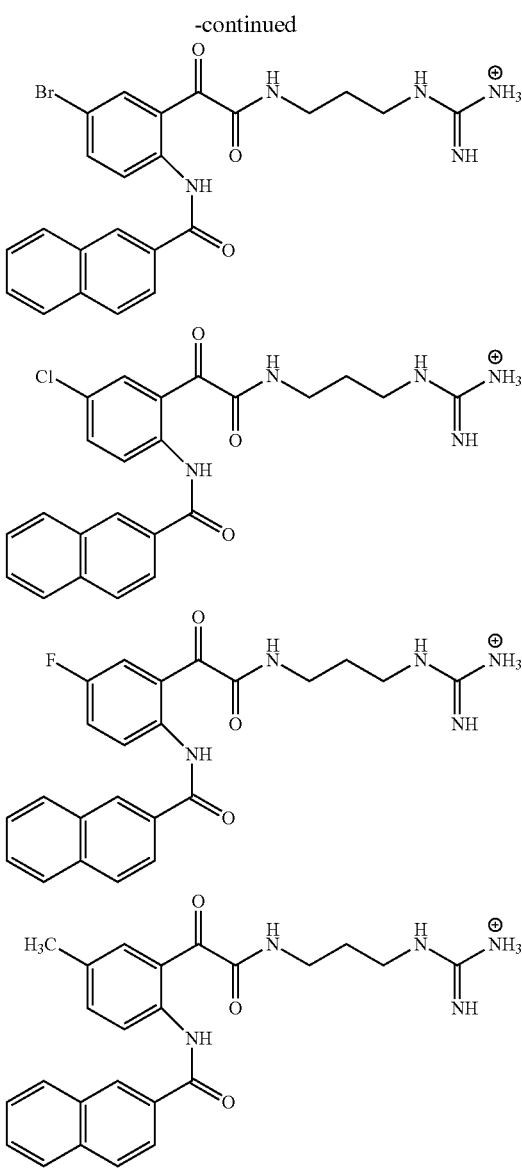

In some embodiments, the compound of Formula (Ib) is a compound of Formula (Ie) (also referred to herein as "Series-II" compounds):

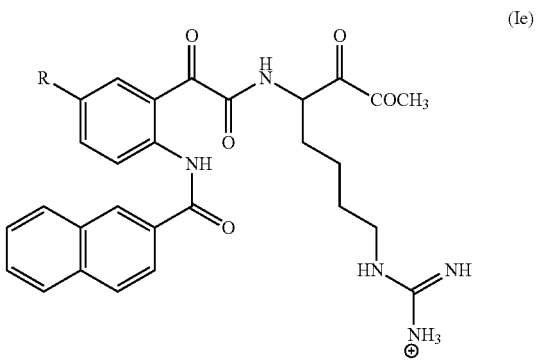
(Ie)

wherein R is H, Br, Cl, F or —CH$_3$.

In some embodiments of Formula (Ie), R is H.

In some embodiments of Formula (Ie), R is Br. Preferably, R is Br.

In some embodiments of Formula (Ie), R is Cl.

In some embodiments of Formula (Ie), R is F.

In some embodiments of Formula (Ie), R is —CH$_3$.

Examples of compounds of Formula (Ie) include the following:

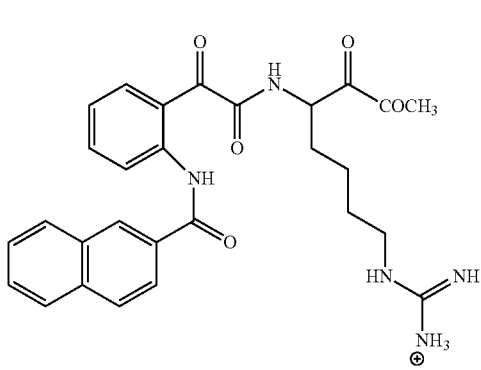

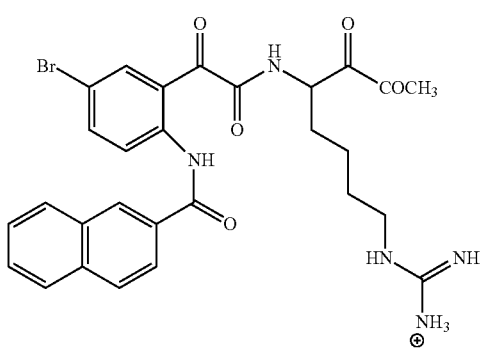

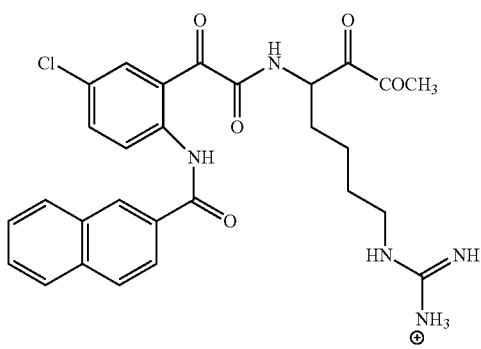

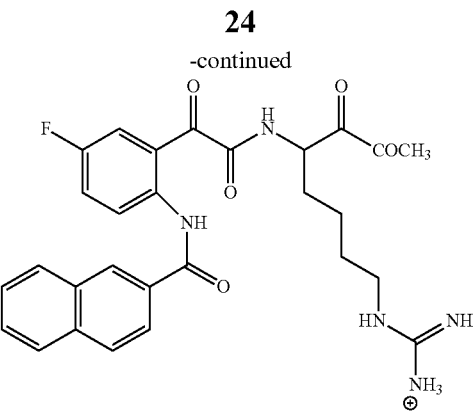

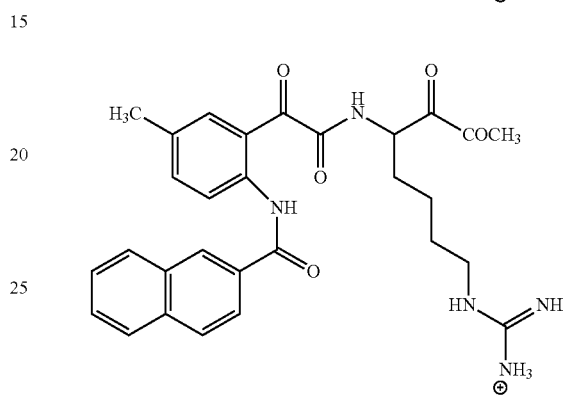

In some embodiments, the compound of Formula (Ib) is a compound of Formula (If) (also referred to herein as "Series-III" compounds):

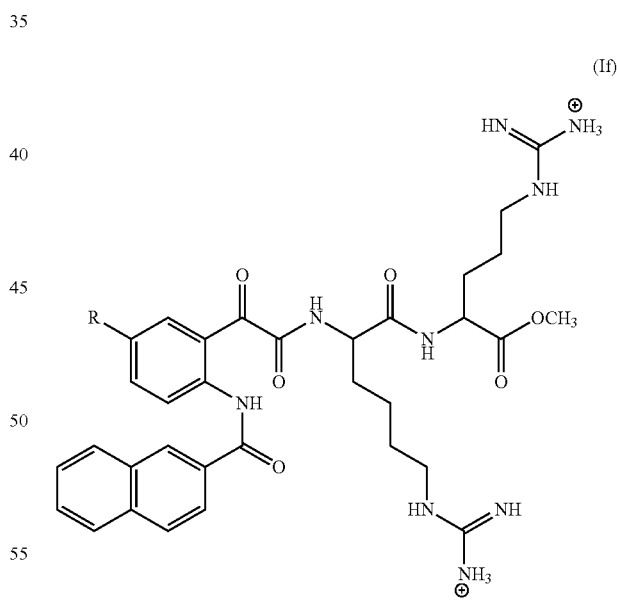

wherein R is H, Br, Cl, F or —CH$_3$.

In some embodiments of Formula (If), R is H.

In some embodiments of Formula (If), R is Br. Preferably, R is Br.

In some embodiments of Formula (If), R is Cl.

In some embodiments of Formula (If), R is F.

In some embodiments of Formula (If), R is —CH$_3$.

Examples of compounds of Formula (If) include the following:

[Chemical structure diagrams]

In some embodiments, the compound of Formula (Ib) is a compound of Formula (Ig):

(Ig)

[Chemical structure diagram]

wherein R is H, Br, Cl, F or —CH$_3$.
In some embodiments of Formula (Ig), R is H.
In some embodiments of Formula (Ig), R is Br. Preferably, R is Br.

In some embodiments of Formula (Ig), R is Cl.

In some embodiments of Formula (Ig), R is F.

In some embodiments of Formula (Ig), R is —CH₃.

Examples of compounds of Formula (Ig) include the following:

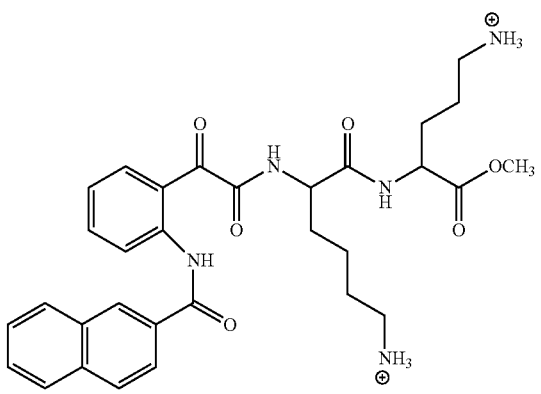

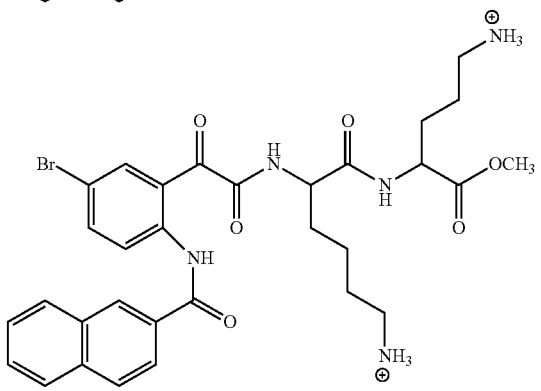

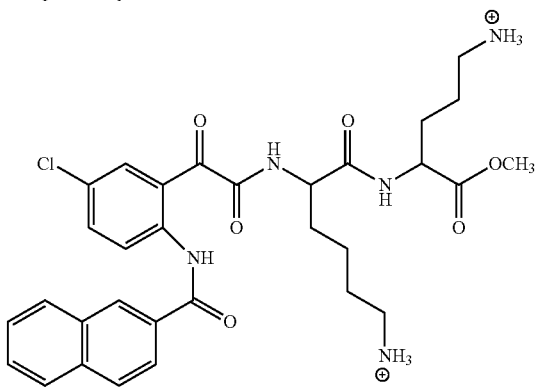

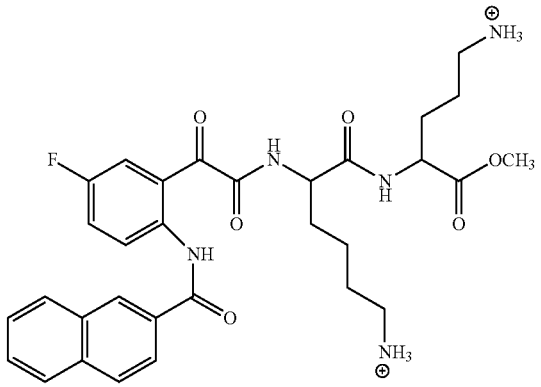

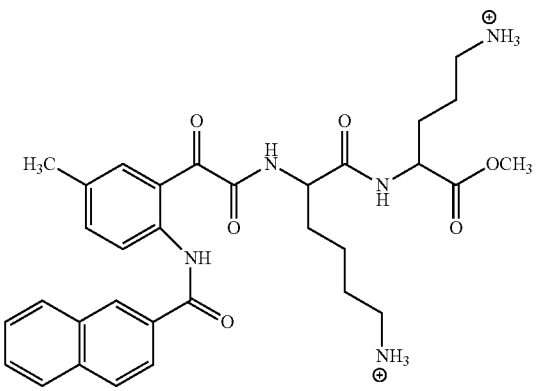 [SMILES: COC(=O)C(CCC[NH3+])NC(=O)C(CCCC[NH3+])NC(=O)C(=O)c1cc(C)ccc1NC(=O)c1ccc2ccccc2c1]

In some embodiments, the compound of Formula (I) is a compound of Formula (Ij):

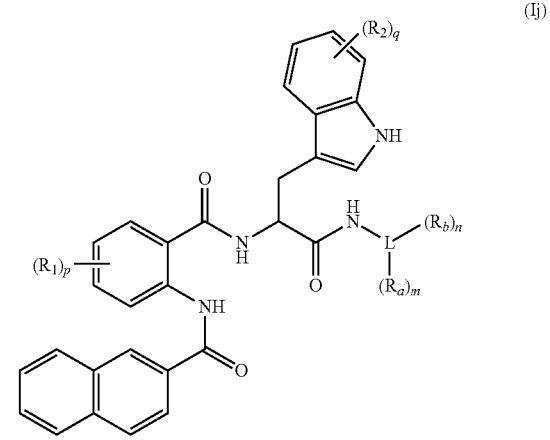

wherein L, $R_a$, m, $R_b$, n, $R_1$ and p are as defined above for Formula (I); $R_2$ is independently selected from hydroxyl, $C_{1-6}$alkyl, $C_{2-6}$alkenyl, $C_{2-6}$alkynyl, $C_{3-8}$cycloalkyl, $C_{1-6}$alkoxy, aryl$C_{1-6}$alkoxy, halo, halo$C_{1-6}$alkyl, halo$C_{1-6}$alkoxy, cyano and amino; and q is 0, 1, 2, 3 or 4.

In some embodiments of Formula (Ij), q is 1 and $R_2$ is hydroxyl, $C_1$alkyl, $C_2$alkyl, $C_3$alkyl, $C_4$alkyl, $C_5$alkyl, $C_6$alkyl, $C_1$alkoxy, $C_2$alkoxy, $C_3$alkoxy, $C_4$alkoxy, $C_5$alkoxy or $C_5$alkoxy.

Preferably, q is 0. Thus, preferably, J is

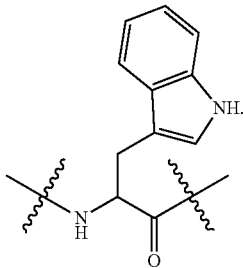 [SMILES: *NC(Cc1c[nH]c2ccccc12)C(*)=O]

In some embodiments of Formula (Ij), J is

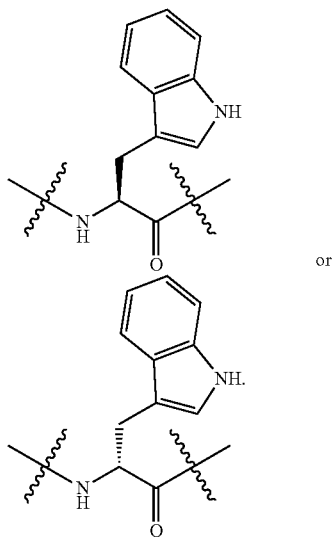

or

In some embodiments, the compound of Formula (Ij) is a compound of Formula (Ik):

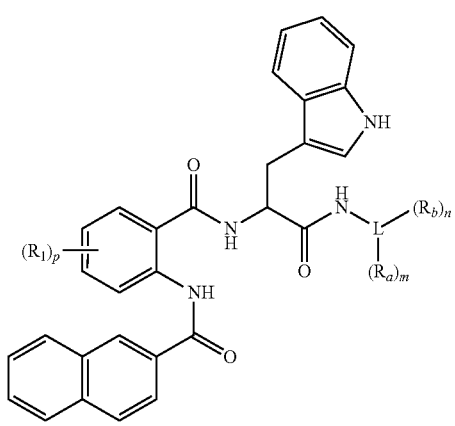

(Ik)

wherein L, $R_a$, m, $R_b$, n, $R_1$ and p are as defined above for Formula (Ij).

In some embodiments of Formula (Ik), L is $C_2$alkyl, $C_3$alkyl, $C_4$alkyl, $C_5$alkyl, $C_6$alkyl or $C_7$alkyl. Preferably, L is —$CH_2CH_2$—.

In some embodiments of Formula (Ik), $R_a$ is —$NH_2$, —$NHCH_3$, —$N(CH_3)_2$, [—$N(CH_3)_3$]$^+$, [—$NH_2(CH_3)$]$^+$, [—$NH(CH_3)_2$]$^+$, [—$N(CH_3)_3$]$^+$, a guanidine (—[NH—C(=NH)(NH$_2$)]) group, a $CH_3$-substituted guanidine (—[NCH$_3$—C(=NH)(NH$_2$)]) group, a guanidinium (—[NH—C(=NH)(NH$_3$)]$^+$) group, or a $CH_3$-substituted guanidinium (—[NCH$_3$—C(=NH)(NH$_3$)]$^+$) group. Preferably, $R_a$ is —$NH_2$, [—$NH(CH_3)_2$]$^+$, [—$N(CH_3)_3$]$^+$ or a guanidine (—[NH—C(=NH)(NH$_2$)]) group.

In some embodiments of Formula (Ik), m is 1 or 2. Preferably, m is 1.

In some embodiments of Formula (Ik), n is 0. Thus, in some embodiments of Formula (Ij), $R_b$ is not present.

In some embodiments of Formula (Ik), $R_1$ is F, Cl, Br or —$OCH_3$. Preferably, $R_1$ is F, Cl or Br. More preferably, $R_1$ is Br or F.

In some embodiments of Formula (Ik), p is 1.

In some embodiments of Formula (Ik), p is 1 and $R_1$ is F in the para-position to the amino group.

In some embodiments of Formula (Ik), p is 1 and $R_1$ is Cl in the para-position to the amino group.

In some embodiments of Formula (Ik), p is 1 and $R_1$ is Br in the para-position to the amino group.

In some embodiments of Formula (Ik), p is 1 and $R_1$ is —$OCH_3$ in the para-position to the amino group.

Examples of compounds of Formula (Ik) include the following:

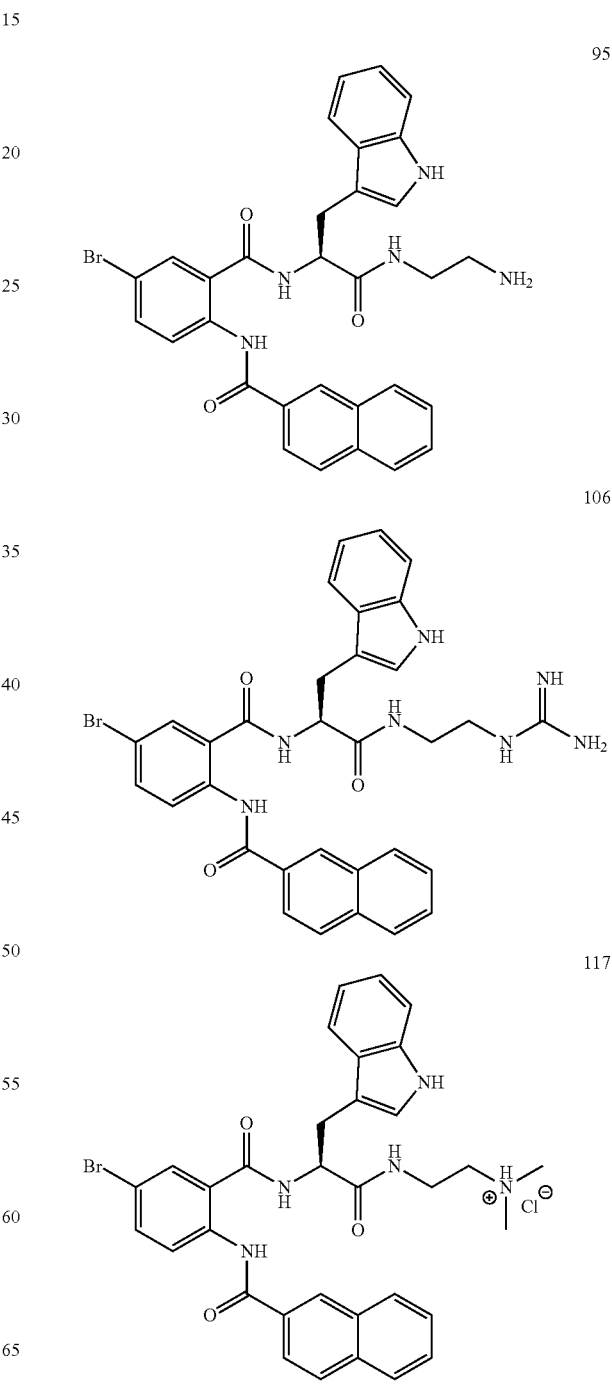

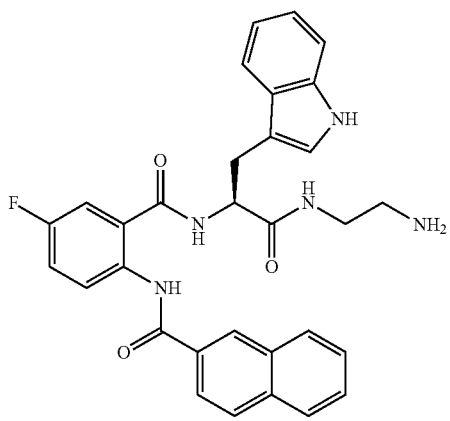

96

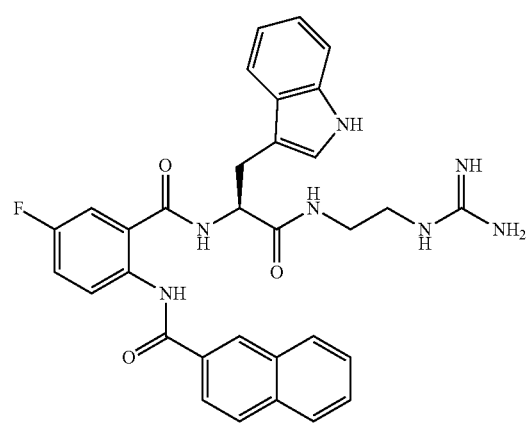

107

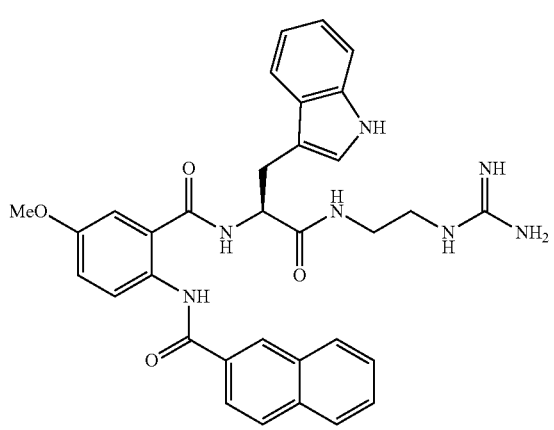

109

The compounds of Formula (I) possess antibacterial activity. The compounds of Formula (I) are small molecule mimics of natural host-defensive antimicrobial peptides. The compounds of Formula (I) can be used to treat or prevent bacterial infections. The inventors have also found that the compounds of Formula (I) can be used to inhibit the growth of planktonic cells and disrupt established biofilms, and are able to inhibit biofilm formation.

The compounds can be prepared by reactions of N-naphthoylisatins or isatoic anhydrides with amines and amino acids (e.g. ring-opening reactions). The incorporation of a guanidinium salt typically results in improved antibacterial activity compared to the corresponding quaternary ammonium salt. Thus, the replacement of quaternary ammonium salts with guanidinium salts can be an effective strategy for increasing the antibacterial activity. Further, the incorporation of additional amino acid or peptide moieties generally increases the antibacterial activity. Generally, the presence of a bromine or fluorine substituent ($R_1$ in Formula (I)) on the phenyl ring in Formula (I) improves activity.

Preparation Methods

The compounds of Formula (I) may be synthesised by methods known in the art. Various synthetic schemes are described below and in the Examples. The Examples describe the preparation of various specific compounds of Formula (I). A person skilled in the art would be able to modify the synthetic schemes described below and in the Examples to prepare other compounds of Formula (I) or salts thereof.

Compounds of the formula (Ic) and compounds of the formula (Ic') may, for example, be prepared as described in Scheme 1 (the first three steps shown in Scheme 1 form compounds of the formula (Ic').

Synthetic guanylated N-naphthoyl-phenyl glyoxamide-based peptidomimetics of Formula (Ia) were classified into 3 series (Series-I based on Formula (Id), Series-II based on Formula (Ie), and Series-III based on Formula (If), based on the number of guanidine moieties and peptide bonds present in the molecules. The design of these novel molecules centers around the replacement of the ammonium ion in Formula (Ic') with the guanidinium ion to produce Series-I compounds (Formula (Id)). By extension, the Series-II and Series-III compounds were designed by incorporating either one or two guanylated amino acids, respectively (Formula (Ie) and Formula (If)). The Series-I, Series-II, and Series-III compounds may, for example, be prepared as described in Schemes 1, 2 and 3 below.

The common starting point in the synthesis of all three series involved the N-acylation of isatins (9-13) to generate N-naphthoylisatins (14-18) (Scheme 1). This was achieved in good yields of 65-80% through the use of naphthoyl chloride and sodium hydride in DMF as previously reported (see Nizalapur, S.; Ho, K. K.; Kimyon, Ö.; Yee, E.; Berry, T.; Manefield, M.; Cranfield, C. G.; Willcox, M.; Black, D. S.; Kumar, N. *Org. Biomol. Chem.* 2016, 14, 3623).

Scheme 1: General scheme for the synthesis of Series-I guanylated glyoxamide-based peptidomimetics.

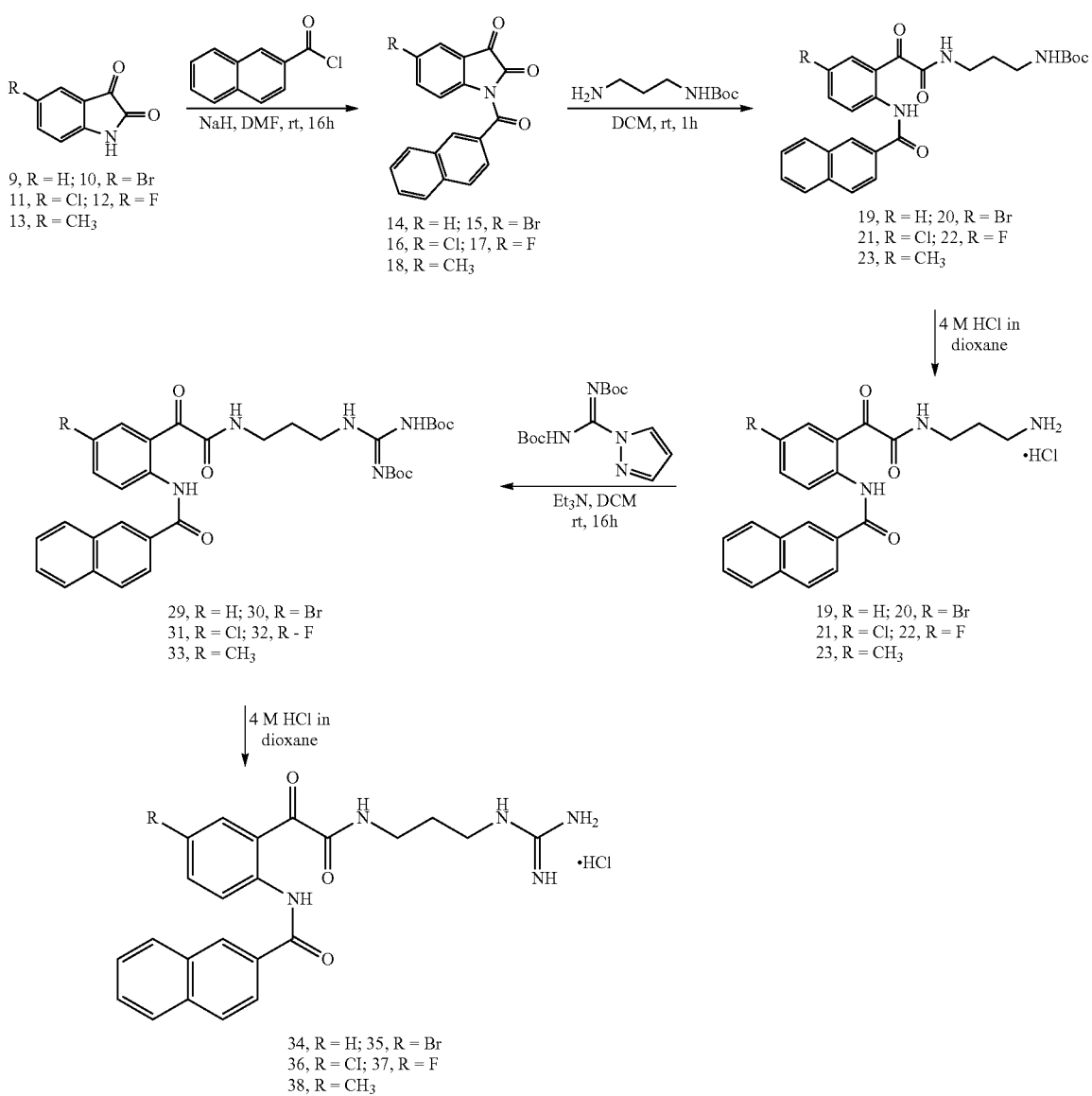

The synthesis of Series-I compounds was achieved via ring-opening reactions of N-naphthoylisatins (14-18) with tert-butyl (3-aminopropyl) carbamate in DCM over 2 h at room temperature, giving glyoxamide derivatives (19-23) in good to excellent yields (53-98%) (Scheme 1). Cleavage of the Boc protecting group was performed with 4 M HCl/dioxane in DCM at room temperature for 2 h to liberate the hydrochloride salts (24-28) in good yields (92-100%). Subsequently, these hydrochloride salts were treated with tert-butyl (E)-(((tert-butoxycarbonyl)imino)(1H-imidazol-1-yl)methyl)carbamate and Et$_3$N at room temperature in DCM for 16 h, affording the di-boc-guanidine derivatives (29-33) in moderate to good yields (58-100%). Finally, treatment of these compounds with 4 M HCl/dioxane in DCM at room temperature for 16 h yielded the guanidinium glyoxamide derivatives (34-38) in moderate to excellent yields (85%-95%).

The synthesis of the Series-II compounds commenced with the ring-opening reaction of N-naphthoylisatins (14-18) with N-Boc lysine methyl ester hydrochloride in sat. NaHCO$_3$/DCM (1:1) for 16 h, which afforded glyoxamides (39-42) in moderate yields (37-59%) (Scheme 2). Interestingly, when this reaction was performed using Et$_3$N in DCM, as described for the synthesis of glyoxamides (19-23), no product was isolated. Deprotection with 4 M HCl/dioxane in DCM gave amine hydrochlorides (43-46) in quantitative yields (95%-95%), followed by treatment with tert-butyl (E)-(((tert-butoxycarbonyl)imino)(1H-imidazol-1-yl)methyl)carbamate in DCM to obtain compounds 47-50 in 47-77% yields. Final Boc-deprotection using 4 M HCl/dioxane in DCM was achieved in 4 h, however, hydrolysis of the methyl ester was also observed and carboxylic acids 51-54 were isolated in 60%-65% yields. A selective deprotection of the Boc groups was achieved using TFA/DCM, followed by salt exchange with 4 M HCl/dioxane in Et$_2$O to obtain compounds 55-56 in 65%-85% yields.

Scheme 2: General scheme for the synthesis of Series-II guanylated glyoxamide-based peptidomimetics.

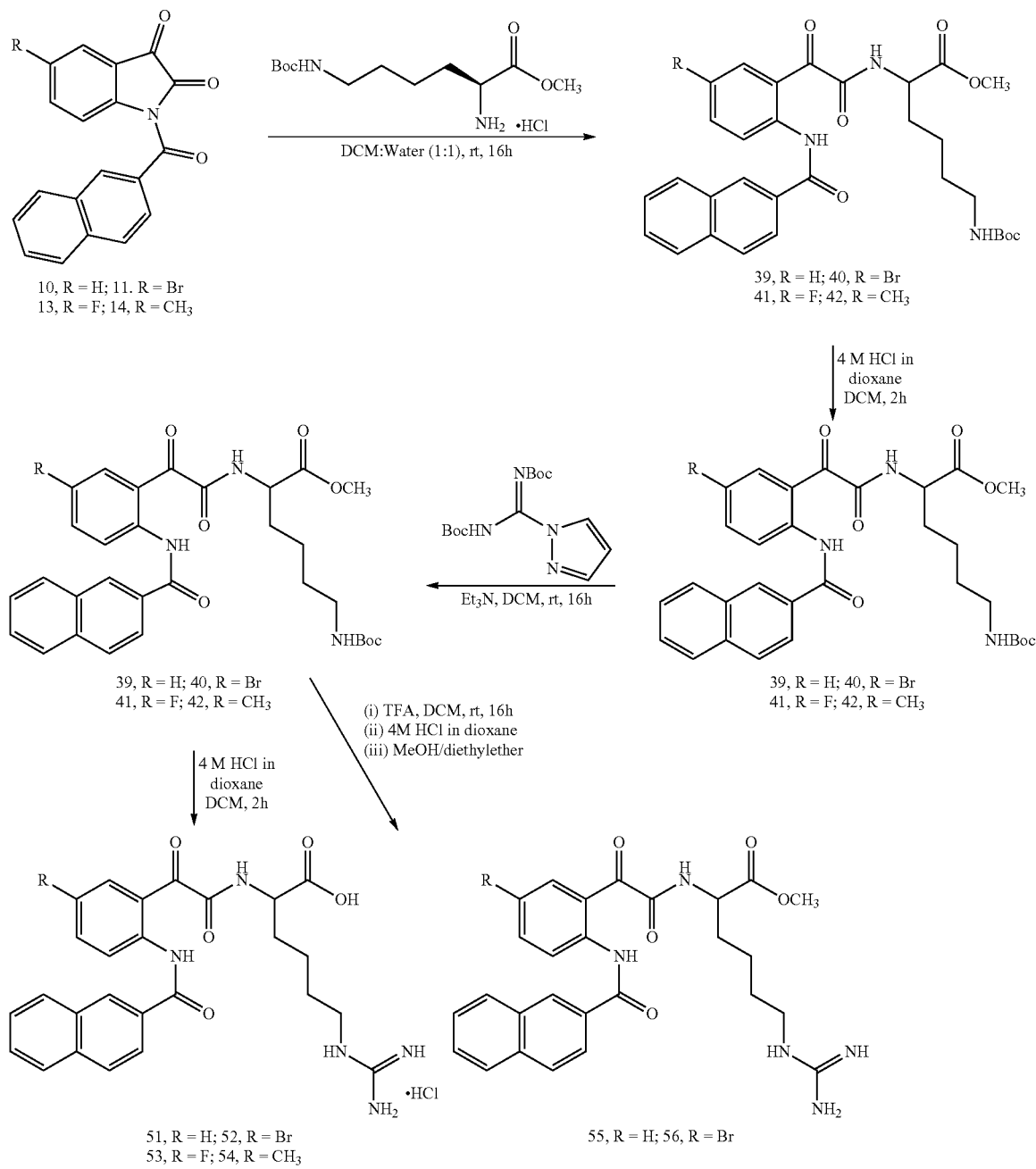

In order to synthesise the dipeptide-based compounds of Series-III, esters 38 and 39 were saponified by treatment with LiOH in a THF/MeOH/water mixture at room temperature for 16 h, giving acids 57 and 58 in 98% and 100% yield, respectively (Scheme 3). These acids were then coupled with methyl 2-amino-5-((tert-butoxycarbonyl)amino)pentanoate using EDC.HCl/HOBt and (i-Pr)$_2$NEt in acetonitrile at 0° C. to rt for 2 h, affording amides 59 and 60 in yields of 31% and 60%, respectively. The initial cooling of this reaction was found to be essential in order to avoid decomposition of the materials, which was observed at room temperature after periods of 2 h, with no product observed to form during this time. De-protection under the previously detailed conditions then gave compounds 61 and 62 in 80% and 89% yield. Subsequent reaction with tert-butyl (E)-(((tert-butoxycarbonyl)imino)(1H-imidazol-1-yl)methyl) carbamate in DCM gave compounds 63 and 64 in 51% and 65% yield, with deprotection using TFA in DCM at 0° C. for 3 h and subsequent salt exchange with 4 M HCl/dioxane in DCM afforded compounds 65 and 66 in 44% and 72% yield, respectively.

Scheme 3: General scheme for the synthesis of Series-III guanylated glyoxamide-based peptidomimetics.

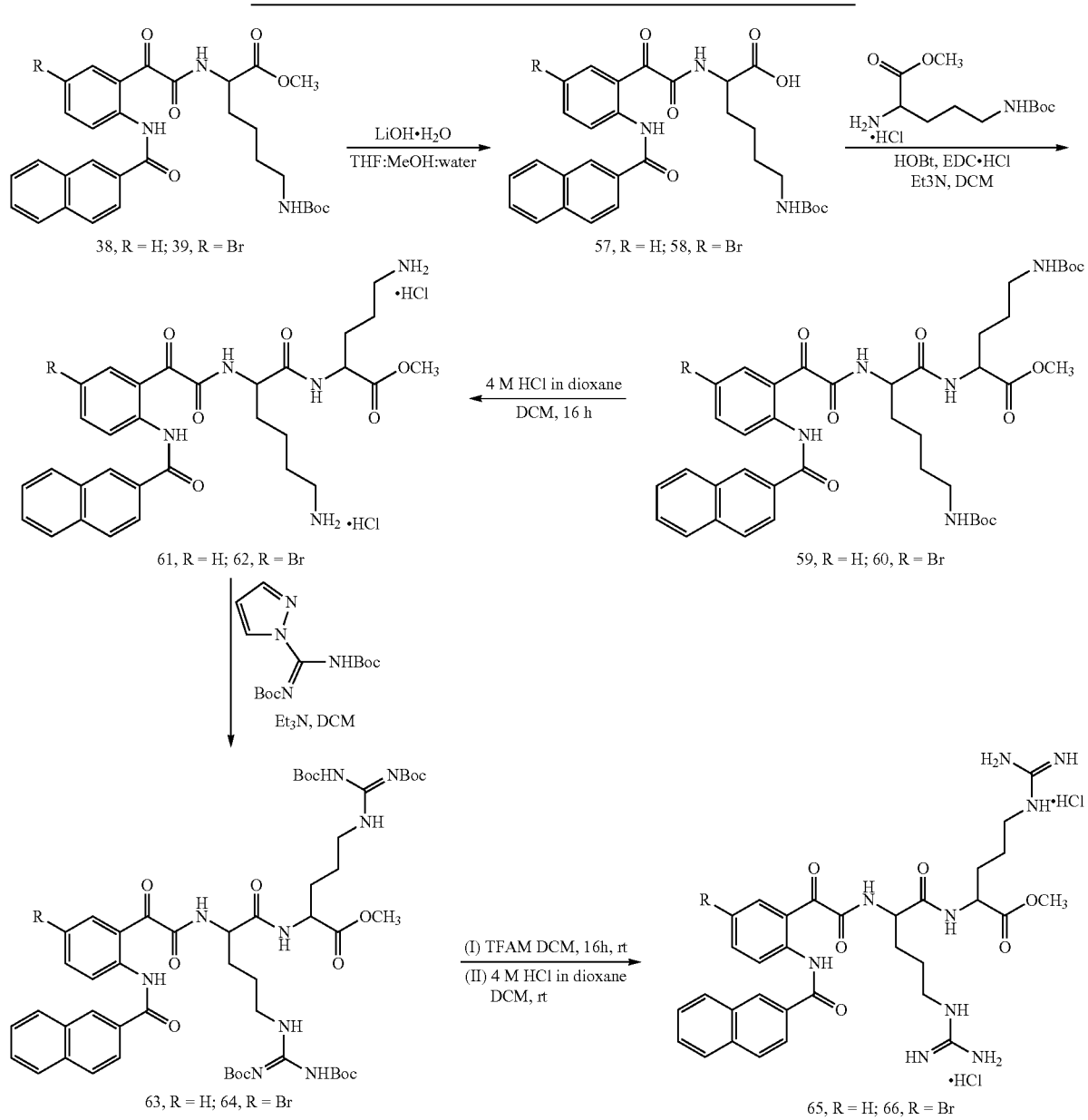

Compounds of the Formula (Ij) and compounds of the Formula (Ik) may, for example, be prepared as described in Schemes 4 and 5 described in the Examples.

For therapeutic applications, the salts of the compound of Formula (I) are preferably pharmaceutically acceptable, but it will be appreciated that non-pharmaceutically acceptable salts also fall within the scope of the present invention. Such salts are, for example, useful as intermediates in the preparation of pharmaceutically acceptable salts. Examples of pharmaceutically acceptable salts include salts of pharmaceutically acceptable cations such as sodium, potassium, lithium, calcium, magnesium, ammonium and alkylammonium; acid addition salts of pharmaceutically acceptable inorganic acids such as hydrochloric, orthophosphoric, sulphuric, phosphoric, nitric, carbonic, boric, sulfamic and hydrobromic acids; or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, trihaloacetic (e.g. trifluoroacetic), methanesulphonic, trihalomethanesulphonic, toluenesulphonic, benzenesulphonic, salicylic, sulphanilic, aspartic, glutamic, edetic, stearic, palmitic, oleic, lauric, pantothenic, tannic, ascorbic and valeric acids.

Applications

The antibacterial and/or antibiofilm activity of the compounds of Formula (I) make these compounds useful in clinical and industrial applications to treat or prevent various bacterial infections, and/or prevent or reduce biofilm formation.

Thus, the compounds of Formula (I) have a range of applications including dermal applications (e.g. in wound care and in combatting skin infections), therapeutic applications (e.g. antibiotics); attachment to a surface where biofilm formation is a problem (e.g. surfaces of implantable devices in the human or animal body); and in industrial applications where biofilm formation is a problem (e.g. in cleaning agents).

The compounds of Formula (I) may be attached to a surface on which biofilm formation is a problem or potential problem. In this regard, biofilm formation is a particular problem in circumstances where a surface comes into contact with biofilm forming bacteria. For example, in medical and veterinary applications, the surfaces of medical devices, and in particular, implantable medical devices, come into contact with microbial populations and are therefore susceptible to biofilm formation. The compounds of Formula (I) described herein are suitable for use in medical and veterinary applications, such as in implantable devices. The compounds of Formula (I) may be attached to any surface which can form a covalent bond, or which can be functionalised to form a covalent bond, between the surface and the compound. Examples of suitable surfaces include surfaces made of glass, fluorinate ethyl propylene (FEP), polycarbonate, polystyrene, polycarbonate, polystyrene, silicone, silicon, titanium, polyurethane, poly(ethylene terephthalate), or hydroxyapatite.

Examples of implantable devices include a mesh; a screw; a pin; a rod; an angioplastic plug; a plate; a tube; a dental implant; an orthopedic implant; a guided tissue matrix; an aortic aneurysm graft device; an atrioventricular shunt; a catheter; a heart valve; a hemodialysis catheter; a bone replacement device; a joint replacement device; an indwelling arterial catheter; an indwelling venous catheter; a pacemaker casing; a pacemaker lead; a stent, such as a vascular stent, a tracheal stent, an esophageal stent, a urethral stent, a rectal stent, a stent graft; a drug delivery port; a venous valve; contact lenses; and an ear implant.

The inventors also envisage that the compounds of Formula (I) described herein can be used in non-medical and veterinary applications where biofilm formation can be a problem. Examples include use in the food and pharmaceutical industry along feed lines and other areas where biofilm formation can occur.

The compounds of Formula (I) described herein may be incorporated into, or onto, any surface where inhibition of biofilm formation may be required, such as, for example, dental instruments; dentures; dental retainers; dental braces including plastic braces (such as Invisalign); bristles of toothbrushes; dental prostheses and orthodontic devices; toys, HVAC ((heating, ventilation and air conditioning)) systems; cooling towers; humidifiers; humidifier filters, hot tub filters, swimming pool filters; plastic bottles; water jugs; tap and water spout; washing machines; dishwashers; animal water dishes; bathroom tiles and fixtures; sinks; showers; shower heads; toilets; toilets lids; toilet seats; sealants and grout; dishes; cups; utensils such as forks, spoons, knives, and spatulas; bowls; food storage containers; beverage storage containers; cutting boards; dish drying trays; garbage bags; sinks; fish ponds; swimming pools; swimming pool liners; swimming pool skimmer; pond liners; bird baths; and hot tubs.

Thus, the present invention also provides the following:
a composition comprising a compound of Formula (I) and a suitable carrier, adjuvant or diluent;
a pharmaceutical composition comprising a compound of Formula (I) and a pharmaceutically acceptable carrier, adjuvant or diluent;
a method of treating or preventing a bacterial infection in a subject, the method comprising administering to the subject an effective amount of a compound of Formula (I);
a method of killing bacteria, or inhibiting the proliferation of bacteria, the method comprising contacting the bacteria with an effective amount of a compound of Formula (I);
a method of treating a surface to prevent, reduce or inhibit biofilm formation on the surface, the method comprising applying to the surface an effective amount of a compound of Formula (I);
a method of treating a surface to prevent, reduce or inhibit biofilm formation on the surface, the method comprising contacting the surface with an effective amount of a compound of Formula (I);
a method of preventing, reducing or inhibiting biofilm formation on a surface, the method comprising applying to the surface an effective amount of a compound of Formula (I);
a method of preventing, reducing or inhibiting biofilm formation on a surface, the method comprising contacting the surface with an effective amount of a compound of Formula (I); and
a method of preventing, reducing or inhibiting biofilm formation on a surface, the method comprising exposing a biofilm, or a microorganism capable of forming a biofilm, to a compound of Formula (I).

Pharmaceutical Compositions

The invention also provides a pharmaceutical composition comprising a compound of Formula (I) or a pharmaceutically acceptable salt thereof, and a pharmaceutically acceptable carrier.

In some embodiments, the compound of Formula (I) or a pharmaceutically acceptable salt thereof may be used in combination with one or more other agents.

Accordingly, in some embodiments, the pharmaceutical composition may further comprise, or be administered in combination with, one or more other agents. For example, the pharmaceutical composition may further comprise, or be administered in combination with, agents useful in treating bacterial infections.

It will be understood that the combined administration of a compound of Formula (I) or a pharmaceutically acceptable salt thereof with the one or more other agents may be concurrent, sequential or separate administration.

The compound of Formula (I) or a pharmaceutically acceptable salt thereof may also be used in combination with one of more further active agents useful in the treatment of at least one symptom of the disease or condition associated with bacterial infections.

The term "composition" encompasses formulations comprising the active ingredient with conventional carriers and excipients, and also formulations with encapsulating materials as a carrier to provide a capsule in which the active ingredient (with or without other carriers) is surrounded by the encapsulation carrier. In pharmaceutical compositions, the carrier is "pharmaceutically acceptable" meaning that it is compatible with the other ingredients of the composition and is not deleterious to a subject. The pharmaceutical compositions of the present invention may contain other agents or further active agents as described above, and may be formulated, for example, by employing conventional solid or liquid vehicles or diluents, as well as pharmaceutical additives of a type appropriate to the mode of desired administration (for example, excipients, binders, preservatives, stabilizers, flavours, etc.) according to techniques such as those well known in the art of pharmaceutical formulation (See, for example, Remington: The Science and Practice of Pharmacy, 21st Ed., 2005, Lippincott Williams & Wilkins).

The pharmaceutical composition may be suitable for oral, rectal, nasal, topical (including dermal, buccal and sublingual), vaginal or parenteral (including intramuscular, subcutaneous and intravenous) administration or in a form suitable for administration by inhalation or insufflation.

The compound of Formula (I) or a pharmaceutically acceptable salt thereof (sometimes referred to below as the "compound(s) of the invention"), together with a conventional adjuvant, carrier, or diluent, may thus be placed into the form of pharmaceutical compositions and unit dosages thereof. The pharmaceutical composition may be a solid, such as a tablet or filled capsule, or a liquid such as solution, suspension, emulsion, elixir, or capsule filled with the same, for oral administration. The pharmaceutical composition may also be in the form of suppositories for rectal administration or in the form of sterile injectable solutions for parenteral (including subcutaneous) use.

Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

For preparing pharmaceutical compositions from the compounds of the invention, pharmaceutically acceptable carriers can be either solid or liquid. Solid form preparations include powders, tablets, pills, capsules, cachets, suppositories, and dispensable granules. A solid carrier can be one or more substances which may also act as diluents, flavouring agents, solubilisers, lubricants, suspending agents, binders, preservatives, tablet disintegrating agents, or an encapsulating material.

Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Tablets, powders, capsules, pills, cachets, and lozenges can be used as solid forms suitable for oral administration.

Liquid form preparations include solutions, suspensions, and emulsions, for example, water or water-propylene glycol solutions. For example, parenteral injection liquid preparations can be formulated as solutions in aqueous polyethylene glycol solution.

Sterile liquid form compositions include sterile solutions, suspensions, emulsions, syrups and elixirs. The active ingredient can be dissolved or suspended in a pharmaceutically acceptable carrier, such as sterile water, sterile organic solvent or a mixture of both.

The pharmaceutical compositions according to the present invention may thus be formulated for parenteral administration (e. g. by injection, for example bolus injection or continuous infusion) and may be presented in unit dose form in ampoules, pre-filled syringes, small volume infusion or in multi-dose containers with an added preservative. The pharmaceutical compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

Pharmaceutical forms suitable for injectable use include sterile injectable solutions or dispersions, and sterile powders for the extemporaneous preparation of sterile injectable solutions. They should be stable under the conditions of manufacture and storage and may be preserved against oxidation and the contaminating action of microorganisms such as bacteria or fungi.

The solvent or dispersion medium for the injectable solution or dispersion may contain any of the conventional solvent or carrier systems for injectable solutions or dispersions, and may contain, for example, water, ethanol, polyol (for example, glycerol, propylene glycol and liquid polyethylene glycol, and the like), suitable mixtures thereof, and vegetable oils.

Pharmaceutical forms suitable for injectable use may be delivered by any appropriate route including intravenous, intramuscular, intracerebral, intrathecal, epidural injection or infusion.

Sterile injectable solutions are prepared by incorporating the active ingredient in the required amount in the appropriate solvent with various other ingredients such as those enumerated above, as required, followed by filtered sterilization. Generally, dispersions are prepared by incorporating the various sterilised active ingredient into a sterile vehicle which contains the basic dispersion medium and the required other ingredients from those enumerated above. In the case of sterile powders for the preparation of sterile injectable solutions, preferred methods of preparation are vacuum drying or freeze-drying of a previously sterile-filtered solution of the active ingredient plus any additional desired ingredients.

The compounds of the invention may be formulated into compositions suitable for oral administration, for example, with an inert diluent or with an assimilable edible carrier, or enclosed in hard or soft shell gelatin capsule, or compressed into tablets, or incorporated directly with the food of the diet. For oral therapeutic administration, the active compound may be incorporated with excipients and used in the form of ingestible tablets, buccal tablets, troches, capsules, elixirs, suspensions, syrups, wafers, and the like.

The amount of active compound in therapeutically useful compositions should be sufficient that a suitable dosage will be obtained.

The tablets, troches, pills, capsules and the like may also contain the components as listed hereafter: a binder such as gum, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier.

Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active ingredient(s) may be incorporated into sustained-release preparations and formulations, including those that allow specific delivery of the active ingredient to specific regions of the gut.

Aqueous solutions suitable for oral use can be prepared by dissolving the active component in water and adding suitable colorants, flavours, stabilising and thickening agents, as desired. Aqueous suspensions suitable for oral use can be made by dispersing the finely divided active component in water with viscous material, such as natural or synthetic gums, resins, methylcellulose, sodium carboxymethylcellulose, or other well-known suspending agents.

Pharmaceutically acceptable carriers include any and all pharmaceutically acceptable solvents, dispersion media, coatings, antibacterial and antifungal agents, isotonic and absorption delaying agents and the like.

Also included are solid form preparations that are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilising agents, and the like.

For topical administration to the epidermis, the compounds of the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions for nasal administration may be applied directly to the nasal cavity by conventional means, for example with a dropper, pipette or spray. The formulations may be provided in single or multidose form. In the case of a dropper or pipette, this may be achieved by the patient administering an appropriate, predetermined volume of the solution or suspension. In the case of a spray, this may be achieved for example by means of a metering atomising spray pump. To improve nasal delivery and retention the compounds of the invention may be encapsulated with cyclodextrins, or formulated with other agents expected to enhance delivery and retention in the nasal mucosa.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas.

The aerosol may conveniently also contain a surfactant such as lecithin. The dose of the active ingredient may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g. gelatin, or blister packs from which the powder may be administered by means of an inhaler.

In formulations intended for administration to the respiratory tract, including intranasal formulations, the active ingredient will generally have a small particle size for example of the order of 5 to 10 microns or less. Such a particle size may be obtained by means known in the art, for example by micronisation.

When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

It is especially advantageous to formulate parenteral compositions in dosage unit form for ease of administration and uniformity of dosage. Parental compositions may be in the form of physically discrete units suited as unitary dosages for the subjects to be treated, each unit containing a predetermined quantity of the active ingredient calculated to produce the desired therapeutic effect in association a pharmaceutical carrier.

The compounds may also be administered in the absence of carrier where the compounds are in unit dosage form.

Compositions comprising compounds of the invention formulated for oral delivery either alone or in combination with another agent are particularly preferred.

As such, in one embodiment there is provided a pharmaceutical composition for oral administration comprising a compound of Formula (I), or a pharmaceutically acceptable salt thereof, a pharmaceutically acceptable carrier and optionally another agent or further active agent. In one embodiment, the pharmaceutical composition is orally administered in an effective amount to a subject in need of treatment for a bacterial infection or disease, for example a human subject infected by *S. aureus* or *E. coli*.

The invention also provides use of a compound of Formula (I) or a pharmaceutically acceptable salt thereof in the manufacture of a medicament for the treatment or prevention of a disease or condition associated with bacterial infections.

Dosages

The term "effective amount" refers to the amount of a compound effective to achieve the desired response, for example, to treat or prevent a bacterial infection, or to prevent, reduce or inhibit biofilm formation on a surface.

An appropriate dosage level of a compound of Formula (I), or a pharmaceutically acceptable salt thereof, administered to a subject to treat or prevent a bacterial infection will generally be about 0.01 to 500 mg per kg subject body weight per day which can be administered in single or multiple doses.

It will be understood that the specific dose level and frequency of dosage for any particular subject may be varied and will depend upon a variety of factors including the activity of the specific compound employed, the metabolic stability and length of action of that compound, the age, body weight, general health, sex and diet of the subject, the mode and time of administration, rate of excretion, drug combinations, and the severity of the particular condition.

Suitable dosages of the compound of Formula (I) or further active agents administered in combination with compound of Formula (I) can be readily determined by a person skilled in the art having regard to the particular compound of Formula (I) or further active agent selected.

It will further be understood that when the compounds of the invention are to be administered in combination with one or more agents, or other active agents, the dosage forms and levels may be formulated for either concurrent, sequential or separate administration or a combination thereof.

EXAMPLES

The present invention is further described below by reference to the following non-limiting Examples.

Materials and Methods

All chemical reagents were purchased from commercial sources (Alfa-Aesar and Sigma Aldrich) and used without further purification. Solvents were commercial and used as obtained. Reactions were performed using oven-dried glassware under an atmosphere of nitrogen and in anhydrous conditions (as required). Room temperature refers to the ambient temperature. Yields refer to chromatographically and spectroscopically pure compounds unless otherwise stated. Reactions were monitored by thin layer chromatography (TLC) precoated with Merck silica gel 60 $F_{254}$. The quenching of short or long wavelength UV fluorescence performed visualization. Flash chromatography was carried out using Grace Davison LC60A 6-μm silica gel. Infrared spectra were recorded using a Cary 630 ATR spectrophotometer. High-resolution mass spectrometry was performed by the Bioanalytical Mass Spectrometry facility, UNSW. Melting points were obtained using a Mel-Temp melting point apparatus and are uncorrected. Proton and Carbon NMR spectra were recorded in the solvents specified using a Bruker DPX 300 or a Bruker Avance 300 spectrometer as designated. Chemical shifts (δ) are quoted in parts per million (ppm), to the nearest 0.01 ppm and internally referenced relative to the solvent nuclei. $^1$HNMR spectral data are reported as follows: [chemical shift in ppm; multiplicity in br, broad; s, singlet; d, doublet; t, triplet; q, quartet; quint, quintet; sext, sextet; sept, septet; m, multiplet; or as a combination of these (e.g. dd, dt etc.)]; coupling constant (J) in hertz, integration, proton count and assignment.

Example 1

All the naphthoylisatins (14-18) were synthesized by using a previously reported procedure (see Nizalapur, S.; Ho, K. K.; Kimyon, Ö.; Yee, E.; Berry, T.; Manefield, M.; Cranfield, C. G.; Willcox, M.; Black, D. S.; Kumar, N. *Org. Biomol. Chem.* 2016, 14, 3623).

General Procedure A for Synthesis of Compounds 19-23

To a solution of naphthoylisatins (14-18) 1.0 mmol in dichloromethane was added tert-butyl (3-aminopropyl)carbamate (1.0 mmol) at room temperature and stirring continued for 1 h. After completion, water was added to the reaction mixture and extracted with dichloromethane. The organic layer was separated and dried over sodium sulfate, filtered and evaporated under reduced pressure to yield the product.

Tert-butyl (3-(2-(2-(2-naphthamido)phenyl)-2-oxoacetamido)propyl)carbamate (19)

The title compound 19 was prepared from compound 14 (250 mg, 0.830 mmol) and tert-butyl (3-aminopropyl)carbamate (1.0 mmol) according to the general procedure A. The product 19 was obtained as a yellow solid (210 mg, 53%); $^1$HNMR (CDCl$_3$, 300 MHz): δ 11.56 (bs, 1H), 8.81 (t, J=5.93 Hz, 1H), 8.61-8.58 (m, 1H), 8.32 (d, J=8.30 Hz, 1H), 8.17-8.09 (m, 2H), 8.08-7.98 (m, 2H), 7.88-7.60 (m, 4H), 7.40-7.28 (m, 1H), 6.87-6.70 (m, 1H), 3.17 (q, J=6.61 Hz, 2H), 2.92 (q, J=6.24 Hz, 2H), 1.63-1.47 (m, 2H), 1.37 (s, 9H); $^{13}$CNMR (CDCl$_3$, 100 MHz): δ 192.7, 166.0, 163.6, 156.6, 142.7, 136.8, 135.0, 134.6, 132.7, 131.7, 129.3, 128.7, 128.4, 128.1, 127.7, 126.8, 123.6, 122.7, 120.8, 118.8, 79.6, 37.2, 36.3, 30.1, 28.3; HRMS (ESI): m/z calcd for C$_{28}$H$_{31}$N$_2$NaO$_5$ [M+H+Na]$^+$ 497.1997, found 498.1999.

Tert-butyl (3-(2-(2-(2-naphthamido)-5-bromophenyl)-2-oxoacetamido)propyl)carbamate (20)

The title compound 20 was prepared from compound 15 (250 mg, 0.659 mmol) and tert-butyl (3-aminopropyl)carbamate (1.0 mmol) according to the general procedure A. The product 20 was obtained as a yellow solid (350 mg, 97%); $^1$HNMR (CDCl$_3$, 300 MHz): δ 12.09 (bs, 1H), 8.91 (t, J=9.15 Hz, 1H), 8.69-8.51 (m, 2H), 8.13-7.87 (m, 4H), 7.79 (m, J=2.40, 9.10 Hz, 1H), 7.74-7.49 (m, 3H), 4.96-4.77 (m, 1H), 3.52 (q, J=6.14 Hz, 2H), 3.28 (q, J=6.14 Hz, 2H), 1.87-1.73 (m, 2H), 1.46 (s, 9H); $^{13}$CNMR (CDCl$_3$, 100 MHz): δ 191.7, 165.9, 162.70, 156.8, 141.6, 139.3, 136.7, 135.1, 132.6, 131.4, 129.3, 128.8, 128.2, 127.7, 126.9, 123.5, 122.5, 120.4, 115.1, 79.4, 37.1, 36.4, 30.0, 28.3. HRMS (ESI): m/z calcd for C$_{27}$H$_{28}$BrN$_3$NaO$_5$ [M+Na]$^+$ 576.1100, found 576.1105.

Tert-butyl (3-(2-(2-(2-naphthamido)-5-chlorophenyl)-2-oxoacetamido)propyl)carbamate (21)

The title compound 21 was prepared from compound 16 (250 mg, 0.675 mmol) and tert-butyl (3-aminopropyl)carbamate (1.0 mmol) according to the general procedure A. The product 21 was obtained as a yellow solid (320 mg, 87%); $^1$HNMR (CDCl$_3$, 300 MHz): δ 11.2 (bs, 1H), 8.83-8.69 (m, 1H), 8.57 (bs, 1H), 8.18-7.90 (m, 5H), 7.85-7.58 (m, 4H), 6.83-6.60 (m, 1H), 3.20-3.04 (m, 2H), 2.95-2.77 (m, 2H), 1.58-1.43 (m, 2H), 1.36 (s, 9H); $^{13}$CNMR (DMSO-d$_6$, 75 MHz): δ 193.4, 165.7, 164.4, 156.2, 137.5, 135.8, 134.9, 133.5, 132.7, 132.6, 131.8, 129.5, 128.9, 128.6, 128.4, 128.1, 127.5, 124.1, 123.6, 122.3, 77.9, 37.8, 36.9, 29.5, 28.7; HRMS (ESI): m/z calcd for C$_{27}$H$_{28}$ClN$_3$NaO$_5$ [M+Na]$^+$ 532.1608, found 532.1610.

Tert-butyl (3-(2-(2-(2-naphthamido)-5-fluorophenyl)-2-oxoacetamido)propyl)carbamate (22)

The title compound 22 was prepared from compound 17 (250 mg, 0.806 mmol) and tert-butyl (3-aminopropyl)carbamate (1.0 mmol) according to the general procedure A. The product 22 was obtained as a yellow solid (250 mg, 75%); $^1$HNMR (CDCl$_3$, 300 MHz): δ 12.0 (bs, 1H), 9.06-8.90 (m, 1H), 8.62-8.52 (m, 1H), 8.36-8.20 (m, 1H), 8.16-7.85 (m, 4H), 7.81-7.53 (m, 3H), 7.49-7.38 (m, 1H), 5.06-4.66 (m, 1H), 3.51 (q, J=6.29 Hz, 2H), 3.27 (q, J=5.88 Hz, 2H), 1.85-1.71 (m, 2H), 1.46 (s, 9H); $^{13}$CNMR (CDCl$_3$, 75 MHz): δ 191.2, 165.9, 162.7, 156.7, 139.0, 135.1, 132.7, 131.5, 129.4, 128.8, 128.4, 128.1, 127.8, 126.8, 124.0, 123.7, 123.5, 122.7, 120.4, 120.1, 79.7, 37.2, 36.3, 30.0, 28.3; HRMS (ESI): m/z calcd for C$_{27}$H$_{28}$FN$_3$NaO$_5$ [M+Na]$^+$ 516.1902, found 516.1905.

Tert-butyl (3-(2-(2-(2-naphthamido)-5-methylphenyl)-2-oxoacetamido)propyl)carbamate (23)

The title compound 23 was prepared from compound 18 (250 mg, 0.793 mmol) and tert-butyl (3-aminopropyl)carbamate (1.0 mmol) according to the general procedure A. The product 23 was obtained as a yellow solid (350 mg, 90%); $^1$HNMR (CDCl$_3$, 300 MHz): δ 11.5 (bs, 1H), 8.77 (t, J=5.71 Hz, H), 8.63-8.53 (m, 1H), 8.25-7.95 (m, 5H), 7.73-7.51 (m, 4H), 6.88-6.68 (m, 1H), 3.16 (q, J=6.75 Hz, 2H), 2.91 (q, J=6.75 Hz, 2H), 2.37 (s, 3H), 1.61-1.46 (m, 2H), 1.37 (s, 9H); $^{13}$CNMR (CDCl$_3$, 75 MHz): δ 193.3, 165.7, 164.4, 156.0, 137.5, 135.8, 134.9, 133.5, 132.7, 132.6, 131.8, 129.5, 128.9, 128.6, 128.4, 128.2, 127.5, 124.1, 123.6, 122.3, 55.5, 37.8, 36.6, 29.6, 28.7, 20.7; HRMS (ESI): m/z calcd for C$_{28}$H$_{31}$N$_3$NaO$_5$ [M+Na]$^+$ 512.2151, found 512.2156.

General Procedure B for the Synthesis of Compounds 24 to 28

To a solution of 19-23 (1 mmol) in dichloromethane was added HCl in dioxane (4M solution) (5.0 equiv) at 0° C. The reaction mixture was warmed to room temperature and stirred for 16 h. After completion of the reaction, solvent was removed under reduced pressure and treated with diethylether and compound was dried under high vacuum to yield the product.

N-(2-(2-((3-Aminopropyl)amino)-2-oxoacetyl)phenyl)-2-naphthamide hydrochloride (24)

The title compound 24 was prepared from compound 19 (190 mg, 0.399 mmol) and HCl in dioxane (4M solution) according to the general procedure B. The product was obtained as yellowish solid. $^1$HNMR (CDCl$_3$, 300 MHz): δ 11.5 (bs, 1H), 9.08-8.91 (m, 1H), 8.61 (s, 1H), 8.26 (d, J=8.32 Hz, 1H), 8.18-7.92 (m, 7H), 7.88-7.59 (m, 4H), 7.34 (t, J=7.51 Hz, 1H), 3.26 (q, J=6.55 Hz, 2H), 2.91-2.67 (m, 2H), 1.87-1.70 (m, 2H); $^{13}$CNMR (CDCl$_3$, 75 MHz): δ 192.6, 165.8, 164.4, 139.6, 135.1, 134.9, 132.6, 132.6, 131.7, 129.5, 129.0, 128.7, 128.6, 128.2, 127.6, 124.1, 123.9, 122.3, 37.0, 36.2, 27.3; HRMS (ESI): m/z calcd for C$_{18}$H$_{28}$N$_3$O$_3$ [M+H]+ 334.2121, found 334.2125.

N-(2-(2-((3-Aminopropyl)amino)-2-oxoacetyl)-4-bromophenyl)-2-naphthamide hydrochloride (25)

The title compound 25 was prepared from compound 20 (150 mg, 0.271 mmol) and HCl in dioxane (4M solution) according to the general procedure B. The product was obtained as yellowish solid (132 mg, 100%); $^1$HNMR (CDCl$_3$, 300 MHz): δ 11.2 (bs, 1H), 8.93 (t, J=5.89 Hz, 1H), 8.61-8.55 (m, 1H), 8.14-8.07 (m, 2H), 8.06-7.95 (m, 2H), 7.91-7.83 (m, 3H), 7.83-7.61 (m, 5H), 3.21 (q, J=6.43 Hz, 2H), 2.84-2.0 (m, 2H), 1.79-1.66 (m, 2H); $^{13}$CNMR (DMSO-d$_6$, 75 MHz): δ 188.8, 165.9, 162.7, 137.3, 136.3, 134.9, 133.4, 132.5, 131.3, 129.5, 128.8, 128.7, 128.7, 128.4, 128.2, 127.5, 125.2, 124.3, 116.1, 36.9, 36.2, 27.2; HRMS (ESI): m/z calcd for C$_{22}$H$_{21}$BrClN$_3$NaO$_3$ [M+Na]$^+$ 456.0735, found 456.0740.

N-(2-(2-((3-Aminopropyl)amino)-2-oxoacetyl)-4-chlorophenyl)-2-naphthamide hydrochloride (26)

The title compound 26 was prepared from compound 21 (95 mg, 0.174 mmol) and HCl in dioxane (4M solution) according to the general procedure B. The product was obtained as yellowish solid (80 mg, 95%); $^1$HNMR (CDCl$_3$, 300 MHz): δ 11.2 (bs, 1H), 8.93 (t, J=5.83 Hz, 1H), 8.62-8.54 (m, 1H), 8.17-7.88 (m, 6H), 7.85-7.57 (m, 7H), 3.20 (q, J=6.51 Hz, 2H), 2.86-2.68 (m, 2H), 1.82-1.64 (m, 2H); $^{13}$CNMR (DMSO-d$_6$, 75 MHz): δ 188.8, 166.0, 162.7, 136.8, 136.4, 136.0, 135.0, 133.4, 132.5, 131.3, 130.5, 129.5, 128.8, 128.7, 128.3, 128.2, 127.5, 125.2, 124.3, 116.1, 36.9, 36.2, 27.2; HRMS (ESI): m/z calcd for C$_{22}$H$_{21}$ClN$_3$O$_3$[M+H]$^+$ 410.1264, found 410.1266.

N-(2-(2-((3-Aminopropyl)amino)-2-oxoacetyl)-4-fluorophenyl)-2-naphthamide hydrochloride (27)

The title compound 27 was prepared from compound 22 (100 mg, 0.202 mmol) and HCl in dioxane (4M solution) according to the general procedure B. The product was obtained as yellowish solid (85 mg, 97%); $^1$HNMR (CDCl$_3$, 300 MHz): δ 11.1 (bs, 1H), 8.93 (t, J=5.98 Hz, 1H), 8.63-8.56 (m, 1H), 8.17-7.82 (m, 8H), 7.73-0.51 (m, 4H), 3.19 (q, J=6.4 Hz, 2H), 2.82-2.67 (m, 2H), 1.80-1.64 (m, 2H); $^{13}$CNMR (CDCl$_3$, 75 MHz): δ 189.0, 165.9, 162.9, 134.9, 134.3, 132.5, 131.4, 129.5, 128.7, 128.7, 128.6, 128.2, 127.5, 125.6, 124.4, 120.7, 120.4, 117.5, 117.2, 36.9, 36.2, 27.2; HRMS (ESI): m/z calcd for C$_{22}$H$_{21}$FN$_3$O$_3$ [M+H]$^+$ 394.1555, found 394.1561.

N-(2-(2-((3-Aminopropyl)amino)-2-oxoacetyl)-4-methylphenyl)-2-naphthamide hydrochloride (28)

The title compound 28 was prepared from compound 23 (350 mg, 0.715 mmol) and HCl in dioxane (4M solution) according to the general procedure B. The product was obtained as grey sticky solid (280 mg, 92%). $^1$HNMR (CDCl$_3$, 300 MHz): δ 11.4 (bs, 1H), 8.95 (t, J=5.95, 1H), 8.61-8.55 (m, 1H), 8.18-7.80 (m, 9H), 7.72-7.62 (m, 2H), 7.61-7.52 (m, 2H), 3.24 (q, J=6.46 Hz, 2H), 2.84-2.71 (m, 2H), 2.37 (s, 3H), 1.82-1.68 (m, 2H); $^{13}$CNMR (CDCl$_3$, 75 MHz): δ 192.5, 165.7, 164.4, 137.1, 135.5, 134.9, 133.5, 132.6, 132.3, 131.8, 129.5, 128.9, 128.6, 128.5, 128.2, 127.5, 124.2, 124.1, 122.6, 37.0, 36.2, 27.3, 20.7; HRMS (ESI): m/z calcd for C$_{23}$H$_{24}$N$_3$O$_3$ [M+H]$^+$ 390.1808, found 390.1812.

General Procedure C for the Synthesis of Compounds 29 to 33

A solution of 24-28 (1 equiv), N,N'-di-Boc-1H-pyrazole-1-carboxamidine (1.05 equiv) and triethylamine (1.00 equiva) in dichloromethane was stirred at room temperature for 3 hours. After completion of reaction, the solvent was removed under reduced pressure to get the crude product, which was purified by flash chromatography. The compounds were eluted in 25-30% ethyl acetate in hexane.

(Z)—N-(2-(2-((3-(2,3-dibocguanidino)propyl)amino)-2-oxoacetyl)phenyl)-2-naphthamide (29)

The title compound was prepared from 24 (100 mg, 0.242 mmol), N,N'-di-Boc-1H-pyrazole-1-carboxamidine (79 mg, 0.255 mmol) and triethylamine (0.025 mL, 0.255 mmol) according to the general procedure C. The product was obtained as yellowish liquid (149 mg, 100%); $^1$HNMR (CDCl$_3$, 300 MHz): δ 12.3 (bs, 1H), 11.4 (bs, 1H), 9.07-8.98 (m, 1H), 8.75-8.57 (m, 2H), 8.55-8.40 (m, 1H), 823-8.17 (dd, J=1.45, 8.04 Hz, 1H), 8.16-8.10 (m, 1H), 8.09-7.89 (m, 3H), 7.76-7.67 (m, 1H), 7.67-7.55 (m, 2H), 7.26-7.7 (m, 1H), 3.73-3.5 (m, 4H), 1.95-1.80 (m, 2H), 1.50 (s 9H), 1.28 (s, 9H); $^{13}$CNMR (CDCl$_3$, 75 MHz): δ 194.1, 166.1, 164.6, 157.0, 153.1, 142.7, 136.6, 135.0, 134.5, 132.7, 131.7, 129.4, 128.7, 128.5, 128.0, 127.7, 126.8, 123.6, 122.7, 120.8, 118.6, 115.2, 83.9, 79.5, 37.6, 35.6, 29.8, 28.0, 27.9; HRMS (ESI): m/z calcd for $C_{33}H_{39}N_5NaO_7$ [M+Na]$^+$ 640.2739, found 640.2742.

(Z)—N-(2-(2-((3-(2,3-dibocguanidino)propyl)amino)-2-oxoacetyl)4-bromo phenyl)-2-naphthamide (30)

The title compound was prepared from 25 (100 mg, 0.205 mmol), N,N'-di-Boc-1H-pyrazole-1-carboxamidine (76 mg, 0.246 mmol) and triethylamine (0.024 mL, 0.246 mmol) according to the general procedure C. The product was obtained as colorless liquid (130 mg, 91.5%); $^1$HNMR (CDCl$_3$, 300 MHz): δ 12.1 (bs, 1H), 11.4 (bs, 1H), 8.95 (d, J=9.09 Hz, 1H), 8.65-8.50 (m, 6H), 8.36 (d, J=2.42 Hz, 1H), 8.11-7.97 (m, 3H), 7.96-7.90 (m, 1H), 7.80 (dd, J=2.40, 9.11 Hz, 1H), 7.68-7.55 (m, 2H), 3.64-3.56 (m, 2H), 3.55-3.47 (m, 2H), 1.94-1.80 (m, 2H), 1.36 (m, 9H), 1.28 (s, 9H); $^{13}$CNMR (CDCl$_3$, 100 MHz): δ 192.8, 166.0, 163.7, 162.9, 157.3, 153.2, 141.6, 139.2, 136.5, 135.1, 1327, 131.3, 129.4, 128.8, 128.6, 128.2, 127.7, 126.9, 122.5, 120.2, 115.1, 83.6, 79.4, 37.2, 35.7, 31.2, 29.9, 28.0, 27.9; HRMS (ESI): m/z calcd for $C_{33}H_{39}BrN_5O_7$ [M+H]$^+$ 698.1999, found 698.2007.

(Z)—N-(2-(2-((3-(2,3-dibocguanidino)propyl)amino)-2-oxoacetyl)4-chloro phenyl)-2-naphthamide (31)

The title compound was prepared from 26 (70 mg, 0.145 mmol), N,N'-di-Boc-1H-pyrazole-1-carboxamidine (52 mg, 0.174 mmol) and triethylamine (0.024 mL, 0.174 mmol) according to the general procedure C. The compound was obtained as grey sticky solid (55 mg, 58%); $^1$HNMR (CDCl$_3$, 300 MHz): δ 12.1 (bs, 1H), 11.4 (bs, 1H), 9.01 (d, J=9.18 Hz, 1H), 8.69-8.48 (m, 3H), 8.23 (d, J=2.45 Hz, 1H), 813-7.90 (m, 4H), 7.72-7.52 (m, 3H), 3.67-3.43 (m, 4H), 1.93-1.79 (m, 2H), 1.51 (s, 9H), 1.27 (s, 9H); $^{13}$CNMR (CDCl$_3$, 75 MHz): δ 192.9, 166.0, 163.7, 157.3, 153.2, 141.6, 139.2, 136.5, 135.1, 132.7, 131.4, 129.4, 129.0, 128.8, 128.6, 128.1, 127.7, 127.6, 126.9, 123.5, 122.3, 119.8, 83.6, 79.4, 37.2, 35.7, 29.9, 28.0, 27.9; HRMS (ESI): m/z calcd for $C_{33}H_{38}ClN_5NaO_7$ [M+H]$^+$ 674.2354, found 674.2352.

(Z)—N-(2-(2-((3-(2,3-dibocguanidino)propyl)amino)-2-oxoacetyl)4-fluoro phenyl)-2-naphthamide (32)

The title compound was prepared from 27 (70 mg, 0.162 mmol), N,N'-di-Boc-1H-pyrazole-1-carboxamidine (58 mg, 0.195 mmol) and triethylamine (0.027 mL, 0.195 mmol) according to the general procedure C. The compound was obtained as colorless liquid (85 mg, 82%); $^1$HNMR (CDCl$_3$, 300 MHz): δ 12.1 (bs, 1H), 11.4 (bs, 1H), 9.07-8.98 (m, 1H), 8.68-8.485 (m, 3H), 8.18-8.46 (m, 5H), 7.68-7.54 (m, 2H), 7.51-7.37 (m, 1H), 3.67-3.40 (m, 4H), 1.93-1.78 (m, 2H), 1.51 (s, 9H), 1.28 (s, 9H); $^{13}$CNMR (CDCl$_3$, 75 MHz): δ 192.6, 165.9, 163.7, 162.8, 158.9, 155.6, 153.1, 139.0, 135.1, 132.7, 131.5, 129.3, 128.8, 128.5, 128.1, 127.7, 126.8, 123.6, 123.5, 122.8, 122.6, 120.2, 119.9, 119.8, 119.7, 83.6, 79.4, 37.2, 35.7, 29.9, 28.0, 27.9; HRMS (ESI): m/z calcd $C_{33}H_{39}FN_5O_7$ [M+H]$^+$ 636.2823, found 636.2828.

(Z)—N-(2-(2-((3-(2,3-dibocguanidino)propyl)amino)-2-oxoacetyl)4-methyl phenyl)-2-naphthamide (33)

The title compound was prepared from 28 (220 mg, 0.517 mmol), N,N'-di-Boc-1H-pyrazole-1-carboxamidine (176 mg, 0.568 mmol) and triethylamine (0.079 mL, 0.568 mmol) according to the general procedure C. The compound was obtained as yellowish solid (180 mg, 55%); $^1$HNMR (CDCl$_3$, 300 MHz): δ 12.1 (bs, 1H), 11.4 (bs, 1H), 9.20 (bs, 1H), 8.87 (d, J=8.65 Hz, 1H), 8.63-8.47 (m, 2H), 8.14-8.01 (m, 2H), 8.00-7.94 (m, 2H), 7.93-7.88 (m, 1H), 7.70-7.38 (m, 4H), 3.97-3.77 (m, 2H), 3.66-3.46 (m, 2H), 2.38 (s, 3H), 2.05-1.92 (m, 2H), 1.51 (s, 9H), 1.38 (s, 9H); $^{13}$CNMR (CDCl$_3$, 75 MHz): δ 193.7, 165.9, 164.9, 155.3, 142.6, 152.5, 140.3, 137.4, 135.0, 134.3, 132.7, 132.3, 131.8, 129.4, 128.6, 128.4, 127.9, 127.7, 126.7, 123.6, 120.8, 118.8, 36.0, 29.3, 27.9, 27.8, 20.7; HRMS (ESI): m/z calcd for $C_{34}H_{41}N_5NaO_7$ [M+Na]$^+$ 654.2893, found 654.2898.

General Procedure D for the Synthesis of Compounds 34 to 38

To a solution of 29-33 (1 mmol) in dichloromethane was added HCl in dioxane (4M solution) (10.0 equiv) at 0° C. The reaction mixture was warmed to room temperature and stirred for 16 h. After completion of reaction, solvent was removed under reduced pressure and treated with diethylether, and dried to yield the product.

N-(2-(2-((3-Guanidinopropyl)amino)-2-oxoacetyl)phenyl)-2-naphthamide hydrochloride (34)

The title compound 34 was prepared from compound 29 (140 mg, 0.213 mmol) and HCl in dioxane (4M solution) according to the general procedure D. The product was obtained as a colorless solid (80 mg, 78%); $^1$HNMR (CDCl$_3$, 300 MHz): δ 11.5 (bs, 1H), 9.03-8.80 (m, 1H), 8.60 (bs, 1H), 8.38-7.93 (m, 5H), 7.89-7.53 (m, 5H), 7.48-6.78 (m, 5H), 3.29-2.99 (m, 4H), 1.81-1.53 (m, 2H); $^{13}$CNMR (CDCl$_3$, 150 MHz): δ 192.8, 165.9, 164.4, 157.3, 139.7, 135.1, 134.9, 132.7, 132.6, 131.7, 129.5, 129.0, 128.7, 128.6, 128.2, 127.6, 124.0, 124.1, 123.9, 122.3, 36.4, 28.7, 15.5; HRMS (ESI): m/z calcd for $C_{23}H_{24}N_5O_3$ [M+H]$^+$ 418.1873, found 418.1874.

N-(4-Bromo-2-(2-((3-guanidinopropyl)amino)-2-oxoacetyl)phenyl)-2-naphthamide hydrochloride (35)

The title compound 35 was prepared from compound 30 (100 mg, 0.143 mmol) and HCl in dioxane (4M solution) according to the general procedure D. The product obtained as a yellowish solid (60 mg, 79%); $^1$HNMR (CDCl$_3$, 300 MHz): δ 11.2 (bs, 1H), 9.00-8.80 (m, 1H), 8.58 (s, 1H), 8.18-7.94 (m, 4H), 7.88 (s, 3H), 7.78-7.59 (m, 2H), 7.58-7.43 (m, 1H), 7.41-6.58 (m, 4H), 3.25-2.98 (m, 4H), 1.70-1.51 (m, 2H); $^{13}$CNMR (CDCl$_3$, 150 MHz): δ 188.9, 166.1, 162.8, 159.6, 157.1, 137.3, 136.3, 135.0, 133.4, 132.4, 131.3, 129.4, 128.8, 128.7, 128.5, 128.2, 127.6, 125.3, 124.3, 116.3, 38.6, 36.4, 28.6; HRMS (ESI): m/z calcd for $C_{23}H_{23}BrN_5O_3$ [M+H]$^+$ 498.0975, found 496.0979.

N-(4-Chloro-2-(2-((3-guanidinopropyl)amino)-2-oxoacetyl)phenyl)-2-naphthamide hydrochloride (36)

The title compound 36 was prepared from compound 31 (45 mg, 0.069 mmol) and HCl in dioxane (4M solution) according to the general procedure D. The product was obtained as a yellowish solid (25 mg, 75%); $^1$HNMR (CDCl$_3$, 300 MHz): δ 11.2 (bs, 1H), 8.88 (t, J=5.89 Hz, 1H), 8.60-8.56 (m, 1H), 8.15-7.90 (m, 5H), 7.81-7.73 (m, 2H), 7.72-7.61 (m, 2H), 7.54-7.45 (m, 1H), 7.42-6.59 (m, 4H), 3.25-2.98 (m, 4H), 1.70-1.51 (m, 2H); $^{13}$CNMR (CDCl$_3$, 150 MHz): δ 189.0, 166.1, 162.8, 157.1, 146.2, 136.9, 135.0, 133.4, 132.4, 131.3, 130.6, 129.4, 128.8, 128.7, 128.4, 128.3, 127.6, 126.1, 125.1, 124.3, 38.6, 36.4, 28.6; HRMS (ESI): m/z calcd for $C_{23}H_{23}ClN_5O_3[M+H]^+$ 452.1483, found 452.1484.

N-(4-Fluoro-2-(2-((3-guanidinopropyl)amino)-2-oxoacetyl)phenyl)-2-naphthamide hydrochloride (37)

The title compound 38 was prepared from compound 32 (75 mg, 0.118 mmol) and HCl in dioxane (4M solution) according to the general procedure D. The product was obtained as a white solid (40 mg, 72%); $^1$HNMR (CDCl$_3$, 300 MHz): δ 11.1 (bs, 1H), 8.94-8.79 (m, 1H), 8.58 (s, 1H), 8.15-7.95 (m, 4H), 7.94-7.81 (m, 1H), 7.74-7.44 (m, 5H), 7.39-6.62 (m, 4H), 3.25-2.98 (m, 4H), 1.70-1.48 (m, 2H); $^{13}$CNMR (CDCl$_3$, 150 MHz): δ 189.1, 166.1, 162.9, 159.3, 157.7, 157.1, 134.9, 134.3, 132.5, 131.4, 129.4, 128.8, 128.6, 128.2, 127.5, 125.8, 125.7, 124.3, 120.7, 120.5, 119.0, 117.4, 117.3, 38.6, 36.4, 28.6; HRMS (ESI): m/z calcd for $C_{23}H_{23}FN_5O_3$ $[M+H]^+$ 436.1776, found 436.1779.

N-(2-(2-((3-Guanidinopropyl)amino)-2-oxoacetyl)-4-methylphenyl)-2-naphthamide hydrochloride (38)

The title compound 38 was prepared from compound 33 (55 mg, 0.087 mmol) and HCl in dioxane (4M solution) according to the general procedure D. The product was obtained as grey solid (35 mg, 87%); $^1$HNMR (CDCl$_3$, 300 MHz): δ 11.4 (s, 1H), 8.99-8.78 (m, 1H), 8.58 (bs, 1H), 8.18-7.93 (m, 5H), 7.74-7.51 (m, 5H), 7.48-6.78 (m, 4H), 3.26-3.15 (m, 2H), 3.14-3.05 (m, 2H), 2.37 (s, 3H), 1.74-1.56 (m, 2H); $^{13}$CNMR (CDCl$_3$, 150 MHz): δ 192.6, 165.8, 164.4, 157.2, 137.1, 135.5, 134.9, 133.6, 132.6, 132.4, 132.3, 131.8, 129.5, 128.9, 128.6, 128.5, 128.2, 127.6, 124.1, 122.6, 118.8, 39.7, 36.3, 28.7, 20.7; HRMS (ESI): m/z calcd for $C_{24}H_{26}N_5O_3[M+H]^+$ 432.2033, found 432.2030.

General Procedure E for the Synthesis of Compounds 39 to 42

A solution of compounds (10, 11, 12 and 14) (1 mmol) and methyl $N^6$-(tert-butoxycarbonyl)-D-lysinate hydrochloride (1 mmol) in dichloromethane and saturated sodium bicarbonate solution was stirred for 5 hours at room temperature. After completion of the reaction, the mixture was diluted with DCM and washed with water and dried over anhydrous sodium sulfate, filtered the solvent was removed in vacuo and the residue was purified by flash chromatography on silica gel, eluting with 30% ethyl acetate in hexane to yield the product.

Methyl $N^2$-(2-(2-(2-naphthamido)phenyl)-2-oxoacetyl)-$N^6$-(tert-butoxycarbonyl)lysinate (39)

The title compound 39 was prepared from compound 10 (200 mg, 0.664 mmol) and $N^6$-(tert-butoxycarbonyl)-D-lysinate hydrochloride (236 mg, 0.797 mmol) in dichloromethane (20 mL) and saturated sodium bicarbonate solution (20 mL) according to the general procedure E. The product was obtained as yellowish solid (160 mg, 43%); $^1$HNMR (CDCl$_3$, 400 MHz): δ 12.2 (s, 1H), 9.02-8.97 (m, 1H), 8.58 (bs, 1H), 8.50-8.40 (m, 1H), 8.10 (dd, J=1.80, 8.64 Hz, 1H), 8.07-8.02 (m, 1H), 8.00-7.96 (m, 1H), 7.94-7.89 (m, 1H), 7.75-7.67 (m, 1H), 7.65-7.55 (m, 1H), 7.24-7.17 (m, 1H), 4.77-4.66 (m, 1H), 4.59 (bs, 1H), 3.83 (s, 3H), 3.23-3.03 (m, 2H), 2.07-1.84 (m, 2H), 1.60-1.44 (m, 4H), 1.37 (s, 9H); $^{13}$CNMR (CDCl$_3$, 100 MHz): δ 192.7, 171.8, 166.0, 163.0, 156.2, 142.8, 137.0, 135.1, 134.8, 132.7, 131.6, 129.4, 128.8, 128.5, 128.3, 128.1, 127.7, 126.8, 123.5, 122.8, 120.7, 118.6, 79.2, 52.7, 52.3, 39.8, 31.4, 29.7, 28.3, 22.3; HRMS (ESI): m/z calcd for $C_{31}H_{35}N_3O_7$ $[M+H]+$ 562.2547, found 532.2548.

Methyl $N^2$-(2-(2-(2-naphthamido)-5-bromophenyl)-2-oxoacetyl)-$N^6$-(tert-butoxycarbonyl) lysinate (40)

The title compound 40 was prepared from compound 11 (280 mg, 0.738 mmol) and $N^6$-(tert-butoxycarbonyl)-D-lysinate hydrochloride (219 mg, 0.738 mmol) in dichloromethane (20 mL) and saturated sodium bicarbonate solution (20 mL) according to the general procedure E. The product was obtained as yellowish solid (281 mg, 59%); $^1$HNMR (CDCl$_3$, 300 MHz): δ 12.0 (s, 1H), 8.87 (d, J=9.05 Hz, 1H), 8.61 (d, J=9.05 Hz, 1H), 8.55-8.50 (m, 1H), 8.09-7.84 (m, 4H), 7.82-7.68 (m, 2H), 7.66-7.51 (m, 2H), 4.78-4.68 (m, 1H), 4.60 (bs, 1H), 3.84 (s, 3H), 3.26-3.03 (m, 2H), 2.12-1.84 (m, 4H), 1.63-1.44 (m, 4H), 1.38 (s, 9H); $^{13}$CNMR (CDCl$_3$, 75 MHz): δ 190.7, 171.7, 165.9, 162.3, 156.2, 141.7, 139.5, 136.8, 135.1, 132.6, 131.1, 129.4, 128.8, 128.5, 128.2, 127.7, 126.9, 123.3, 122.4, 120.0, 115.2, 79.2, 60.3, 52.7, 52.4, 31.4, 29.7, 28.3, 22.3; HRMS (ESI): m/z calcd for $C_{31}H_{34}BrN_3NaO_7$ $[M+Na]^+$ 662.1470, found 662.1472.

Methyl $N^2$-(2-(2-(2-naphthamido)-5-fluorophenyl)-2-oxoacetyl)-$N^6$-(tert-butoxycarbonyl) lysinate (41)

The title compound 41 was prepared from compound 13 (250 mg, 0.783 mmol) and $N^6$-(tert-butoxycarbonyl)-D-lysinate hydrochloride (255 mg, 0.862 mmol) in dichloromethane (20 mL) and saturated sodium bicarbonate solution (20 mL) according to the general procedure E. The product was obtained as colorless liquid (210 mg, 46%); $^1$HNMR (CDCl$_3$, 400 MHz): δ 12.0 (s, 1H), 9.00-8.91 (m, 1H), 8.53 (s, 1H), 826 (dd, J=2.96, 9.42 Hz, 1H), 8.07-7.98 (m, 2H), 7.97-7.92 (m, 1H), 7.91-7.86 (m, 1H), 7.72 (d, J=7.73 Hz, 1H), 7.65-7.53 (m, 2H), 7.45-7.38 (m, 1H), 4.74-4.66 (m, 1H), 4.61 (bs, 1H), 3.84 (s, 3H), 3.21-3.04 (m, 2H), 2.08-1.87 (m, 2H), 1.60-1.42 (m, 4H), 1.38 (s, 9H); $^{13}$CNMR (CDCl$_3$, 75 MHz): δ 190.5, 171.7, 165.9, 162.3, 158.3, 156.2, 155.9, 139.1, 135.9, 132.6, 131.3, 129.3, 128.8, 128.4, 128.2, 127.7, 126.9, 124.2, 124.0, 123.4, 122.7, 122.6, 120.5, 120.2, 119.7, 119.6, 52.7, 52.4, 40.1, 31.4, 29.7, 28.3, 22.3; HRMS (ESI): m/z calcd for $C_{31}H_{34}FN_3NaO_7$ $[M+Na]^+$ 602.2272, found 602.2273.

Methyl $N^2$-(2-(2-(2-naphthamido)-5-methylphenyl)-2-oxoacetyl)-$N^6$-(tert-butoxycarbonyl) lysinate (42)

The title compound 42 was prepared from compound 14 (250 mg, 0.792 mmol) and $N^6$-(tert-butoxycarbonyl)-D-lysinate hydrochloride (235 mg, 0.792 mmol) in dichloromethane (20 mL) and saturated sodium bicarbonate solution (20 mL) according to the general procedure E. The product was obtained as yellowish sticky solid (170 mg, 37%); $^1$HNMR (CDCl$_3$, 300 MHz): δ 12.0 (bs, 1H), 8.85 (d, J=8.59 Hz, 1H), 8.61 (d, J=9.05 Hz, 1H), 8.57-8.51 (m, 1H), 8.24-8.14 (m, 1H), 8.11-7.85 (m, 4H), 7.71-7.43 (m, 4H), 4.81-4.68 (m, 1H), 4.66-4.53 (m, 1H), 3.84 (s, 3H), 2.18-1.81 (m, 2H), 1.67-1.41 (m, 6H), 1.38 (s, 9H); $^{13}$CNMR (CDCl$_3$, 75 MHz): δ 192.1, 171.8, 165.9, 163.3, 156.1, 140.4, 137.8, 135.0, 134.6, 132.7, 132.4, 131.6, 129.3, 128.7, 128.4, 128.0, 127.7, 126.8, 123.5, 120.7, 118.6, 79.2, 52.6, 52.3, 39.8, 31.5, 29.7, 28.3, 22.4, 20.7; HRMS (ESI): m/z calcd for $C_{32}H_{37}N_3NaO_7$ [M+Na]$^+$ 598.2526, found 598.2524.

General Procedure F for the Synthesis of Compounds 43 to 46

To a solution of 39-42 (1 mmol) in dichloromethane was added HCl in dioxane (4M solution) (5.0 equiv) at 0° C. The reaction mixture was warmed to room temperature and stirred for 16 h. After completion of reaction, excess solvent was removed under reduced pressure, treated with diethylether, and dried to yield the product.

Methyl (2-(2-(2-naphthamido)phenyl)-2-oxoacetyl) lysinate hydrochloride (43)

The title compound 43 was prepared from compound 39 (160 mg, 0.282 mmol) and HCl in dioxane (4M solution) according to the general procedure F. The product was obtained as grey sticky solid (114 mg, 86%); $^1$HNMR (DMSO-d$_6$, 400 MHz): δ 11.8 (bs, 1H), 9.35 (d, J=7.25 Hz, 1H), 8.77-8.58 (m, 1H), 8.52 (d, J=8.53 Hz, 1H), 8.17-8.10 (m, 2H), 8.09-8.00 (m, 4H), 7.93-7.86 (m, 1H), 7.84-7.76 (m, 1H), 7.73-7.63 (m, 2H), 7.37 (t, J=7.79 Hz, 2H), 4.41-4.27 (m, 1H), 3.68 (s, 3H), 2.80-2.63 (m, 2H), 1.88-1.64 (m, 3H), 1.62-1.46 (m, 3H); $^{13}$CNMR (CDCl$_3$, 150 MHz): δ 193.7, 172.1, 170.3, 165.7, 165.2, 140.7, 136.0, 135.0, 133.5, 132.6, 131.7, 129.6, 129.1, 128.7, 128.6, 128.2, 127.6, 124.0, 128.3, 121.7, 52.6, 52.4, 38.7, 30.2, 26.8, 22.7; HRMS (ESI): m/z calcd for $C_{26}H_{28}N_3O_5$ [M+H]$^+$ 462.2025, found 462.2023.

Methyl (2-(2-(2-naphthamido)-5-bromophenyl)-2-oxoacetyl) lysinate hydrochloride (44)

The title compound 44 was prepared from compound 40 (100 mg, 0.37 mmol) and HCl in dioxane (4M solution) according to the general procedure F. The product was obtained as a grey sticky solid (84 mg, 100%); $^1$HNMR (CDCl$_3$, 300 MHz): δ 11.6-11.5 (m, 1H), 9.38-9.12 (m, 1H), 8.67-8.56 (m, 1H), 8.39-8.20 (m, 1H), 8.17-8.09 (m, 2H), 8.08-7.79 (m, 7H), 7.76-7.57 (m, 2H), 4.40-4.17 (m, 1H), 3.57 (s, 3H), 2.82-2.61 (m, 2H), 1.85-1.64 (m, 2H), 1.60-1.44 (m, 2H), 1.41-1.22 (m, 2H); $^{13}$CNMR (DMSO-d6, 150 MHz): δ 190.7, 173.1, 171.9, 165.8, 164.0, 139.2, 138.9, 137.7, 135.0, 132.5, 131.4, 129.5, 129.0, 128.8, 128.2, 127.6, 125.4, 124.7, 124.1, 115.8, 52.6, 52.4, 39.1, 30.1, 26.8, 22.7; HRMS (ESI): m/z calcd for $C_{26}H_{27}BrN_3O_5$ [M+H]+ 540.1125, found 540.1129.

Methyl (2-(2-(2-naphthamido)-5-fluorophenyl)-2-oxoacetyl)lysinate hydrochloride (45)

The title compound 45 was prepared from compound 41 (160 mg, 0.276 mmol) and HCl in dioxane (4M solution) according to the general procedure F. The product was obtained as grey sticky solid (80 mg, 60%); $^1$HNMR (CDCl$_3$, 300 MHz): δ 11.3 (s, 1H), 9.26 (d, J=7.11 Hz, 1H), 8.60 (s, 1H), 8.32-7.96 (m, 5H), 7.92-7.55 (m, 7H), 4.40-4.15 (m, 1H), 3.62 (s, 3H), 2.78-2.60 (m, 2H), 1.85-1.61 (m, 2H), 1.58-1.40 (m, 2H), 1.38-1.16 (m, 2H); $^{13}$CNMR (DMSO-d$_6$, 150 MHz): δ 192.5, 174.2, 168.1, 166.1, 159.5, 138.0, 134.7, 133.7, 131.8, 131.7, 131.3, 131.1, 130.9, 130.8, 130.4, 129.8, 128.1, 126.4, 124.2, 120.4, 120.3, 54.8, 54.7, 41.0, 32.3, 29.0, 24.8.

Methyl (2-(2-(2-naphthamido)-5-methyl phenyl)-2-oxoacetyl)lysinate hydrochloride (46)

The title compound 46 was prepared from compound 42 (115 mg, 0.187 mmol) and HCl in dioxane (4M solution) according to the general procedure F. The product was obtained as yellowish solid (100 mg, 98%); $^1$HNMR (DMSO-d$_6$, 300 MHz): δ 11.7 (s, 1H), 9.34 (d, J=7.32 Hz, 1H), 8.60 (s, 1H), 8.40 (m, J=8.42 Hz, 1H), 8.19-8.10 (m, 2H), 8.09-8.00 (m, 2H), 7.97-7.96 (bs, 3H), 7.76-7.57 (m, 4H), 4.46-4.23 (m, 1H), 3.68 (s, 3H), 2.85-2.60 (m, 2H), 2.38 (s, 3H), 1.89-1.63 (m, 2H), 1.60-1.44 (m, 2H), 1.42-1.25 (m, 2H); $^{13}$CNMR (DMSO-d$_6$, 75 MHz): δ 193.7, 172.1, 165.6, 165.3, 138.4, 136.7, 135.0, 133.5, 133.2, 132.6, 131.8, 129.5, 129.1, 128.7, 128.4, 128.2, 127.6, 126.7, 123.9, 121.8, 66.8, 52.6, 52.3, 38.8, 30.2, 26.8, 22.7, 20.7; HRMS (ESI): m/z calcd for $C_{27}H_{30}N_3O_5$ [M+H]$^+$ 476.2181, found 476.2180.

General Procedure G for the Synthesis of Compounds 47 to 50

A solution of 43-46 (1 equivalent), N,N'-di-Boc-1H-pyrazole-1-carboxamidine (1.05 equiva) and triethylamine (1 equiva) was dissolved in dichloromethane and stirred at room temperature for 3-16 hours. After completion of reaction, the solvent was removed in vacuo and the residue was purified by flash chromatography on silica gel, eluting with 40% ethyl acetate in hexane to get the product.

Methyl(E)-N2-(2-(2-(2-naphthamido)phenyl)-2-oxoacetyl)-N6-(N,N'-bis(tert-butoxycarbonyl)carbamimidoyl)lysinate (47)

The title compound was prepared from 43 (105 mg, 0.175 mmol), N,N'-di-Boc-1H-pyrazole-1-carboxamidine (65 mg, 0.211 mmol) and triethylamine (0.029 mL, 0.211 mmol) according to the general procedure G. The product was obtained as colorless solid (95 mg, 77%); $^1$HNMR (CDCl$_3$, 300 MHz): δ 12.1 (bs, 1H), 11.4 (bs, 1H), 9.04-8.98 (m, 1H), 8.62-8.57 (m, 1H), 8.50 (dd, J=1.48, 8.05 Hz, 1H), 8.14-8.04 (m, 2H), 8.03-7.97 (m, 1H), 7.96-7.89 (m, 1H), 7.77-7.68 (m, 1H), 7.67-7.57 (m, 2H), 7.45 (d, J=8.03 Hz, 1H), 7.25-7.18 (m, 1H), 4.84-4.66 (m, 1H), 3.83 (s, 3H), 3.59-3.35 (m, 2H), 2.05-1.82 (m, 2H), 1.74-1.54 (m, 4H), 1.52 (s, 9H), 1.46 (s, 9H); $^{13}$CNMR (CDCl$_3$, 75 MHz): δ 191.4, 171.8, 171.1, 166.0, 162.5, 156.1, 153.2, 142.9, 137.0, 135.1, 134.7, 132.7, 131.6, 129.4, 128.8, 128.5, 128.1, 127.7, 126.8, 123.5, 122.7, 120.8, 118.6, 83.2, 77.2, 52.7, 52.2, 31.9, 28.5, 28.2, 27.9, 22.6; HRMS (ESI): m/z calcd for $C_{37}H_{45}N_5O_9$ [M+H]+ 704.3292, found 702.3290.

Methyl (E)-N$^2$-(2-(2-(2-naphthamido)-5-bromophenyl)-2-oxoacetyl)-N$^6$—(N,N'-bis(tert-butoxycarbonyl)carbamimidoyl)lysinate (48)

The title compound was prepared from 44 (70 mg, 0.140 mmol), N,N'-di-Boc-1H-pyrazole-1-carboxamidine (42.5 mg, 0.137 mmol) and triethylamine (0.019 mL, 0.137 mmol) according to the general procedure G. The product was obtained as colorless solid (50 mg, 53%); $^1$HNMR (CDCl$_3$, 300 MHz): δ 12.0 (bs, 1H), 11.4 (bs, 1H), 8.90 (d, J=9.06 Hz, 1H), 8.69 (m, J=2.35 Hz, 1H), 8.58-8.51 (m, 1H), 8.42-8.26 (m, 1H), 8.11-7.87 (m, 4H), 7.79 (dd, J=2.48, 9.16 Hz, 1H), 7.67-7.54 (m, 3H), 4.82-4.64 (m, 2H), 3.84 (s, 3H), 3.52-3.38 (m, 2H), 2.06-1.86 (m, 2H), 1.80-1.60 (m, 4H), 1.50 (s, 9H), 1.46 (s, 9H); $^{13}$CNMR (CDCl$_3$, 75 MHz): δ 190.2, 171.7, 171.1, 165.9, 161.8, 156.1, 153.3, 141.7, 139.6, 136.8, 135.1, 132.6, 131.2, 129.4, 128.9, 128.5, 128.2, 127.7, 126.9, 123.3, 122.4, 120.1, 115.2, 83.1, 77.4, 52.7, 52.3, 40.3, 31.8, 28.5, 28.2, 28.0, 22.6; HRMS (ESI): m/z calcd for $C_{37}H_{45}BrN_5O_9$ [M+H]$^+$ 782.2394, found 782.2395.

Methyl (E)-N²-(2-(2-(2-naphthamido)-5-fluorophenyl)-2-oxoacetyl)-N⁶—(N,N'-bis(tert-butoxycarbonyl)carbamimidoyl)lysinate (49)

The title compound was prepared from 45 (65 mg, 0.100 mmol), N,N'-di-Boc-1H-pyrazole-1-carboxamidine (40 mg, 0.128 mmol) and triethylamine (0.032 mL, 0.235 mmol) according to the general procedure G. The product was obtained as colorless liquid (40 mg, 47%); $^1$HNMR (CDCl$_3$, 300 MHz): δ 12.0 (bs, 1H), 11.5 (bs, 1H), 9.06-8.96 (m, 1H), 8.61-8.51 (m, 1H), 8.54-8.31 (m, 2H), 8.12-8.06 (m, 2H), 8.03-7.98 (m, 1H), 7.96-7.90 (m, 1H), 7.67-7.54 (m, 3H), 7.51-7.40 (m, 1H), 4.81-4.64 (m, 2H), 3.84 (s, 3H), 3.58-3.39 (m, 2H), 2.12-1.86 (m, 2H), 1.80-1.55 (m, 4H), 1.50 (s, 9H), 1.46 (s, 9H); $^{13}$CNMR (CDCl$_3$, 100 MHz): δ 190.0, 171.7, 165.9, 139.3, 135.1, 132.7, 131.4, 129.4, 128.9, 128.5, 128.1, 127.7, 126.9, 124.3, 123.4, 122.8, 122.7, 123.4, 122.8, 122.7, 120.5, 120.3, 119.7, 77.2, 52.7, 52.3, 31.8, 31.2, 28.5, 28.2, 27.9, 27.8, 22.6; HRMS (ESI): m/z calcd for C$_{37}$H$_{45}$FN$_5$O$_9$ [M+H]$^+$ 722.3188, found 722.3196.

Methyl (E)-N²-(2-(2-(2-naphthamido)-5-methylphenyl)-2-oxoacetyl)-N⁶—(N,N'-bis(tert-butoxycarbonyl)carbamimidoyl)lysinate (50)

The title compound was prepared from 46 (85 mg, 0.154 mmol), N,N'-di-Boc-1H-pyrazole-1-carboxamidine (57 mg, 0.185 mmol) and triethylamine (0.025 mL, 0.185 mmol) according to the general procedure G. The product was obtained as colorless liquid (80 mg, 72%); $^1$HNMR (CDCl$_3$, 300 MHz): δ 12.0 (bs, 1H), 11.5 (bs, 1H), 8.89 (d, J=8.87 Hz, 1H), 8.57 (s, 1H), 8.45-8.32 (m, 1H), 8.29-8.22 (m, 1H), 8.14-7.86 (m, 4H), 7.65-7.43 (m, 4H), 4.85-4.64 (m, 2H), 3.84 (s, 3H), 3.57-3.36 (m, 2H), 2.39 (s, 3H), 2.09-1.53 (m, 6H), 1.75-1.61 (m, 2H), 1.50 (s, 9H), 1.46 (s, 9H); $^{13}$CNMR (CDCl$_3$, 75 MHz): δ 191.5, 171.8, 165.9, 163.2, 162.7, 156.1, 153.2, 140.5, 137.9, 135.0, 134.6, 132.7, 132.4, 131.7, 129.4, 128.7, 128.4, 128.0, 127.7, 126.8, 123.5, 120.7, 118.7, 83.2, 79.5, 52.7, 52.2, 40.5, 31.9, 28.5, 28.2, 28.0, 22.6, 20.7; HRMS (ESI): m/z calcd for C$_{38}$H$_{48}$N$_6$O$_9$ [M+H]$^+$ 718.3445, found 718.3447.

General Procedure H for the Synthesis of Compounds 51 to 54

To a solution of 47-50 (1 mmol) in dichloromethane was added HCl in dioxane (4M solution) (5.0 equiv) at 0° C. The reaction mixture was warmed to room temperature and stirred for 16 h. After completion of reaction, solvent was removed under reduced pressure, treated with diethylether, and dried to yield the product.

N²-(2-(2-(2-naphthamido)phenyl)-2-oxoacetyl)-N⁶-carbamimidoyllysine hydrochloride (51)

The title compound 51 was prepared from compound 47 (75 mg, 0.106 mmol) and HCl in dioxane (4M solution) according to the general procedure H. The product was obtained as off-white solid (35 mg, 67%); $^1$HNMR (CDCl$_3$, 300 MHz): δ 11.8 (bs, 1H), 9.52-9.00 (m, 1H), 8.84-8.46 (m, 2H), 8.37-7.58 (m, 9H), 8.54-6.52 (m, 4H), 4.49-4.07 (m, 1H), 3.17-2.88 (m, 2H), 1.96-1.14 (m, 9H); $^{13}$CNMR (DMSO-d6, 150 MHz): δ 194.1, 173.1, 165.7, 165.2, 157.2, 140.9, 136.1, 135.0, 133.7, 132.6, 131.7, 129.6, 129.2, 128.8, 128.5, 128.2, 127.7, 124.0, 123.9, 121.6, 121.5, 52.4, 40.9, 30.6, 28.5, 23.0; HRMS (ESI): m/z calcd for C$_{26}$H$_{28}$N$_5$O$_5$ [M+H]$^+$ 490.2084, found 490.2035.

N²-(2-(2-(2-naphthamido)-5-bromophenyl)-2-oxoacetyl)-N⁶-carbamimidoyllysine hydrochloride (52)

The title compound 52 was prepared from compound 48 (40 mg, 0.051 mmol) and HCl in dioxane (4M solution) according to the general procedure H. The product was obtained as off-white solid (20 mg, 69%); $^1$HNMR (DMSO-d$_6$, 300 MHz): δ 11.6 (bs, 1H), 9.16 (d, J=7.61 Hz, 1H), 8.62 (s, 1H), 8.34 (d, J=8.87 Hz, 1H), 8.19-8.08 (m, 2H), 8.07-7.91 (m, 4H), 7.78-7.58 (m, 3H), 7.54-6.65 (m, 4H), 4.34-4.18 (m, 1H), 3.16-2.93 (m, 2H), 1.89-1.61 (m, 2H), 1.53-1.16 (m, 4H); $^{13}$CNMR (DMSO-d6, 150 MHz): δ 191.1, 173.1, 165.8, 164.2, 157.2, 139.2, 131.4, 129.6, 129.1, 128.8, 128.7, 127.6, 124.7, 124.2, 124.0, 115.7, 52.4, 40.9, 30.4, 28.4, 23.0; HRMS (ESI): m/z calcd for C$_{26}$H$_{27}$BrN$_5$O$_5$ [M+H]$^+$ 568.1196, found 568.1190.

N²-(2-(2-(2-naphthamido)-5-fluorophenyl)-2-oxoacetyl)-N⁶-carbamimidoyllysine hydrochloride (53)

The title compound 53 was prepared from compound 49 (30 mg, 0.041 mmol) and HCl in dioxane (4M solution) according to the general procedure H. The product was obtained as off-white solid (15 mg, 71%); $^1$HNMR (DMSO-d$_6$, 300 MHz): δ 11.4 (s, 1H), 9.09 (d, J=7.10 Hz, 1H), 8.60 (bs, 1H), 8.34-8.25 (m, 1H), 8.15-8.06 (m, 2H), 8.07-7.99 (m, 2H), 7.72-7.43 (m, 5H), 7.40-6.64 (m, 4H), 4.34-4.12 (m, 2H), 3.08-2.93 (m, 2H), 1.83-1.60 (m, 2H), 1.45-1.17 (m, 4H); $^{13}$CNMR (DMSO-d$_6$, 150 MHz): δ 191.3, 173.1, 165.8, 164.2, 157.2, 142.6, 139.2, 135.9, 135.0, 133.2, 132.5, 131.4, 129.6, 129.1, 129.0, 128.7, 128.6, 128.2, 127.6, 124.1, 122.3, 30.4, 28.4, 23.0; HRMS (ESI): m/z calcd for C$_{26}$H$_{27}$FN$_5$O$_5$ [M+H]$^+$ 508.1992, found 508.1991.

N²-(2-(2-(2-naphthamido)-5-methylphenyl)-2-oxoacetyl)-N⁶-carbamimidoyllysine hydrochloride (54)

The title compound 54 was prepared from compound 50 (70 mg, 0.097 mmol) and HCl in dioxane (4M solution) according to the general procedure H. The product was obtained as off-white solid (30 mg, 61%); $^1$HNMR (DMSO-d$_6$, 300 MHz): δ 11.8 (s, 1H), 9.43-9.11 (m, 1H), 8.70-8.55 (bs, 1H), 8.53-8.38 (m, 1H), 8.22-7.98 (m, 4H), 7.79 (bs, 1H), 7.74-7.56 (m, 4H), 7.53-6.69 (m, 4H), 4.40-4.22 (m, 1H), 3.16-2.99 (m, 2H), 2.35 (s, 3H), 1.97-1.59 (m, 2H), 1.58-1.18 (m, 4H); $^{13}$CNMR (DMSO-d$_6$, 150 MHz): δ 194.4, 178.7, 173.2, 165.5, 165.2, 157.2, 138.6, 136.8, 134.9, 133.9, 133.1, 132.6, 131.8, 129.6, 129.1, 128.7, 128.4, 128.2, 127.6, 123.8, 121.2, 52.4, 40.9, 30.5, 28.4, 23.1, 20.6; HRMS (ESI): m/z calcd for C$_{27}$H$_{30}$N$_5$O$_5$ [M+H]$^+$ 504.2240, found 504.2241.

General Procedure I for the Synthesis of Compounds 55 to 56

To a solution of 47-50 (1 mmol) in dichloromethane (1 mL) was added TFA (1 mL). The reaction mixture was warmed to room temperature and stirred for 16 h. After completion of the reaction, excess solvent was removed under reduced pressure and treated with excess HCl in dioxane (4M solution) to exchange the TFA anion with HCl. After that reaction mixture again concentrated to get sticky solid. This was dissolved in minimum amount of MeOH (10 drops) and diethylether (5-10 mL) was added to get precipitation of the product (65%-85%). (see Wales, S. M.; Hammer, K. A.; King, A. M.; Tague, A. J.; Lyras, D.; Riley, T. V.; Keller, P. A.; Pyne, S. G. *Org. Biomol. Chem.* 2015, 13, 5743.)

N-(2-(2-((7-guanidino-2-oxoheptan-3-yl)amino)-2-oxoacetyl)phenyl)-2-naphthamide hydrochloride (55)

The title compound 55 was prepared from compound 47 (84 mg, 0.149 mmol), TFA and HCl in dioxane (4M solution) according to the general procedure I. The product was obtained as yellowish solid (60 mg, 87%); $^1$HNMR (DMSO-$d_6$, 300 MHz): δ 11.8 (bs, 1H), 9.35 (bs, 1H), 8.84-8.46 (m, 2H), 8.34-7.58 (m, 10H), 7.51-6.73 (m, 4H), 4.52-4.23 (m, 1H), 3.67 (s, 3H), 3.17-2.92 (m, 2H), 1.96-1.57 (m, 2H), 1.54-1.13 (m, 4H); $^{13}$CNMR (DMSO-$d_6$, 150 MHz): δ 193.7, 172.0, 170.7, 165.7, 165.1, 157.3, 142.3, 140.7, 136.1, 135.0, 133.5, 132.6, 131.7, 129.1, 128.8, 128.6, 128.2, 127.6, 124.1, 123.9, 121.7, 52.6, 52.4, 41.5, 36.0, 30.4, 28.4, 22.9; HRMS (ESI): m/z calcd for $C_{27}H_{30}N_5O_5$ [M+H]$^+$ 504.2239, found 504.2241.

N-(4-bromo-2-(2-((7-guanidino-2-oxoheptan-3-yl)amino)-2-oxoacetyl)phenyl)-2-naphthamide hydrochloride (56)

The title compound 56 was prepared from compound 48 (100 mg, 0.128 mmol), TFA and HCl in dioxane (4M solution) according to the general procedure I. The product was obtained as off-white solid (60 mg, 81%); $^1$HNMR (DMSO-$d_6$, 400 MHz): δ 11.5 (s, 1H), 9.29 (d, J=7.32 Hz, 1H), 8.64-8.57 (m, 1H), 8.24 (d, J=8.61 Hz, 1H), 8.16-8.09 (m, 2H), 8.08-7.89 (m, 4H), 7.75-7.63 (m, 2H), 7.60-7.49 (m, 1H), 7.45-6.44 (m, 4H), 4.38-4.24 (m, 1H), 3.65 (s, 3H), 3.11-2.92 (m, 2H), 1.88-1.59 (m, 2H), 1.50-1.10 (m, 4H); $^{13}$CNMR (DMSO-$d_6$, 150 MHz): δ 194.1, 173.1, 165.7, 165.2, 157.2, 140.9, 136.1, 135.0, 133.7, 132.6, 131.7, 129.6, 129.2, 128.8, 128.5, 128.2, 127.7, 124.0, 123.9, 121.6, 121.5, 52.4, 40.8, 40.9, 30.6, 28.5, 23.0; HRMS (ESI): m/z calcd for $C_{27}H_{29}BrN_5O_5$ [M+H]$^+$ 582.1346, found 582.1347.

General Procedure J for the Synthesis of Compounds 57 and 58

To a solution of 38 and 39 (1 mmol) in THF (5 mL), MeOH (3 mL) and water (1.5 mL) was added lithium hydroxide (5 mmol). The reaction mixture was stirred at room temperature for 16 h. After completion of the reaction, solvent was removed under reduced pressure and treated with dilute HCl solution and extracted with ethyl acetate. The organic layer was separated and dried over sodium sulfate filtered and evaporated under reduced pressure to yield product.

$N^2$-(2-(2-(2-naphthamido)phenyl)-2-oxoacetyl)-$N^6$-(tert-butoxycarbonyl) lysine (57)

The title compound 57 was prepared from compound 38 (350 mg, 0.586 mmol), lithium hydroxide (5 mmol) according to the general procedure J. The product was obtained off-white solid (320 mg, 100%); $^1$HNMR (DMSO-$d_6$, 300 MHz): δ 12.8 (bs, 1H), 11.9 (s, 1H), 9.15 (d, J=7.07 Hz, 1H), 8.69-8.50 (m, 2H), 8.21-7.98 (m, 4H), 7.97-7.87 (m, 1H), 7.80 (t, J=7.26 Hz, 1H), 7.74-7.60 (m, 2H), 7.34 (t, J=7.62 Hz, 1H), 6.85-6.64 (m, 1H), 4.39-4.14 (m, 2H), 2.98-2.73 (m, 2H), 1.87-1.54 (m, 2H), 1.50-1.08 (m, 13H); $^{13}$CNMR (DMSO-$d_6$, 75 MHz): δ 194.3, 173.2, 167.8, 165.7, 165.2, 156.0, 141.0, 136.2, 135.0, 133.8, 132.6, 131.7, 129.6, 129.2, 128.8, 128.5, 128.2, 127.6, 123.9, 121.4, 121.3, 77.8, 52.4, 43.9, 30.7, 29.5, 28.7, 23.2; HRMS (ESI): m/z calcd for $C_{30}H_{33}N_3NaO_7$ [M+H]$^+$ 570.2216, found 570.2211.

$N^2$-(2-(2-(2-naphthamido)-5-bromophenyl)-2-oxoacetyl)-$N^6$-(tert-butoxycarbonyl)lysine (58)

The title compound 58 was prepared from compound 39 (550 mg, 0.809 mmol), lithium hydroxide (5 mmol) according to the general procedure J. The product was obtained as off-white solid (500 mg, 98%); $^1$HNMR (DMSO-$d_6$, 400 MHz): δ 11.6 (bs, 1H), 9.11 (d, J=7.50 Hz, 1H), 8.60 (s, 1H), 8.36 (d, J=9.01 Hz, 1H), 8.17-8.10 (m, 2H), 8.08-7.93 (m, 4H), 7.75-7.58 (m, 2H), 6.80-6.63 (m, 1H), 4.30-4.17 (m, 1H), 2.95-2.76 (m, 2H), 1.83-1.59 (m, 2H), 1.46-1.20 (m, 15H); $^{13}$CNMR (DMSO-$d_6$, 75 MHz): δ 191.7, 173.2, 165.8, 164.3, 156.0, 139.4, 138.0, 135.2, 135.0, 132.6, 131.4, 129.6, 129.1, 128.8, 128.7, 128.2, 127.6, 124.4, 124.1, 124.0, 115.6, 77.8, 60.2, 52.6, 30.5, 29.5, 28.7, 23.2; HRMS (ESI): m/z calcd for $C_{30}H_{32}BrN_3NaO_7$ [M+H]$^+$ 648.1293, found 648.1316.

General Procedure K for the Synthesis of Compounds 59 and 60

A solution of 57 and 58 (1 mmol), methyl 2-amino-5-((tert-butoxycarbonyl)amino)pentanoate hydrochloride (1.0 mmol), EDC.HCl (1.2 mmol), HOBt (1.2 mmol) was treated with DIPEA (2.5 mmol) at 0° C. and stirred at same temperature for 15-30 min. After completion of the reaction, water was added and extracted with ethyl acetate. The organic layer was separated and dried over sodium sulfate, filtered and evaporated under reduced pressure and purified by column chromatography to yield product.

Methyl 2-(2-(2-(2-(2-naphthamido)phenyl)-2-oxoacetamido)-6-((tert-butoxycarbonyl)amino) hexanamido)-5-((tert-butoxycarbonyl)amino) pentanoate (59)

The title compound 59 was prepared from compound 57 (230 mg, 0.393 mmol) and methyl 2-amino-5-((tert-butoxycarbonyl)amino) pentanoate hydrochloride (111 mg, 0.393 mmol), according to the general procedure K. The product was obtained as yellowish solid (186 mg, 60%); $^1$HNMR (DMSO-$d_6$, 300 MHz): δ 11.8 (bs, 1H), 8.94 (d, J=7.84 Hz, 1H), 8.64-8.52 (m, 2H), 8.48 (d, J=7.43 Hz, 1H), 8.19-8.10 (m, 2H), 8.09-7.99 (m, 2H), 7.92-7.84 (m, 2H), 7.83-7.84 (m, 1H), 7.73-7.60 (m, 2H), 7.40-7.27 (m, 1H), 6.92-6.61 (m, 2H), 4.49-4.39 (m, 2H), 4.33-4.17 (m, 1H), 3.63 (s, 3H), 3.06-2.72 (m, 4H), 1.82-1.50 (m, 4H), 1.50-1.19 (m, 24H); $^{13}$CNMR (DMSO-$d_6$, 75 MHz): δ 194.3, 172.8, 171.4, 165.7, 164.8, 156.0, 140.8, 136.0, 135.0, 133.7, 132.6, 131.7, 129.6, 129.2, 128.8, 128.5, 128.2, 127.6, 123.9, 121.5, 121.4, 77.9, 77.8, 52.7, 52.2, 32.1, 29.7, 28.7, 28.5, 26.4, 23.0; HRMS (ESI): m/z calcd for $C_{41}H_{53}N_5NaO_{10}$ [M+H]$^+$ 798.3687, found 798.3685.

Methyl 2-(2-(2-(2-(2-naphthamido)-5-bromophenyl)-2-oxoacetamido)-6-((tert-butoxycarbonyl)amino) hexanamido)-5-((tert-butoxycarbonyl)amino)pentanoate (60)

The title compound 60 was prepared from compound 58 (200 mg, 0.332 mmol) and methyl 2-amino-5-((tert-butoxycarbonyl)amino) pentanoate hydrochloride (106 mg, 0.093 mmol), according to the general procedure K. The product was obtained as off-white solid (90 mg, 31%); $^1$HNMR (CDCl$_3$, 400 MHz): δ 12.0 (bs, 1H), 8.91 (d, J=9.10 Hz, 1H), 8.63 J=2.41 Hz, 1H), 8.57-8.50 (m, 1H), 8.08-8.01 (m, 2H), 8.09-7.95 (m, 1H), 7.94-7.88 (m, 1H), 7.82 (d, J=7.97 Hz, 1H), 7.78 (dd, J=2.37, 9.07 Hz, 1H), 7.65-7.56 (m, 2H), 7.41 (bs, 1H), 5.05-4.44 (m, 4H), 3.78 (s, 3H), 3.28-3.00 (m, 4H), 2.08-1.73 (m, 4H), 1.65-1.45 (m, 6H), 1.42 (s, 9H), 1.41 (s, 9H); $^{13}$CNMR (CDCl$_3$, 75 MHz): δ 190.5, 172.4, 170.3, 165.9, 162.1, 156.5, 156.2, 141.8, 139.5, 136.7, 135.1, 132.6, 131.2, 129.4, 128.9, 128.5, 128.2, 127.7, 126.9, 123.4, 122.5, 120.1, 115.0, 79.7, 79.2, 77.2, 53.2, 52.5, 39.8, 32.1, 29.4, 28.4, 28.3, 26.8, 22.2; HRMS (ESI): m/z calcd for $C_c H_{52}BrN_5O_{10}$ [M+H]$^+$ 854.2979, found 854.2970.

General Procedure L for the Synthesis of Compounds 61 to 62

To a solution of 59 and 60 (1 mmol) in dichloromethane was added HCl in dioxane (4M solution) (5.0 equiv) at 0° C. The reaction mixture was warmed to room temperature and stirred for 16 h. After completion of reaction, excess solvent was removed under reduced pressure, treated with diethylether, and dried to yield the product.

Methyl 2-(2-(2-(2-(2-naphthamido)phenyl)-2-oxoacetamido)-6-aminohexanamido)-5-aminopentanoate dihydrochloride (61)

The title compound 61 was prepared from compound 59 (175 mg, 0.206 mmol) and HCl in dioxane (4M solution) according to the general procedure L. The product was obtained as grey sticky solid (95 mg, 80%); $^1$HNMR (DMSO-d$_6$, 300 MHz): δ 11.8 (s, 1H), 9.03 (d, J=9.01 Hz, 1H), 8.71 (d, J=7.07 Hz, 1H), 8.62 (bs, 1H), 8.54 (d, J=8.27 Hz, 1H), 8.23-7.60 (m, 14H), 7.39-7.28 (m, 1H), 4.50-4.37 (m, 1H), 4.36-4.24 (m, 1H), 3.65 (s, 3H), 2.91-2.66 (m, 4H), 1.91-1.51 (m, 8H), 1.47-1.26 (m, 2H); $^{13}$CNMR (DMSO-d$_6$, 150 MHz): δ 193.3, 172.5, 171.7, 166.1, 164.8, 140.1, 135.9, 135.0, 133.3, 132.5, 131.6, 129.5, 129.2, 128.9, 128.4, 128.2, 127.8, 124.3, 123.9, 122.2, 121.9, 52.9, 52.5, 52.0, 38.8, 31.4, 27.9, 26.9, 24.0, 22.4; HRMS (ESI): m/z calcd for $C_{31}H_{38}N_5O_6$ [M+H]$^+$ 576.2841, found 576.2817.

Methyl 2-(2-(2-(2-(2-naphthamido)-5-bromophenyl)-2-oxoacetamido)-6-aminohexanamido)-5-aminopentanoate dihydrochloride (62)

The title compound 62 was prepared from compound 60 (130 mg, 0.152 mmol) and HCl in dioxane (4M solution) according to the general procedure L. The product was obtained as grey sticky solid (89 mg, 89%); $^1$HNMR (DMSO-d$_6$, 300 MHz): δ 11.5 (s, 1H), 8.91 (d, J=7.74 Hz, 1H), 8.65 (d, J=7.32 Hz, 1H), 8.63-6.58 (m, 1H), 8.27-8.20 (m, 1H), 8.12 (d, J=8.44 Hz, 2H), 8.05 (d, J=8.13 Hz, 1H), 8.02-7.98 (m, 1H), 7.97-7.92 (m, 2H), 7.91-7.83 (m, 5H), 7.73-7.63 (m, 2H), 4.42-4.34 (m, 1H), 4.33-4.20 (m, 1H), 3.65 (s, 3H), 2.88-2.62 (m, 4H), 1.89-1.44 (m, 8H), 1.44-1.21 (m, 2H); $^{13}$CNMR (DMSO-d$_6$, 150 MHz): δ 190.7, 172.5, 171.4, 165.8, 163.4, 138.7, 137.5, 135.0, 134.6, 132.5, 131.4, 129.6, 129.0, 128.7, 128.2, 127.6, 125.5, 124.1, 115.7, 52.9, 52.4, 52.0, 38.9, 38.7, 28.0, 26.9, 24.1, 22.5; HRMS (ESI): m/z calcd for $C_{31}H_{36}BrN_5O_6$ [M+H]$^+$ 654.1921, found 654.1922.

General Procedure M for the Synthesis of Compounds 63 and 64

A solution of 61 and 62 (1 equivalent), N,N'-di-Boc-1H-pyrazole-1-carboxamidine (1.05 equivalent) and triethylamine (1 equivalent) was dissolved in dichloromethane and stirred at room temperature for 3-16 hours. After completion of reaction, the solvent was removed in vacuo and the residue was purified by flash chromatography on silica gel, eluting with 40% ethyl acetate in hexane to yield the product (51% and 65%).

Methyl (E)-N2-(N2-(2-(2-(2-naphthamido)phenyl)-2-oxoacetyl)-N6-((Z)—N,N'-bis(tert-butoxycarbonyl)carbamimidoyl)lysyl)-Nw,Nw'-bis(tert-butoxycarbonyl)argininate (63)

The title compound was prepared from 61 (82 mg, 0.126 mmol), N,N'-di-Boc-1H-pyrazole-1-carboxamidine (98 mg, 0.316 mmol) and triethylamine (0.043 mL, 0.316 mmol) according to the general procedure M. The product was obtained as yellowish solid (86 mg, 65%); $^1$HNMR (DMSO-d$_6$, 300 MHz): δ 11.8 (bs, 1H), 11.4 (d, J=6.05 Hz, 1H), 8.95 (d, J=7.52 Hz, 1H), 8.62-8.56 (m, 1H), 8.56-8.48 (m, 2H), 8.38-8.19 (m, 2H), 8.18-8.10 (m, 2H), 8.08-7.99 (m, 2H), 7.91-7.82 (m, 1H), 7.81-7.73 (m, 1H), 7.73-7.61 (m, 2H), 7.38-7.28 (m, 1H), 4.46-4.26 (m, 2H), 3.64 (s, 3H), 3.29-3.04 (m, 4H), 1.87-1.18 (m, 46H); $^{13}$CNMR (DMSO-d$_6$, 150 MHz): δ 194.1, 172.6, 171.4, 165.7, 164.8, 163.6, 163.5, 155.7, 155.6, 152.5, 152.4, 140.7, 135.9, 133.6, 132.6, 131.7, 129.6, 128.7, 128.5, 128.2, 127.6, 124.0, 123.9, 121.7, 121.4, 104.6, 83.3, 82.3, 52.7, 52.3, 32.0, 31.7, 28.7, 28.4, 28.1, 28.0, 25.5, 23.0; HRMS (ESI): m/z calcd for $C_{53}H_{74}N_9O_{14}$ [M+H]$^+$ 1060.5345, found 1060.5350.

Methyl (E)-N$^2$—(N$^2$-(2-(2-(2-naphthamido)-5-bromophenyl)-2-oxoacetyl)-N$^6$—((Z)—N,N'-bis(tert-butoxycarbonyl)carbamimidoyl)lysyl)-Nw,Nw'-bis(tert-butoxycarbonyl)argininate (64)

The title compound was prepared from 62 (75 mg, 0.114 mmol), N,N'-di-Boc-1H-pyrazole-1-carboxamidine (51 mg, 0.089 mmol) and triethylamine (0.022 mL, 0.165 mmol) according to the general procedure M. Off white solid (50 mg, 51%); $^1$HNMR (DMSO-d6, 300 MHz): δ 12.1 (s, 1H), 9.00-8.84 (m, 2H), 8.66-8.64 (m, 1H), 8.59-8.55 (m, 1H), 8.10-8.03 (m, 2H), 8.02-7.98 (m, 1H), 7.97-7.89 (m, 2H), 7.77 (dd, J=2.24, 9.12 Hz, 1H), 7.65-7.56 (m, 2H), 4.84-4.74 (m, 1H), 4.57-4.47 (m, 1H), 3.93-3.80 (m, 1H), 3.76 (s, 3H), 3.73-3.53 (m, 3H), 2.21-2.10 (m, 1H), 2.05-1.90 (m, 3H), 1.87-1.66 (m, 4H), 1.63-1.34 (m, 38H); $^{13}$CNMR (DMSO-d$_6$, 100 MHz): δ 172.0, 166.0, 162.0, 145.5, 141.7, 139.2, 136.7, 135.1, 134.3, 132.6, 131.3, 129.5, 128.9, 128.6, 128.2, 127.7, 126.9, 123.5, 122.4, 120.3, 114.9, 110.0, 52.7, 52.6, 52.4, 32.1, 28.3, 28.1, 28.0, 27.9, 25.8, 22.1; HRMS (ESI): m/z calcd for $C_{53}H_{73}BrN_9O_{14}$ [M+H]$^+$ 1138.4445, found 1138.4431.

Synthesis of Compounds 65 and 66

Methyl (2-(2-(2-naphthamido)phenyl)-2-oxoacetyl) arginylargininate dihydrochloride (65)

The title compound 65 was prepared from compound 63 (70 mg, 0.066 mmol), TFA and HCl in dioxane (4M solution) according to the general procedure I. The product was obtained as off-white solid (38 mg, 44%); $^1$HNMR (DMSO-d$_6$, 600 MHz): δ 11.9 (bs, 1H), 9.01 (d, J=7.80 Hz, 1H), 8.67-8.62 (m, 2H), 8.60 (bs, 1H), 8.11-8.03 (m, 3H), 8.01 (d, J=7.93 Hz, 1H), 7.93 (d, J=7.78 Hz, 1H), 7.81 (t, J=5.31 Hz, 1H), 7.77-7.70 (m, 2H), 7.56 (bs, 1H), 7.50-7.23 (m, 4H), 7.15-6.76 (m, 4H), 4.55-4.46 (m, 1H), 4.38-4.31 (m, 2H), 3.66 (s, 3H), 3.17-3.05 (m, 4H), 1.88-1.77 (m, 2H), 1.76-1.64 (m, 2H), 1.63-1.54 (m, 2H), 1.54-1.47 (m, 2H), 1.46-1.36 (m, 2H); $^{13}$CNMR (DMSO-d$_6$, 150 MHz): δ 194.3, 172.5, 171.5, 165.6, 164.9, 157.4, 141.1, 135.8, 135.8, 133.8, 132.6, 131.7, 129.4, 128.9, 128.5, 128.4, 128.0, 127.3, 123.8, 123.5, 121.1, 121.0, 52.8, 52.2, 52.1, 41.0, 40.7, 40.5, 31.9, 28.4, 28.2, 22.7; HRMS (ESI): m/z calcd for $C_{33}H_{42}N_9O_6$ [M+H]$^+$ 660.3259, found 660.3253.

Methyl (2-(2-(2-naphthamido)-5-bromophenyl)-2-oxoacetyl)arginylargininate dihydrochloride (66)

The title compound 66 was prepared from compound 64 (42 mg, 0.037 mmol), TFA and HCl in dioxane (4M solution) according to the general procedure I. The product was obtained as off-white solid (20 mg, 72%); $^1$HNMR (DMSO-d$_6$, 400 MHz): δ 11.5 (bs, 1H), 8.86 (d, J=7.75 Hz, 1H), 8.67-8.50 (m, 2H), 8.23 (d, J=8.56 Hz, 1H), 8.15-8.08 (m, 2H), 8.07-7.98 (m, 2H), 7.97-7.89 (m, 2H), 7.75-7.58 (m, 4H), 7.52-6.63 (m, 8H), 4.44-4.34 (m, 2H), 3.63 (s, 3H), 3.17-2.95 (m, 4H), 3.63 (s, 3H), 1.86-1.27 (m, 10H); $^{13}$CNMR (DMSO-d$_6$, 150 MHz): δ 190.8, 172.5, 171.3, 165.8, 163.4, 157.3, 157.2, 138.7, 137.5, 135.0, 134.6, 132.5, 131.3, 129.5, 129.0, 128.8, 128.7, 128.2, 127.6, 125.4, 124.3, 124.0, 115.7, 52.8, 52.4, 52.1, 41.0, 40.7, 31.8, 28.5, 28.2, 25.5, 22.7; HRMS (ESI): m/z calcd for $C_{33}H_{41}BrN_9O_6$ [M+H]$^+$ 369.6214, found 369.6215 (z=2).

Minimal Inhibitory Concentration (MIC) Determination

The antibacterial activity of the compounds was determined by the determination of minimal inhibitory concentration (MIC) by following the previously published protocol (see Nizalapur, S.; Ho, K. K.; Kimyon, Ö.; Yee, E.; Berry, T.; Manefield, M.; Cranfield, C. G.; Willcox, M.; Black, D. S.; Kumar, N. Org. Biomol. Chem. 2016, 14, 3623). The compounds to be tested were dissolved and diluted in autoclaved Millipore water. A single colony of bacteria was cultured overnight in TSB at 37° C. The resulting bacteria were collected by centrifugation and re-suspended in the same volume of MHB twice. Optical density (OD) of the resulting culture was adjusted to 0.1 at 600 nm (108 CFU/mL) in MHB, and the adjusted culture was further diluted to 105 CFU/mL in MHB. Then, 100 μL of the bacterial solution was added to wells of a 96-well plate containing 100 μL of serially diluted compound. Two controls were also prepared: one containing 100 μL of MHB media and 100 μL sterile water, and the other containing 100 μL of bacterial solution and 100 μL sterile water. The plates were then incubated at 37° C. for 24 h, and the MIC was recorded by measuring the OD value at 600 nm using a Wallac Victor (Perkin-Elmer) microplate reader. The MIC value was determined as the lowest concentration of compound that inhibited the complete growth of the bacteria (i.e. OD similar to that of the control having no bacteria). Each experiment was performed in triplicate and was repeated in three independent experiments.

Toxicity Assay

The normal human lung fibroblasts MRC-5 were cultured in minimal essential medium (MEM, Invitrogen) supplemented with 10% foetal calf serum (FCS), 1% L-glutamine-penicillin-streptomycin, 2% sodium bicarbonate, 1% non-essential amino acids (NEAA) and 1% sodium pyruvate. The cell line was maintained at 37° C. in 5% CO2 as an adherent monolayer and was passaged upon reaching confluence by standard cell culture techniques. MRC-5 cells were seeded at 2×104 cells per well in 96-well plates to ensure full confluence (quiescence). Cells were treated 24 h after seeding with 0.1 to 1000 μM of compounds. After 72 h drug incubation, the treated media was replaced with fresh media containing 10% Alamar blue and the cells were incubated for another 6 h. The metabolic activity was detected by spectrophotometric analysis by assessing the absorbance of Alamar blue as previously described by Pasquier et. al (see Pasquier, E.; Ciccolini, J.; Carre, M.; Giacometti, S.; Fanciullino, R.; Pouchy, C.; Montero, M.-P.; Serdjebi, C.; Kavallaris, M.; André, N. Oncotarget 2011, 2, 797).

Cell proliferation was determined and expressed as a percentage of untreated control cells. The determination of IC50 values was performed using GraphPad Prism 6 (San Diego, Calif., USA).

Biofilm Disruption Assay

Bacterial cultures were grown in TSB media for overnight at 37° C. with shaking at 150 r.p.m. Cultures were diluted (1:20) in YPD medium and 200 μl aliquots were dispensed to flat bottom 96-well plate wells (Sarstedt Australia). Cultures were supplemented with varying concentrations of synthetic compounds dissolved in water. For pre-established biofilm assay, cultures were grown in 96-well plate wells overnight prior to supplementation with synthetic compounds. Control cultures were supplemented with an equal amount of DMSO. Plates were sealed with self-adhesive microplate sealers (TopSeal-A, PerkinElmer) to allow air diffusion and to prevent condensation. Cultures were incubated overnight at 37° C. with shaking at 150 r.p.m. Biofilms adhered on polystyrene substratum were quantified by crystal violet staining as described previously (see Wiegand, I.; Hilpert, K.; Hancock, R. E. W. Nat. Protocols 2008, 3 (2), 163-175). All cultures were prepared in triplicates. Error bars represent the standard error of three independent experiments (n=3).

Biofilm Inhibition Assay

Bacterial cultures were grown in TSB media for overnight at 37° C. with shaking at 150 r.p.m. Cultures were diluted (1:20) in YPD medium and 200 μl aliquots were dispensed to flat bottom 96-well plate wells (Sarstedt Australia). Cultures were supplemented with varying concentrations of synthetic compounds dissolved in water. For no-established biofilm assay, cultures were grown in 96-well plate wells overnight along with synthetic compounds. Control cultures were supplemented with an equal amount of water. Plates were sealed with self-adhesive microplate sealers (TopSeal-A, PerkinElmer) to allow air diffusion and to prevent condensation. Cultures were incubated overnight at 37° C. with shaking at 150 r.p.m. Biofilms adhered on polystyrene substratum were quantified by crystal violet staining as described previously (see Wiegand, I.; Hilpert, K.; Hancock, R. E. W. Nat. Protocols 2008, 3 (2), 163-175). All cultures were prepared in triplicates. Error bars represent the standard error of three independent experiments (n=3).

Confocal Microscope

S. aureus and Serratia marcescens biofilms were grown by adding 1.5 ml of bacterial cells (OD$_{600}$ nm~0.600) suspended in fresh TSB medium into 35×10 mm polystyrene petri dishes and incubated over 24 h at 37° C. in a shaking incubator at 120 r.p.m. Cultures were supplemented with varying concentrations of synthetic compounds dissolved in water. Control cultures were supplemented with an equal amount of water. After 24 h, the biofilm growth medium was discarded and the biofilms were gently rinsed 3 times with PBS (pH: 7.0) in order to remove any planktonic bacterial cells. The remaining substratum adhered biofilms were then stained with Live/dead stain (Invitrogen, Oregon, USA) for 20 mins in the dark and then subjected to confocal microscopy. Stained biofilms were visualized with FV 1200 Confocal microscope.

Membrane Conduction Assay

Tethered bilayer lipid membranes (tBLMs) were used to determine whether the compounds were lytic to cell membranes. The ability to form pores in tBLMs was determined using AC electrical impedance spectroscopy (see: Cranfield, C. G.; Bettler, T.; Cornell, B. *Langmuir* 2015, 31, 292; and Cranfield, Charles G.; Cornell, Bruce A.; Grage, Stephan L.; Duckworth, P.; Carne, S.; Ulrich, Anne S.; Martinac, B. *Biophys. J.* 2014, 106, 182). tBLMs were created as described previously (see Cranfield, C.; Came, S.; Martinac, B.; Cornell, B. In *Methods in Membrane Lipids*; Owen, D. M., Ed.; Springer New York: 2015; Vol. 1232, p 45). Briefly, tethered benzyl-disulfide (tetra-ethyleneglycol) n=2 C20-phytanyl tethers: benzyl-disulfide-tetra-ethyleneglycol-OH spacers in the ratio of 1:10 were coated onto a gold patterned polycarbonate slide (SDx Tethered Membranes Pty Ltd, Australia). To these tethers, a 3 mM 100% ethanol solution of a standard mobile lipid phase [70% zwitterionic C20 Diphytanyl-Glycero-Phosphatidylcholine lipid: 30% C20 Diphytanyl-diglyceride-OH ether] was added. In order to create negatively charged bacterial-like membranes, the same mobile lipid phase were instead supplemented with 30% palmitoyl-oleoyl-phosphatidylglycerol (POPG) (Avanti Lipids, USA). This lipid phase was left to incubate with the tethered electrodes for 2 min before being washed with 3×200 ml phosphate buffered saline (PBS). Electrical impedance measures where performed with a TethaPod™ operated with TethaQuick™ software (SDx Tethered Membranes Pty Ltd, Australia). A 50 mV peak-to-peak AC excitation at 0.1, 0.2, 0.5, 1, 2, 5, 40, 100, 200, 500, and 1000 Hz was delivered to the tethers. The resultant data were fitted to a Constant Phase Element in series with a Resistor/Capacitor network using a proprietary adaptation of a Lev Mar fitting routine as described previously (see Cranfield, C. G.; Berry, T.; Holt, S. A.; Hossain, K. R.; Le Brun, A. P.; Carne, S.; Al Khamici, H.; Coster, H.; Valenzuela, S. M.; Cornell, B. *Langmuir* 2016, 32 (41), 10725-10734).

Antimicrobial Activity

The antibacterial activity of the guanylated peptidomimetics (34-38, 51-56, 61, 62, 65 and 66) was investigated by the determination of their minimum inhibitory concentration (MIC) against *S. aureus*, according to a previously published protocol (see Wiegand, I.; Hilpert, K.; Hancock, R. E. W. *Nat. Protocols* 2008, 3 (2), 163-175). The results of the MIC assay are given below in Table 1.

TABLE 1

Antibacterial activity (MIC) of compounds against *S. aureus* and *E. coli*.

| | Compound | Minimum inhibitory concentration (MIC ($\mu g\ mL^{-1}$)) | |
|---|---|---|---|
| | | S. aureus | E. coli |
| Series-I | 34 | 23 | >110 |
| | 35 | 6 | >110 |
| | 36 | 8 | >110 |
| | 37 | 30 | 59 |
| | 38 | 93 | >110 |
| Series-II | 51 | 53 | 66 |
| | 52 | 77 | 77 |
| | 53 | 108 | 68 |
| | 54 | 54 | 69 |
| | 55 | >140 | 17 |
| | 56 | >140 | 19 |
| Series-III | 61 | 130 | 39 |
| | 62 | 23 | 21 |
| | 65 | 18 | 90 |
| | 66 | 10 | 50 |
| | Gentamicin | <0.6 | 2.5 |

The Series-I compounds (34-38), containing a naphthoyl ring, 3 carbon linker and monoguanidine group showed moderate to excellent antibacterial activity (MIC) against *S. aureus*. The naked scaffold with an unsubstituted phenyl moiety, compound 34, possessed good MIC value of 23 µg mL$^{-1}$. Interestingly, the introduction of fluorine on this ring (37) decreased the activity of the scaffold, returning an MIC value of 30 µg mL$^{-1}$. However, introduction of the bulkier electron withdrawing groups bromine and chlorine (35 and 36, respectively) improved the antibacterial activity, with MIC values of 6 and 8 µg mL$^{-1}$, respectively. Conversely, addition of a comparatively more electron-rich methyl group on the phenyl ring (38) was found to diminish the antimicrobial activity, returning an MIC value of 93 µg mL$^{-1}$ against *S. aureus*. Surprisingly, with the exception of compound 37 (MIC=59 µg mL$^{-1}$), every compound from Series-I exhibited high MICs (i.e. low antibacterial activity) of >110 µg mL$^{-1}$ (250 µM), against *E. coli*.

In general, the Series-II monopeptide compounds were found to have lower antibacterial activities against *S. aureus* and higher activities against *E. coli* than their Series-I counterparts, with MIC values of 53->140 µg mL$^{-1}$ and 17-139 µg mL$^{-1}$, respectively. The esterified compounds (55-56), with MIC values >135 µg mL$^{-1}$, were less active than their corresponding acid derivatives (51-53), which showed MIC values of 53-108 µg mL$^{-1}$. This might be due to the potential for the acid derivatives to form a zwitterionic species, therefore increasing the hydrophilicity of the tail portion. Furthermore, with respect to the effects of aromatic substitution, these compounds did not show similar trends to the Series-I compounds. In this series, the naked scaffold (51) and methyl substituted analogue (54) were found to be the most active, with MIC values of 53 and 54 µg mL$^{-1}$ against *S. auerus*, respectively. The presence of electron withdrawing groups in 52 and 53, reduced their activity (MIC values of 77 and 108 µg mL$^{-1}$, respectively) against *S. auerus*, with bromine again being found to be more favourable than fluorine in the case of the acid derivatives. On the other hand, acid derivatives 51, 52, 53, and 54 from series-II glyoxamides, displayed good MIC values with 66, 77, 67, and 68 µg mL$^{-1}$, respectively, against *E. coli*. In addition, compounds 55 and 56 exhibited MIC values of 17 and 19 µg mL$^{-1}$, respectively, against *E. coli*.

Lastly, the Series-III dipeptides were found to be some of the most active compounds synthesized. Again, it was found that the presence of bromine in the phenyl ring (62, 66) improved activity compared to the naked scaffold (61, 65), while the guanidinyl derivatives (65, 66) were also found to be more active than the corresponding quaternary ammonium salts (61, 62). Compound 66, containing both a bromo-substituent on the phenyl ring and guanidinium salt, displayed the highest activity of the Series-III compounds with an MIC value of 10 µg mL$^{-1}$ against *S. auerus* and moderate activity against *E. coli* with an MIC value of 50 µg mL$^{-1}$. Similarly, compound 65, with the naked phenyl ring and guanidinium salt, also displayed good antimicrobial activity against *S. aureus* 18 µg mL$^{-1}$ but diminished activity against *E. coli*, with an MIC value of 90 µg mL-1. Interestingly, the bromo-substituted ammonium salt 62 also displayed good activity, with MICs of 23 and 21 µg ml$^{-1}$, against *S. aureus* and *E. coli*, respectively.

Overall, the guanidine-embedded glyoxamide derivatives displayed an interesting structure activity relationship (SAR) regarding their antimicrobial activity against *S. aureus* and *E. coli*. Generally, the presence of a bromine substituent on the phenyl ring improved activity. A short 3-carbon linker or dipeptide moiety was better than a single peptide linker, while the hydrolysed acids were more active than their corresponding methyl esters against *S. aureus*. Compounds with monopeptide acids and dipeptide esters were more active than with 3-carbon linkers and monopetide acids against *E. coli*. Further, the incorporation of a guanidinium salt improved antimicrobial activity compared to the corresponding quaternary ammonium salt.

Antibiofilm Activity

Figure 2:
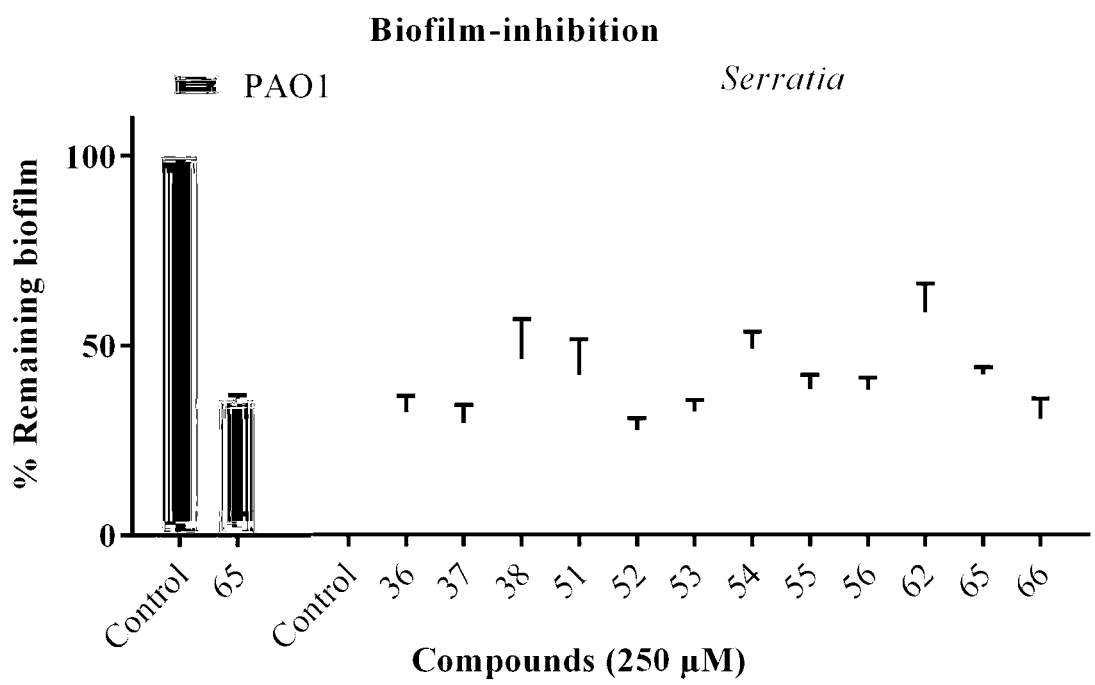
FIG. 2 shows graphs of the "% Remaining biofilm" (i.e. the percentage of biofilm adhered on polystyrene substratum relative to the control as quantified by crystal violet staining) for *Pseudomonas aeruginosa* (PAO1) or *S. marcescens* after 24 h treatment with 250 µM of glyoxamide-based peptidomimetics. The control represents the established biofilms without any compounds. Error bars indicate the standard error of the mean (SEM) of three independent experiments.

The biofilm disruption activities of the compounds were investigated using crystal violet staining according to a previously published protocol (G. A. O'Toole, *J Vis Exp*, 2011, (47), pii: 2437, DOI: 10.3791/2437, 2437). The ability of compounds (34-38, 51-56, 61, 62, 65 and 66) to disrupt the established biofilms of the Gram-positive bacteria *S. aureus* and the Gram-negative bacteria *Pseudomonas aeruginosa, Serratia marcescens* and *E. coli*, was determined at a concentration of 250 µM. In this assay, bacterial cultures were grown on a polystyrene substratum overnight prior to treatment with the compounds. In addition, the ability of these compounds to inhibit the formation of biofilms of *P. aeruginosa* and *S. marcescens* was also investigated at 250 µM, whereby the bacterial cultures were grown in the presence of test compounds. The results for compounds that exhibited more than 40% biofilm disruption are depicted in FIG. 1 (established biofilms) and FIG. 2 (inhibition of biofilm formation). FIG. 1 shows the disruption of established biofilms after 24 h treatment with 250 µM of glyoxamide-based peptidomimetics; the control represents the pre-established biofilms without any compounds (error bars indicate the standard error of the mean (SEM) of three independent experiments). FIG. 2 shows the inhibition of the formation of biofilms after 24 h treatment with 250 µM of glyoxamide-based peptidomimetics; the control represents the established biofilms without any compounds (error bars indicate the standard error of the mean (SEM) of three independent experiments).

Overall, the three series of glyoxamide derivatives exhibited low to excellent levels of disruption against the established biofilms of Gram-positive and Gram-negative bacteria (FIG. 1). Despite having some of the most potent antibacterial activity, the Series-I compounds (34-38) showed less effects on the integrity of the biofilms than other compounds tested. Compound 35 (a bromo derivative) was able to disrupt the established biofilms of *S. marcescens* and *E. coli* by 49% and 46%, respectively, while compounds 36 (a chloro derivative) and 37 (a fluoro derivative) were able to reduce the established biofilms of *E. coli* by 43% and 53%, respectively.

Despite having moderate MIC values, the Series-II compounds showed better biofilm disruption activities, and the acids (51-54) possessed superior activity to the esters (55-56). Compound 52 (the bromo substituent) exhibited good biofilm disruption of 42% against *S. aureus*, while compound 53 (the fluoro substituent) showed broad-spectrum biofilm disruption activities, with 46%, 42% and 40% disruption against *S. aureus, P. aeruginosa* and *S. marcescens*, respectively. Furthermore, compound 51 showed 48% disruption against *S. marcescens*, while compound 54 displayed 46% disruption against *P. aeruginosa* biofilms.

The Series-III compounds displayed the greatest levels of biofilm disruption against both the Gram-positive and Gram-negative strains. Compound 61, with an unsubstituted phenyl ring and two ammonium salts, was able to disrupt the established biofilms of *S. aureus* and *P. aeruginosa* by 53% and 55% respectively. The incorporation of a bromine to give compound 62 resulted in the compound with broadest activity. Compound 62 exhibited the highest levels of disruption towards *S. aureus* (61%), while it also showed good levels of disruption towards *P. aeruginosa, S. marcescens* and *E. coli*, with values of 46%, 49% and 42%, respectively. The guanidinium analogues 65 (unsubstituted) and 66 (bromo substituent) were more active than their counterparts 62 and 63 against *S. aureus* (55% and 52% disruption, respectively), but less active than them against *P. aeruginosa* (45% and 54%, respectively).

Figure 3:
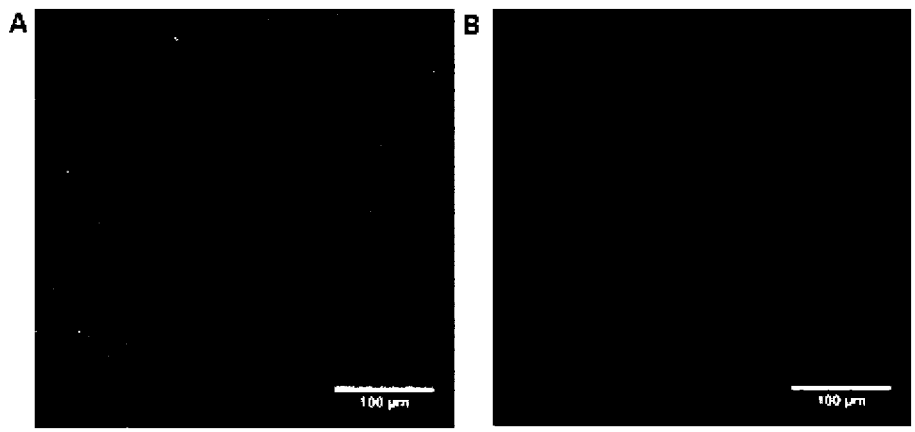
FIG. 3 shows images of established biofilms in *S. aureus* produced by confocal microscopy. Live bacteria (green), dead bacteria (red). Confocal microscopy images of *S. aureus* biofilms showing (A) Non-treated biofilm and (B) treated biofilm with compound 62 at 250 µM concentration.
Figure 4:
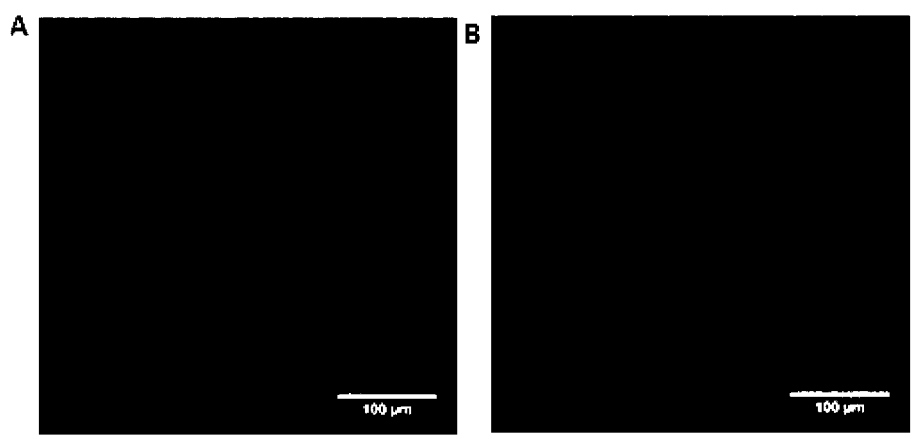
FIG. 4 shows images of non-established biofilms in *S. marcescens* produced by confocal microscopy. Live bacteria (green), dead bacteria (red). Confocal microscopy images of *S. marcescens* biofilms showing (A) Non-treated biofilm and (B) treated biofilm with compound 65 at 250 µM concentration.

When the compounds ability to inhibit biofilm formation was examined, only compound 65 displayed significant activity against *P. aeruginosa*, with 65% inhibition at 250 µM (FIG. 4). Interestingly, all Series of guanidine-embedded glyoxamide compounds exhibited moderate to high inhibition of non-established biofilms in *S. marcescens*. The Series-I compounds 36 (chloro derivative) and 37 (fluoro derivative) displayed superior biofilm inhibition ability with 71 and 74%, respectively. Similarly, almost all Series-II compounds exhibited inhibition levels above 50%, with compound 52 being the strongest compound in this assay, exhibiting 72% inhibition against *S. marcescens* at 250 µM. In addition, compounds 53 and 56 also performed well, with 67%, and 61% inhibition, respectively. The Series-III compounds also performed well, with compound 66 (bromo-substituent) displaying 69% inhibition of biofilm formation by *S. marcescens*. To confirm the biofilm disruption against *S. aureus* and biofilm inhibition against *S. marcescens*, the confocal microscopic images were obtained (FIG. 3 and FIG. 4). FIG. 3 shows images of established biofilms in *S. aureus* produced by confocal microscopy (live bacteria (green), dead bacteria (red)); confocal microscopy images of *S. aureus* biofilms showing (A) Non-treated biofilm and (B) treated biofilm with compound 62 at 250 µM concentration. FIG. 4 shows images of non-established biofilms in *S. marcescens* produced by confocal microscopy (live bacteria (green), dead bacteria (red)); confocal microscopy images of *S. marcescens* biofilms showing (A) Non-treated biofilm and (B) treated biofilm with compound 65 at 250 µM concentration. The treated biofilm (B) in FIG. 3 showed that the tested compound disrupted the pre-established biofilm significantly, with biofilm (B) having a much higher proportion of disrupted biofilms with dead bacteria and a lower proportion of live bacteria than the control (A). FIG. 4 showed that the tested compound inhibited biofilm formation. The control (A) represents the non-treated biofilms, with biofilm (B) having a much higher proportion of dead bacteria and a lower proportion of live bacteria than the control (A).

Toxicity Assay

Figure 5:
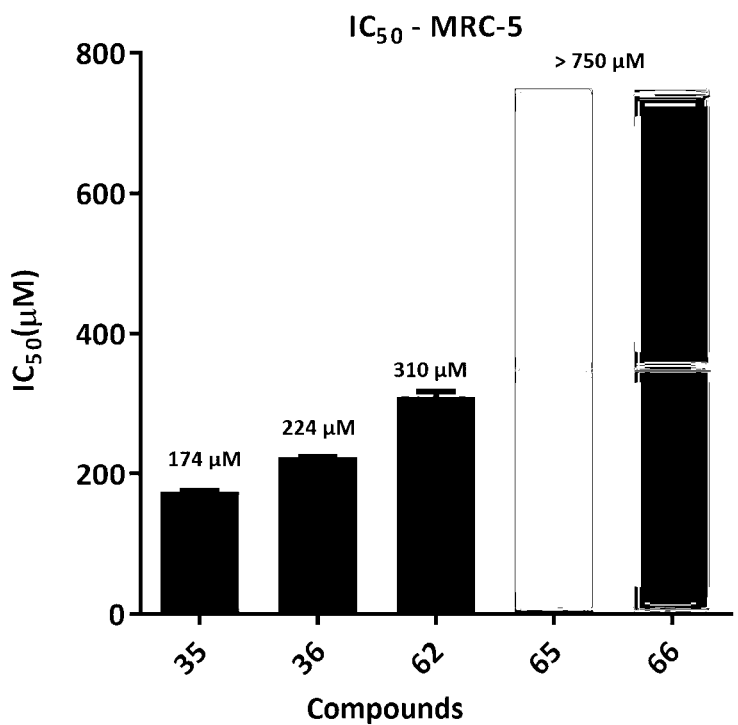
FIG. 5 is a graph of the toxicity ($IC_{50}$) of glyoxamide derivatives (35, 36, 62, 65 and 66) against MRC-5 human fibroblast cells. Concentration of compounds was tested between 150-750 µM. Error bars represent the mean of minimum three independent experiments±Standard error of the mean (SEM).
Figure 6:
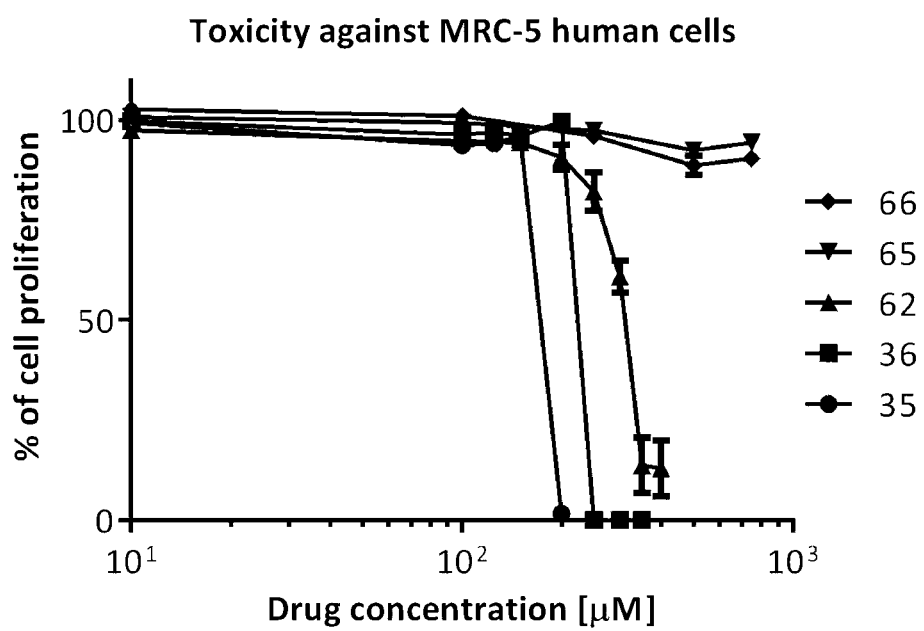
FIG. 6 shows a graph of percentage cell proliferation of MRC-5 normal human lung fibroblasts after 72 h incubation with compounds 35, 36, 62, 65 and 66, relative to a DMSO control. Points represent the mean of at least three individual experiments±Standard error of the mean (SEM).

To further evaluate the utility of these novel guanylated peptidomimetics for medical applications, it was essential to determine their specificity towards bacterial cells over mammalian cells. Therefore, the in vitro toxicity of the most active compounds (35, 36, 62, 65 and 66) was determined against MRC-5 normal human lung fibroblasts using the Alamar blue (Resazurin) assay (J. O'Brien, I. Wilson, T. Orton and F. Pognan, *Eur. J. Biochem.*, 2000, 267, 5421-5426). A dose-response curve was generated for each compound (FIG. 6) at concentrations ranging from 1-750 µM and the $IC_{50}$ values determined (FIG. 5). FIG. 5 shows toxicity ($IC_{50}$) of the most active glyoxamide derivatives (35, 36, 62, 65 and 66) against MRC-5 human fibroblast cells; concentration of compounds was tested between 150-750 µM (error bars represent the mean of minimum three independent experiments±Standard error of the mean (SEM)). FIG. 6 shows in vitro anti-proliferative properties of compounds 35, 36, 62, 65 and 66 against MRC-5 normal human lung fibroblasts after 72 h incubation, relative to a DMSO control (points represent the mean of at least three individual experiments±Standard error of the mean (SEM)).

All the tested compounds showed little toxicity towards the mammalian cells, even at 10 times their MIC value. The Series-I compounds 35 and 36 were found to have the lowest $IC_{50}$ values (174 µM and 224 µM, respectively), which is more than 14 times their equivalent MIC values of 12.5 µM and 16 µM, respectively. In addition, compounds 65 (MIC=31 µM) and 66 (MIC=15.7 µM) showed greater than 24 and 48 fold lower toxicity to MRC-5 mammalian cells, not reaching a 50% reduction of cell viability at the highest tested dose.

Membrane Conduction

Figure 7:
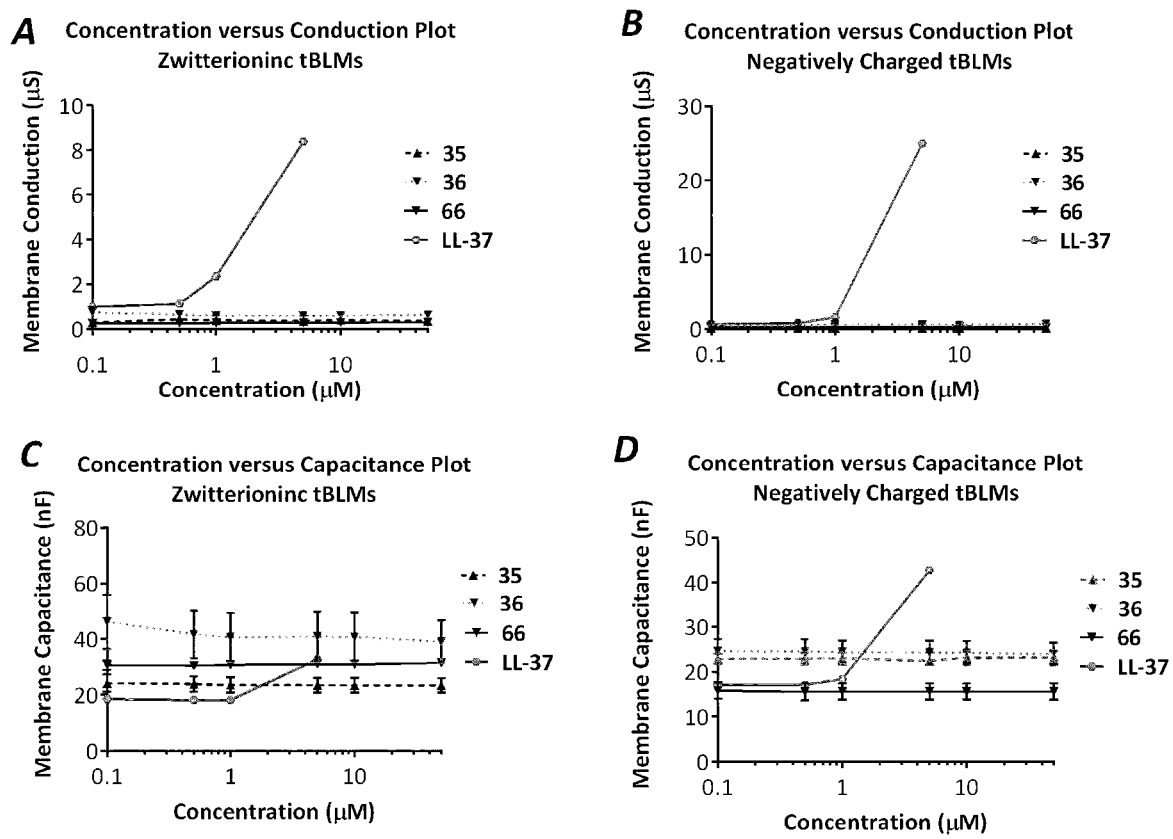
FIG. 7 shows graphs of membrane capacitance (nF) versus concentration of compounds (35, 36 and 66) and LL-37 on tethered bilayer lipid membranes (tBLMS): (A) in zwitterionic mammalian-like tBLMs; (B) in bacteria-like tBLMS containing 30% negatively charged POPG lipid tBLMs; (C) in zwitterionic mammalian-like tBLMs; and (D) in bacteria-like tBLMS containing 30% negatively charged POPG lipid tBLMs.

As compounds (35, 36 and 66) demonstrated promise as small molecular antimicrobial peptide mimics (SMAMPs), with very low levels of mammalian cell toxicity, the inventors further chose to identify whether their actions against bacteria were via a pore-forming mechanism. To do this, the inventors employed tethered bilayer lipid membranes in association with AC electrical impedance spectroscopy. FIG. 7 shows the impact of compounds (35, 36 and 66) on tethered bilayer lipid membranes (tBLMS): A: Conductance changes in response to increasing concentrations of the compounds compared to LL-37 in zwitterionic mammalian-like tBLMs; B: Conductance changes in response to increasing concentrations of the compounds compared to LL-37 in bacteria-like tBLMS containing 30% negatively charged POPG lipid tBLMs; C: Capacitance changes in response to increasing concentrations of the compounds compared to LL-37 in zwitterionic mammalian-like tBLMs; D: Capacitance changes in response to increasing concentrations of the compounds compared to LL-37 in bacteria-like tBLMS containing 30% negatively charged POPG lipid tBLMs;

As can be seen in FIG. 7A, these compounds exhibit little evidence that they are pore formers in mammalian-like zwitterionic diphytanyl containing membranes, especially when compared to the human defensin LL-37 (see J. Turner, Y. Cho, N.-N. Dinh, A. J. Waring and R. I. Lehrer, *Antimicrob. Agents Chemother.*, 1998, 42, 2206-2214). In the presence of membranes containing the negatively charged lipid POPG, which is common in many bacterial membranes (see K. Murzyn, T. Róg and M. Pasenkiewicz-Gierula, *Biophys. J.*, 2005, 88, 1091-1103), there is also little evidence of an increase in conduction with increased concentration when compared to LL-37 (FIG. 7B). Likewise, their interaction with the membranes exhibited little variation in membrane capacitances (FIG. 7A and FIG. 7B) indicating that the compounds did not alter membrane thickness and/or the relative dielectric moment of the membrane that can occur by the introduction of water molecules (see C. G. Cranfield, B. A. Cornell, S. L. Grage, P. Duckworth, S. Carne, A. S. Ulrich and B. Martinac, *Biophys. J.*, 2014, 106, 182-189). Taken together, the data suggests that the mechanism of action against bacteria of theses compounds is not the induction of cell lysis via membrane pore formation.

Conclusion for Example 1

The inventors have developed mono- and bis-guanidine-embedded glyoxamide derivatives with mono- and di-peptides. The compounds can be prepared by reactions of N-naphthoylisatins with amines and amino acids (e.g. ring-opening reactions). The replacement of quaternary ammonium salts with guanidinium salts proved to be an effective strategy for increasing the antibacterial activity of the glyoxamide scaffold, as was the incorporation of additional peptide moieties. Compounds 35, 36 and 66 exhibited MIC values of 6, 8 and 10 µg mL$^{-1}$, respectively, against *S. aureus*. In addition, these compounds also exhibited the ability to disrupt biofilms. Compound 65 was able to disrupt biofilms of *S. aureus*, *P. aeruginosa*, and *S. marcescens* by 61%, 61%, and 60% respectively at 250 µM. Compound 66 was able to disrupt the biofilms of *S. aureus*, and *P. aeruginosa* by 64%, 55% respectively, at 250 µM. Compound 52 was able to inhibit the formation of biofilms by *S. marcescens* by 72% and compound 65 by 65% against *P. aeruginosa* at 250 µM. Furthermore, in vitro toxicity against human MRC-5 fibroblast cells demonstrated that these compounds possess selective toxicity against bacterial cells over mammalian cells with 14-48 fold higher concentrations needed to inhibit the growth of mammalian cells over the bacterial cells. Results from tethered bilayer lipid membrane experiments suggest that the mechanism of action of these compounds is not as the result of inducing membrane pore formation which could lead to cell lysis. The antibacterial and antibiofilm activity of guanidine-embedded amphipathic glyoxamide-based SMAMPs suggest that these compounds would be useful in clinic and industry to treat the various bacterial infections or reduce biofilm formation.

Example 2

Synthesis of Sulfonamide Compounds 24a, 38b, 42d and 43d

General Synthetic Procedure 5.1.A for N-Sulfonyl Isatin Compounds

To a solution of appropriate isatin (1 equivalent) in dichloromethane (10 mL) was added triethylamine (1.1 equivalents) at 0° C. under nitrogen atmosphere. The reaction mixture was stirred at 0° C. for 20 min. An appropriate sulfonyl chloride (1 equivalent) was added slowly to the reaction mixture at 0° C. The reaction mixture was then stirred at room temperature for 3-24 h. The resulting mixture was concentrated in vacuo and washed with methanol to afford the product.

General Synthetic Procedure 5.1.0 for Glyoxamide Derivatives and Boc-Protected Glyoxamides To a solution of sulfonyl isatin or aryl isatin (1 equivalent) in dichloromethane (5 mL) was added an appropriate amine (1 equivalent) at 0° C. under nitrogen atmosphere. The reaction mixture was stirred at room temperature for 1-24 h. After completion of the reaction, water was added to the reaction mixture and the product was extracted into dichloromethane (3×30 mL), washed with brine, dried over anhydrous sodium sulfate and concentrated in vacuo to afford the product.

General Synthetic Procedure 5.1.D for Hydrochloride and Iodide Salts

To a solution of glyoxamide derivative (1 equivalent) in dichloromethane, tetrahydrofuran or diethyl ether was added 4 M HCl/dioxane (5.0 equivalents) or iodomethane (2.5 equivalents). The reaction mixture was stirred at room temperature for 20 min to 48 h. After completion of reaction, the reaction mixture was concentrated in vacuo, washed with diethyl ether and freeze-dried to afford the product.

General Synthetic Procedure 5.1.E for Aminoglyoxamides

To a solution of Boc-protected glyoxamide (1 equivalent) in dichloromethane (10 mL) was added 4 M HCl/dioxane (3.0 mL). The reaction mixture was stirred at room temperature for 18 h. After completion of reaction, the reaction mixture was concentrated in vacuo and washed with diethyl ether to afford the product.

General Synthetic Procedure 5.1.F for Boc-Protected Guanidine Glyoxamides

To a solution of aminoglyoxamides (1 equivalent) and N,N'-di-Boc-1H-pyrazole-1-carboxamidine (1.2 equivalents) in dichloromethane or acetonitrile (10 mL) was added triethylamine (2.5 equivalents) at 0° C. under nitrogen atmosphere. The reaction mixture was stirred at room temperature for 15-18 h. After completion of the reaction, the mixture was filtered, followed by concentrating in vacuo. The product was purified by flash chromatography on silica using ethyl acetate/n-hexane (1:4) as eluent to afford the product.

General Synthetic Procedure 5.1.G for Guanidine Hydrogen Chloride Salts

To a solution of Boc-protected guanidine glyoxamide (1 equivalent) in dichloromethane (1 mL) was added trifluoroacetic acid (1 mL). The reaction mixture was stirred at room temperature for 2 h. After completion of the reaction, the reaction mixture was concentrated in vacuo and washed with diethyl ether. To the residue in dichloromethane (1 mL) was added 4 M HCl/dioxane (1.0 mL). The reaction mixture was stirred at room temperature for 30 min. After completion of reaction, the reaction mixture was concentrated in vacuo and washed with diethyl ether to afford the product.

2-(5-Bromo-2-(octylsulfonamido)phenyl)-N-(3-(dimethylamino)propyl)-2-oxoacetamide (24a)

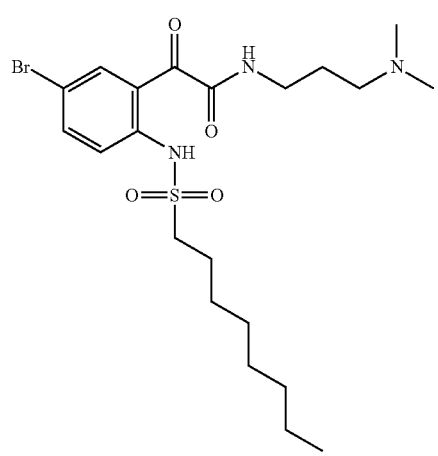

The title compound 24a was synthesised from 5-bromo-1-(octylsulfonyl)indoline-2,3-dione 14a (0.15 g, 0.39 mmol) and N,N-dimethylpropane-1,3-diamine (49 µL, 0.39 mmol) following general procedure 5.1.C. Reaction stirred for 18 h. The product 24a was obtained as a yellow oil (0.37 g, 97%); $^1$H NMR (400 MHz, CDCl$_3$): δ 8.89 (bs, 1H, NH), 8.62 (t, J=1.3 Hz, 1H, ArH), 7.69-7.66 (m, 2H, ArH), 3.52 (t, J=6.0 Hz, 2H, CH$_2$), 3.15-3.10 (m, 2H, CH$_2$), 2.56 (t, J=6.1 Hz, 2H, CH$_2$), 2.34 (s, 6H, CH$_3$), 1.84-1.73 (m, 4H, CH$_2$), 1.40-1.18 (m, 10H, CH$_2$), 0.86 (t, J=6.6 Hz, 3H, CH$_3$); $^{13}$C NMR (100 MHz, CDCl$_3$): δ 190.8 (CO), 162.2 (CO), 140.8 (ArC), 139.1 (ArCH), 137.4 (ArCH), 120.9 (ArC), 120.0 (ArCH), 115.4 (ArC), 58.8 (CH$_2$), 52.8 (CH$_2$), 45.2 (CH$_3$), 40.0 (CH$_2$), 31.8 (CH$_2$), 29.1 (CH$_2$), 29.0 (CH$_2$), 28.2 (CH$_2$), 25.1 (CH$_2$), 23.5 (CH$_2$), 22.7 (CH$_2$), 14.2 (CH$_3$); IR (ATR): ν$_{max}$ 3258, 3049, 2922, 2853, 2521, 2112, 1897, 1650, 1529, 1460, 1388, 1287, 1146, 1194, 1099, 972, 915, 823, 710 cm$^{-1}$; UV-Vis (MeOH): λ$_{max}$ 231 nm (ε 24,100 cm$^{-1}$M$^{-1}$), 343 (1,610); HRMS (+ ESI): Found m/z 504.1528 [M+H]$^+$, C$_{21}$H$_{35}$BrN$_3$O$_4$S required 504.1526.

5-Bromo-1-(octylsulfonyl)indoline-2,3-dione (14a)

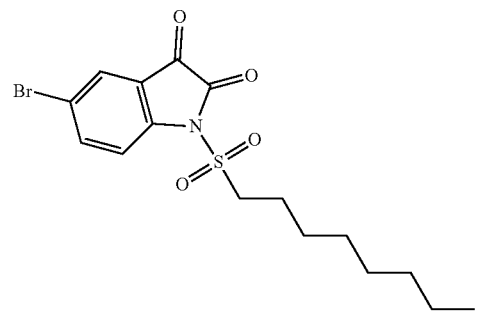

The title compound 14a was synthesised from 5-bromoisatin (1.06 g, 4.22 mmol), triethylamine (0.65 mL, 4.66 mmol) and octane-1-sulfonyl chloride (0.85 mL, 4.21 mmol) following general synthetic procedure 5.1.A. Reaction stirred for 4 h. The product 14a was obtained as a yellow solid (0.96 g, 51%), mp 138.0-140.1° C.; $^1$H NMR (400 MHz, DMSO-d$_6$): δ 7.96-7.85 (m, 2H, ArH), 7.70-7.60 (m, 1H, ArH), 3.66-3.53 (m, 2H, CH$_2$), 1.83-1.72 (m, 2H, CH$_2$), 1.43-1.16 (m, 10H, CH$_2$), 0.89-0.79 (m, 3H, CH$_3$); $^{13}$C NMR (100 MHz, DMSO-d$_6$): δ 177.5 (CO), 156.0 (CO), 145.7 (ArC), 139.6 (ArCH), 127.1 (ArCH), 121.4 (ArC), 117.2 (ArC), 116.1 (ArCH), 53.7 (CH$_2$), 31.1 (CH$_2$), 28.4 (CH$_2$), 28.3 (CH$_2$), 27.3 (CH$_2$), 22.1 (CH$_2$), 22.0 (CH$_2$), 13.9 (CH$_3$); IR (ATR): ν$_{max}$ 3063, 2914, 2849, 2341, 2112, 1740, 1594, 1458, 1370, 1174, 1137, 1268, 1114, 1061, 936, 844, 720, 783 cm$^{-1}$; UV-Vis (ACN): λ$_{max}$ 223 nm (ε 18,600 cm$^{-1}$ M$^{-1}$), 244 (20,400), 291 (4,800), 402 (748).

2-(2-(5-Bromo-2-(octylsulfonamido)phenyl)-2-oxoacetamido)-N,N-dimethylethan-1-aminium chloride (38b)

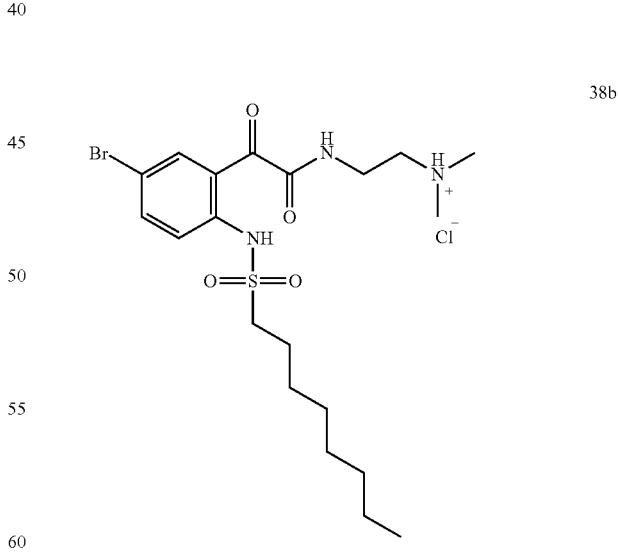

The title compound 38b was synthesised from 2-(5-bromo-2-(octylsulfonamido)phenyl)-N-(2-(dimethylamino)ethyl)-2-oxoacetamide 38a (20 mg, 0.041 mmol) and 4 M HCl/dioxane (0.10 mL, 0.40 mmol) in diethyl ether (10 mL) following general procedure 5.1.D. Reaction stirred for 20 min. The product 38b was obtained as a white sticky solid (19 mg, 88%); $^1$H NMR (400 MHz, DMSO-d$_6$): δ 10.24 (bs, 1H, NH), 9.99 (bs, 1H, NH), 9.09 (t, J=5.8 Hz, 1H, NH), 7.99 (d, J=2.4 Hz, 1H, ArH), 7.84 (dd, J=8.8, 2.5 Hz, 1H, ArH), 7.44 (d, J=8.8 Hz, 1H, ArH), 3.58 (q, J=6.0 Hz, 2H, CH$_2$), 3.29-3.23 (m, 2H, CH$_2$), 3.20-3.13 (m, 2H, CH$_2$), 2.81 (s, 6H, CH$_3$), 1.69-1.59 (m, 2H, CH$_2$), 1.37-1.16 (m, 10H, CH$_2$), 0.84 (t, J=6.6 Hz, 3H, CH$_3$); $^{13}$C NMR (100 MHz, DMSO-d$_6$): δ 189.0 (CO), 162.4 (CO), 137.2 (ArC), 136.7 (ArCH), 134.2 (ArCH), 128.4 (ArC), 124.6 (ArCH), 116.2 (ArC), 55.1 (CH$_2$), 51.6 (CH$_2$), 42.3 (CH$_3$), 34.2 (CH$_2$), 31.1 (CH$_2$), 28.4 (CH$_2$), 28.3 (CH$_2$), 27.3 (CH$_2$), 22.8 (CH$_2$), 22.0 (CH$_2$), 13.9 (CH$_3$); IR (ATR): ν$_{max}$ 3258, 2922, 2852, 2695, 2106, 1671, 1529, 1488, 1389, 1331, 1199, 1140, 1093, 1019, 914, 830, 764, 700 cm$^{-1}$; UV-Vis (H$_2$O): λ$_{max}$ 231 nm (ε 15,000 cm$^{-1}$M$^{-1}$); HRMS (+ ESI): Found m/z 490.1373 [M+H]$^+$, C$_{20}$H$_{33}$BrN$_3$O$_4$S required 490.1370.

2-(5-Bromo-2-(octylsulfonamido)phenyl)-N-(2-(dimethylamino)ethyl)-2-oxoacetamide (38a)

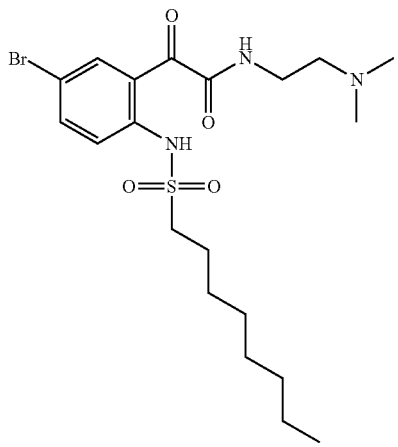

The title compound 38a was synthesised from 5-bromo-1-(octylsulfonyl)indoline-2,3-dione 14a (0.16 g, 0.39 mmol) and N,N-dimethylethane-1,2-diamine (43 µL, 0.39 mmol) following general synthetic procedure 5.1.C. Reaction stirred for 24 h. The product 38a was obtained as a yellow oil (0.19 g, 97%); $^1$H NMR (400 MHz, CDCl$_3$): δ 8.68-8.65 (m, 1H, ArH), 7.70-7.66 (m, 2H, ArH), 7.53 (bs, 1H, NH), 3.50 (q, J=5.4 Hz, 2H, CH$_2$), 3.17-3.10 (m, 2H, CH$_2$), 2.57 (t, J=5.9 Hz, 2H, CH$_2$), 2.32 (s, 6H, CH$_3$), 1.82-1.72 (m, 2H, CH$_2$), 1.40-1.18 (m, 10H, CH$_2$), 0.86 (t, J=6.6 Hz, 3H, CH$_3$); $^{13}$C NMR (100 MHz, CDCl$_3$): δ 190.3 (CO), 162.0 (CO), 141.0 (ArC), 139.3 (ArCH), 137.5 (ArCH), 120.5 (ArC), 119.8 (ArCH), 115.3 (ArC), 57.3 (CH$_2$), 52.9 (CH$_2$), 45.2 (CH$_3$), 37.0 (CH$_2$), 31.8 (CH$_2$), 29.0 (CH$_2$), 29.0 (CH$_2$), 28.2 (CH$_2$), 23.5 (CH$_2$), 22.7 (CH$_2$), 14.2 (CH$_3$); IR (ATR): ν$_{max}$ 3054, 2292, 2853, 2386, 2102, 1649, 1525, 1460, 1388, 1331, 1285, 1193, 1146, 1099, 971, 913, 824, 711 cm$^{-1}$; UV-Vis (MeOH): λ$_{max}$ 232 nm (ε 17,000 cm$^{-1}$M$^{-1}$), 344 (1,500); HRMS (+ ESI): Found m/z 490.1373 [M+H]$^+$, C$_{20}$H$_{33}$BrN$_3$O$_4$S required 490.1370.

N-(3-Guanidinopropyl)-2-(2-(octylsulfonamido)phenyl)-2-oxoacetamide hydrochloride (42d)

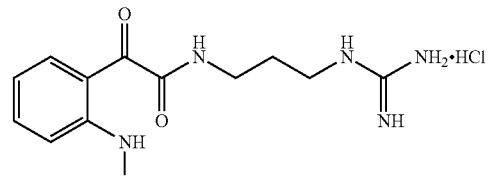

The title compound 42d was synthesised from (E)-1-tert-butyl-N—(N'-((tert-butyloxidanyl)carbonyl)-N-(3-(2-(2-(o-ctylsulfonamido)phenyl)-2-oxoacetamido)propyl)carbamimidoyl)-1-oxidanecarboxamide 42c (31 mg, 0.065 mmol) following general procedure 5.1.G. Reaction stirred for 20 h. The product 42d was obtained as a yellow sticky solid (22 mg, 71%); $^1$H NMR (400 MHz, DMSO): δ 10.27 (bs, 1H, NH), 8.98 (bs, 1H, NH), 7.80-7.67 (m, 3H, NH, ArH), 7.56 (d, J=8.2 Hz, 1H, ArH), 7.49-7.03 (m, 5H, NH), 3.32-3.14 (m, 6H, CH$_2$), 1.82-1.60 (m, 4H, CH$_2$), 1.38-1.15 (m, 10H, CH$_2$), 0.83 (t, J=6.6 Hz, 3H, CH$_3$); $^{13}$C NMR (100 MHz, CDCl$_3$): δ 193.4 (CO), 164.3 (CO), 157.0 (CN), 139.6 (ArC), 135.6 (ArCH), 133.2 (ArCH), 123.6 (ArCH), 122.4 (ArC), 120.1 (ArCH), 51.4 (CH$_2$), 38.3 (CH$_2$), 36.2 (CH$_2$), 31.1 (CH$_2$), 28.3 (CH$_2$), 28.3 (CH$_2$), 28.3 (CH$_2$), 27.2 (CH$_2$), 22.9 (CH$_2$), 22.0 (CH$_2$), 13.9 (CH$_3$); IR (ATR): ν$_{max}$ 3158, 2922, 2340, 2110, 1637, 1490, 1450, 1398, 1332, 1222, 1144, 1019, 912, 829, 756, 672 cm$^{-1}$; UV-Vis (H$_2$O): λ$_{max}$ 263 nm (ε 3,540 cm$^{-1}$M$^{-1}$); HRMS (+ ESI): Found m/z 440.2327 [M+H]$^+$, C$_{20}$H$_{34}$N$_5$O$_4$S required 440.2326.

(E)-1-tert-Butyl-N—(N'-((tert-butyloxidanyl)carbonyl)-N-(3-(2-(2-(octylsulfonamido)phenyl)-2-oxoacetamido)propyl)carbamimidoyl)-1-oxidanecarboxamide (42c)

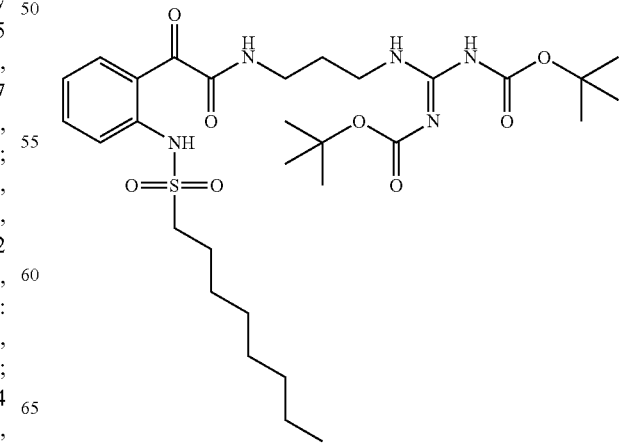

The title compound 42c was synthesised from N-(3-aminopropyl)-2-(2-(octylsulfonamido)phenyl)-2-oxoacetamide hydrochloride 42b (0.18 g, 0.42 mmol), triethylamine (0.15 mL, 1.05 mmol) and N,N'-di-Boc-1H-pyrazole-1-carboxamidine (0.13 g, 0.42 mmol) in dichloromethane (10 mL) following general synthetic procedure 5.1.F. Reaction stirred for 18 h. The product 42c was obtained as a yellow oil (66 mg, 33%); $^1$H NMR (400 MHz, CDCl$_3$): δ 11.46 (bs, 1H, NH), 10.63 (bs, 1H, NH), 8.61 (bs, 1H, NH), 8.55 (t, J=6.4 Hz, 1H, NH), 8.25 (dd, J=8.1, 1.5 Hz, 1H, ArH), 7.77 (dd, J=8.5, 0.8 Hz, 1H, ArH), 7.62-7.56 (m, 1H, ArH), 7.18-7.12 (m, 1H, ArH), 3.65-3.55 (m, 2H, CH$_2$), 3.46 (q, J=6.2 Hz, 2H, CH$_2$), 3.17-3.11 (m, 2H, CH$_2$), 1.86-1.74 (m, 4H, CH$_2$), 1.50 (s, 9H, CH$_3$), 1.41-1.18 (m, 19H, CH$_2$, CH$_3$), 0.85 (t, J=6.8 Hz, 3H, CH$_3$); $^{13}$C NMR (100 MHz, CDCl$_3$): δ 192.8 (CO), 163.9 (CO), 162.7 (CN), 157.2 (CO), 153.3 (CO), 142.1 (ArC), 136.5 (ArCH), 135.1 (ArCH), 122.5 (ArCH), 118.7 (ArC), 117.9 (ArCH), 83.9 (C), 80.1 (C), 52.7 (CH$_2$), 37.5 (CH$_2$), 35.8 (CH$_2$), 31.8 (CH$_2$), 30.0 (CH$_2$), 29.1 (CH$_2$), 29.0 (CH$_2$), 28.3 (CH$_2$), 28.2 (CH$_3$), 28.2 (CH$_3$), 23.5 (CH$_2$), 22.7 (CH$_2$), 14.2 (CH$_3$); IR (ATR): ν$_{max}$ 3323, 3187, 2927, 2322, 2092, 1720, 1637, 1489, 1408, 1326, 1215, 1129, 1049, 907, 806, 754, 671 cm$^{-1}$; UV-Vis (MeOH): λ$_{max}$ 229 nm (ε 69,000 cm$^{-1}$M$^{-1}$), 268 (16,000), 334 (5,800); HRMS (+ ESI): Found m/z 640.3378 [M+H]$^+$, C$_{30}$H$_{50}$N$_5$O$_8$S required 640.3375.

N-(3-Aminopropyl)-2-(2-(octylsulfonamido)phenyl)-2-oxoacetamide hydrochloride (42b)

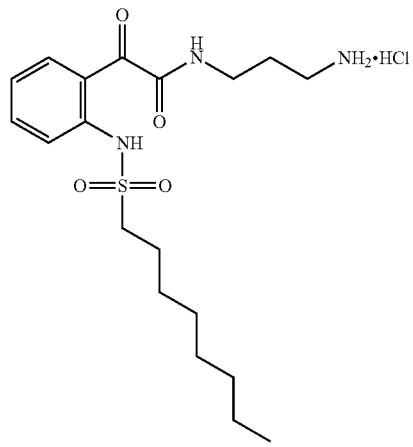

The title compound 42b was synthesised from tert-butyl (3-(2-(2-(octylsulfonamido)phenyl)-2-oxoacetamido)propyl)carbamate 42a (0.30 g, 0.61 mmol) following general synthetic procedure 5.1.E. The product 42b was obtained as a yellow sticky solid (0.22 g, 82%); $^1$H NMR (400 MHz, DMSO): δ 10.27 (bs, 1H, NH), 9.03 (t, J=5.9 Hz, 1H, NH), 8.01 (bs, 3H, NH), 7.78 (dd, J=7.9, 1.5 Hz, 1H, ArH), 7.73-7.67 (m, 1H, ArH), 7.56 (dd, J=8.3, 0.6 Hz, 1H, ArH), 7.33-7.27 (m, 1H, ArH), 3.35-3.29 (m, 2H, CH$_2$), 3.28-3.23 (m, 2H, CH$_2$), 2.90-2.79 (m, 2H, CH$_2$), 1.89-1.79 (m, 2H, CH$_2$), 1.70-1.60 (m, 2H, CH$_2$), 1.38-1.16 (m, 10H, CH$_2$), 0.84 (t, J=6.8 Hz, 3H, CH$_3$); $^{13}$C NMR (100 MHz, CDCl$_3$): δ 193.3 (CO), 164.3 (CO), 139.6 (ArC), 135.5 (ArCH), 133.2 (ArCH), 123.6 (ArCH), 122.5 (ArC), 120.2 (ArCH), 51.4 (CH$_2$), 36.7 (CH$_2$), 35.8 (CH$_2$), 31.1 (CH$_2$), 28.3 (CH$_2$), 28.3 (CH$_2$), 27.2 (CH$_2$), 26.9 (CH$_2$), 22.9 (CH$_2$), 22.0 (CH$_2$), 13.9 (CH$_3$); IR (ATR): ν$_{max}$ 3331, 3238, 2919, 2765, 2675, 2522, 2340, 2034, 1636, 1523, 1490, 1445, 1399, 1336, 1258, 1210, 1151, 958, 914, 850, 817, 753, 670 cm$^{-1}$; UV-Vis (H$_2$O): λ$_{max}$ 261 nm (ε 5,900 cm$^{-1}$M$^{-1}$); HRMS (+ ESI): Found m/z 398.2109 [M+H]$^+$, C$_{19}$H$_{32}$N$_3$O$_4$S required 398.2108.

tert-Butyl (3-(2-(2-(octylsulfonamido)phenyl)-2-oxoacetamido)propyl)carbamate (42a)

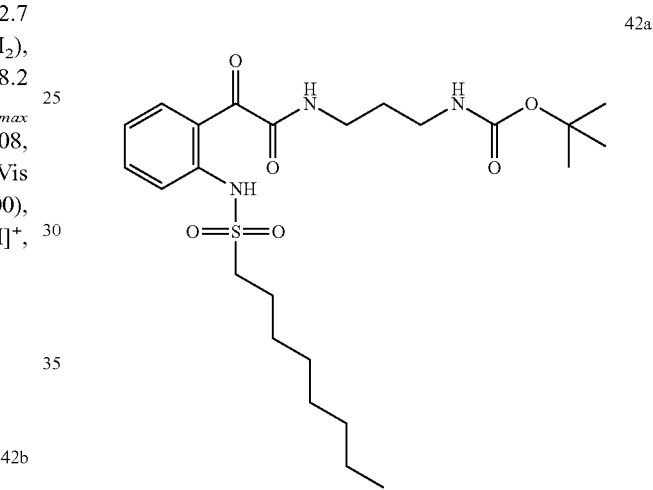

The title compound 42a was synthesised from 1-(octylsulfonyl)indoline-2,3-dione 11a (0.22 g, 0.68 mmol) and tert-butyl (3-aminopropyl)carbamate (0.12 g, 0.71 mmol) following general synthetic procedure 5.1.C. Reaction stirred for 20 h. The product 42a was obtained as a yellow oil (0.33 g, 98%); $^1$H NMR (400 MHz, CDCl$_3$): δ 10.49 (bs, 1H, NH), 8.45 (d, J=8.0 Hz, 1H, ArH), 7.77 (d, J=8.5 Hz, 1H, ArH), 7.64-7.57 (m, 2H, ArH, NH), 7.18-7.12 (m, 1H, ArH), 4.84 (bs, 1H, NH), 3.46 (q, J=6.4 Hz, 2H, CH$_2$), 3.23 (q, J=6.1 Hz, 2H, CH$_2$), 3.18-3.12 (m, 2H, CH$_2$), 1.83-1.71 (m, 4H, CH$_2$), 1.44 (s, 9H, CH$_3$), 1.41-1.18 (m, 10H, CH$_2$), 0.85 (t, J=6.8 Hz, 3H, CH$_3$); $^{13}$C NMR (100 MHz, CDCl$_3$): δ 191.7 (CO), 163.1 (CO), 156.9 (CO), 142.1 (ArC), 136.7 (ArCH), 135.3 (ArCH), 122.6 (ArCH), 118.8 (ArC), 118.0 (ArCH), 79.8 (C), 52.7 (CH$_2$), 37.3 (CH$_2$), 36.4 (CH$_2$), 31.8 (CH$_2$), 30.2 (CH$_2$), 29.0 (CH$_2$), 29.0 (CH$_2$), 28.5 (CH$_3$), 28.2 (CH$_2$), 23.5 (CH$_2$), 22.7 (CH$_2$), 14.2 (CH$_3$); IR (ATR): ν$_{max}$ 3358, 2922, 2851, 2324, 2112, 1639, 1522, 1449, 1332, 1246, 1149, 1129, 1005, 916, 817, 753, 671 cm$^{-1}$; UV-Vis (MeOH): λ$_{max}$ 222 nm (ε 16,400 cm$^{-1}$M$^{-1}$), 267 (7,340), 335 (2,740); HRMS (+ ESI): Found m/z 520.2456 [M+Na]$^+$, C$_{24}$H$_{39}$N$_3$O$_6$SNa required 520.2452.

1-(Octylsulfonyl)indoline-2,3-dione (11a)

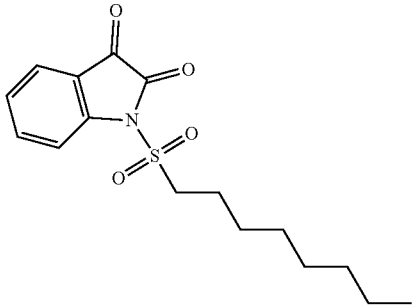

The title compound 11a was synthesised from isatin (1.06 g, 7.18 mmol), triethylamine (1.12 mL, 8.04 mmol) and octane-1-sulfonyl chloride (1.60 mL, 8.18 mmol) following general synthetic procedure 5.1.A. Reaction stirred for 3 h. The product 11a was obtained as a yellow solid (1.16 g, 50%); mp 119.7-124.3° C.; $^1$H NMR (400 MHz, DMSO-d$_6$): δ 7.78-7.70 (m, 3H, ArH), 7.36-7.29 (m, 1H, ArH), 3.65-3.57 (m, 2H, CH$_2$), 1.84-1.73 (m, 2H, CH$_2$), 1.41-1.16 (m, 10H, CH$_2$), 0.84 (t, J=7.0 Hz, 3H, CH$_3$); $^{13}$C NMR (100 MHz, DMSO-d$_6$): δ 178.7 (CO), 156.5 (CO), 146.9 (ArC), 137.9 (ArCH), 125.1 (ArCH), 125.0 (ArCH), 119.4 (ArC), 114.1 (ArCH), 53.7 (CH$_2$), 31.1 (CH$_2$), 28.4 (CH$_2$), 28.3 (CH$_2$), 27.3 (CH$_2$), 22.1 (CH$_2$), 22.0 (CH$_2$), 13.9 (CH$_3$); IR (ATR): ν$_m$ 2914, 2850, 2321, 2105, 1910, 1730, 1593, 1457, 1371, 1319, 1233, 1174, 1124, 1004, 930, 832, 754, 674 cm$^{-1}$; UV-Vis (ACN): λ$_{max}$ 211 nm (ε 22,500 cm$^{-1}$M$^{-1}$), 239 (22,500), 244 (18,300), 295 (8,340), 386 (1,010).

2-(5-Bromo-2-(octylsulfonamido)phenyl)-N-(3-guanidinopropyl)-2-oxoacetamide hydrochloride (43d)

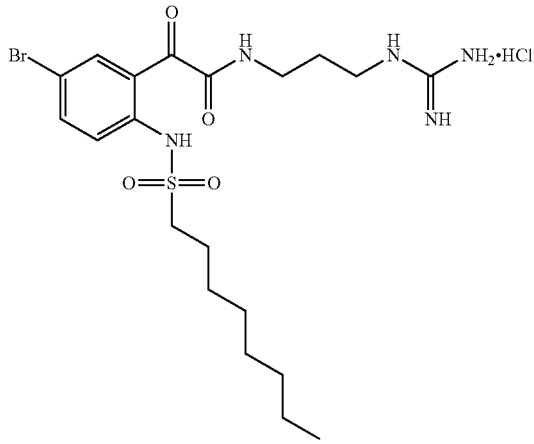

The title compound 43d was synthesised from (E)-N—(N-(3-(2-(5-bromo-2-(octylsulfonamido)phenyl)-2-oxoacetamido)propyl)-N'-((tert-butyloxidanyl)carbonyl)carbamimidoyl)-1-(tert-butyl)-oxidanecarboxamide 43c (30 mg, 0.042 mmol) following general synthetic procedure 5.1.G. The product 43d was obtained as a yellow sticky solid (17 mg, 72%); $^1$H NMR (600 MHz, DMSO): δ 10.07 (bs, 1H, NH), 8.94 (bs, 1H, NH), 7.91-7.82 (m, 2H, ArH), 7.64 (t, J=5.3 Hz, 1H, NH), 7.45 (d, J=8.7 Hz, 1H, ArH), 7.34 (bs, 2H, NH), 7.03 (bs, 2H, NH), 3.26 (q, J=6.6 Hz, 2H, CH$_2$), 3.20-3.15 (m, 4H, CH$_2$), 1.75-1.69 (m, 2H, CH$_2$), 1.66-1.60 (m, 2H, CH$_2$), 1.35-1.17 (m, 10H, CH$_2$), 0.84 (t, J=7.0 Hz, 3H, CH$_3$); $^{13}$C NMR (150 MHz, CDCl$_3$): δ 190.5 (CO), 163.0 (CO), 156.9 (CN), 137.7 (ArC), 137.0 (ArCH), 134.2 (ArCH), 127.6 (ArC), 124.2 (ArCH), 116.2 (ArC), 51.4 (CH$_2$), 38.3 (CH$_2$), 36.1 (CH$_2$), 31.1 (CH$_2$), 28.4 (CH$_2$), 28.3 (CH$_2$), 28.3 (CH$_2$), 27.3 (CH$_2$), 22.8 (CH$_2$), 22.0 (CH$_2$), 13.9 (CH$_3$); IR (ATR): ν$_{max}$ 3337, 3178, 2923, 2852, 2101, 1640, 1523, 1477, 1384, 1326, 1135, 1051, 1026, 902, 817, 770, 711 cm$^{-1}$; UV-Vis (H$_2$O): λ$_{max}$ 231 nm (ε 21,000 cm$^{-1}$M$^{-1}$), 368 (960); HRMS (+ ESI): Found m/z 518.1425 [M+H]$^+$, C$_{20}$H$_{33}$BrN$_5$O$_4$S required 518.1431.

(E)-N—(N-(3-(2-(5-Bromo-2-(octylsulfonamido)phenyl)-2-oxoacetamido)propyl)-N'((tert-butyloxidanyl)carbonyl)carbamimidoyl)-1-(tert-butyl)-oxidanecarboxamide (43c)

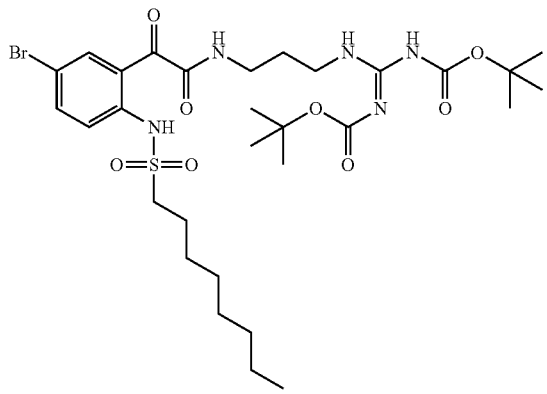

The title compound 43c was synthesised from N-(3-aminopropyl)-2-(5-bromo-2-(octylsulfonamido)phenyl)-2-oxoacetamide hydrochloride 43b (0.11 g, 0.20 mmol), triethylamine (70 µL, 0.50 mmol) and N,N'-di-Boc-1H-pyrazole-1-carboxamidine (72 mg, 0.23 mmol) in acetonitrile (10 mL) following general synthetic procedure 5.1.F. Reaction stirred for 15 h. The product 43c was obtained as a yellow oil (74 mg, 51%); $^1$H NMR (400 MHz, CDCl$_3$): δ 11.47 (bs, 1H, NH), 10.52 (bs, 1H, NH), 8.68 (t, J=5.9 Hz, 1H, NH), 8.52 (t, J=6.2 Hz, 1H, NH), 8.46 (d, J=2.0 Hz, 1H, ArH), 7.72-7.65 (m, 2H, ArH), 3.54 (q, J=6.4 Hz, 2H, CH$_2$), 3.44 (q, J=6.0 Hz, 2H, CH$_2$), 3.15-3.09 (m, 2H, CH$_2$), 1.83-1.72 (m, 4H, CH$_2$), 1.50 (s, 9H, CH$_3$), 1.40-1.19 (m, 19H, CH$_2$, CH$_3$), 0.86 (t, J=6.7 Hz, 3H, CH$_3$); $^{13}$C NMR (100 MHz, CDCl$_3$): δ 191.4 (CO), 163.1 (CO), 163.0 (CN), 157.5 (CO), 153.4 (CO), 141.1 (ArC), 139.2 (ArCH), 137.3 (ArCH), 120.0 (ArC), 119.6 (ArCH), 115.1 (ArC), 83.8 (C), 79.7 (C), 52.9 (CH$_2$), 37.1 (CH$_2$), 35.8 (CH$_2$), 31.8 (CH$_2$), 30.1 (CH$_2$), 29.0 (CH$_2$), 29.0 (CH$_2$), 28.3 (CH$_3$), 28.2 (CH$_2$), 28.2 (CH$_3$), 23.5 (CH$_2$), 22.7 (CH$_2$), 14.2 (CH$_3$); IR (ATR): ν$_{max}$ 3328, 3190, 2925, 2091, 1722, 1620, 1571, 1477, 1412, 1328, 1284, 1130, 1050, 1025, 903, 815, 767, 711 cm$^{-1}$; UV-Vis (MeOH): λ$_{max}$ 233 nm (ε 64,000 cm$^{-1}$M$^{-1}$), 368 (1,200); HRMS (+ ESI): Found m/z 718.2480 [M+H]$^+$, C$_{30}$H$_{49}$BrN$_5$O$_8$S required 718.2480.

N-(3-Aminopropyl)-2-(5-bromo-2-(octylsulfonamido)phenyl)-2-oxoacetamide hydrochloride (43b)

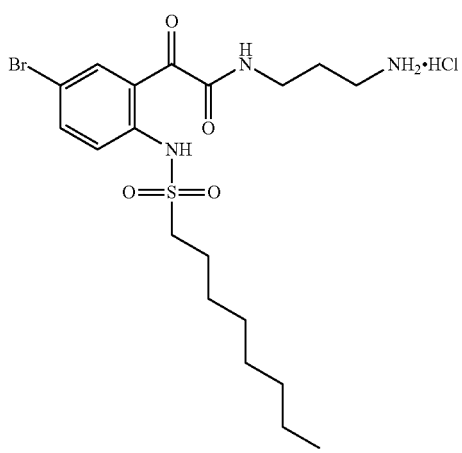

The title compound 43b was synthesised from tert-butyl (3-(2-(5-bromo-2-(octylsulfonamido)phenyl)-2-oxoacetamido)propyl)carbamate 43a (0.26 g, 0.45 mmol) following general synthetic procedure 5.1.E. The product 43b was obtained as a yellow sticky solid (0.19 g, 83%); $^1$H NMR (400 MHz, DMSO): δ 10.08 (bs, 1H, NH), 8.99 (t, J=5.8 Hz, 1H, NH), 8.12 (bs, 1H, NH), 7.96 (bs, 2H, NH), 7.90-7.83 (m, 2H, ArH), 7.46 (d, J=8.7 Hz, 1H, ArH), 3.32-3.26 (m, 2H, CH$_2$), 3.20-3.15 (m, 2H, CH$_2$), 2.91-2.80 (m, 2H, CH$_2$), 1.87-1.78 (m, 2H, CH$_2$), 1.68-1.59 (m, 2H, CH$_2$), 1.36-1.16 (m, 10H, CH$_2$), 0.84 (t, J=6.8 Hz, 3H, CH$_3$); $^{13}$C NMR (100 MHz, CDCl$_3$): δ 190.3 (CO), 162.9 (CO), 137.6 (ArC), 137.0 (ArCH), 134.2 (ArCH), 127.7 (ArC), 124.3 (ArCH), 116.2 (ArC), 51.4 (CH$_2$), 36.6 (CH$_2$), 35.9 (CH$_2$), 31.1 (CH$_2$), 28.3 (CH$_2$), 28.3 (CH$_2$), 27.3 (CH$_2$), 26.8 (CH$_2$), 22.8 (CH$_2$), 22.0 (CH$_2$), 13.9 (CH$_3$); IR (ATR): ν$_{max}$ 3329, 3252, 2920, 2047, 1640, 1523, 1475, 1385, 1334, 1256, 1195, 1141, 1019, 916, 818, 762, 715 cm$^{-1}$; UV-Vis (H$_2$O): λ$_{max}$ 231 nm (ε 19,000 cm$^{-1}$M$^{-1}$), 368 (790); HRMS (+ESI): Found m/z 476.1215 [M+H]$^+$, C$_{19}$H$_{31}$BrN$_3$O$_4$S required 476.1213.

tert-Butyl(3-(2-(5-bromo-2-(octylsulfonamido)phenyl)-2-oxoacetamido)propyl) carbamate (43a)

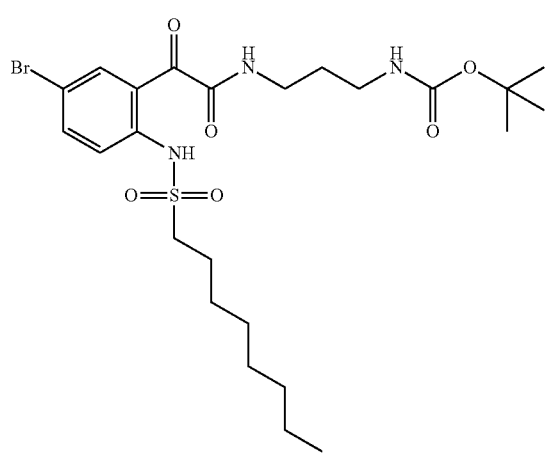

The title compound 43a was synthesised from 5-bromo-1-(octylsulfonyl)indoline-2,3-dione 14a (0.21 g, 0.51 mmol) and tert-butyl (3-aminopropyl)carbamate (92 mg, 0.51 mmol) following general synthetic procedure 5.1.C. Reaction stirred for 21 h. The product 43a was obtained as a yellow oil (0.29 g, 98%); $^1$H NMR (400 MHz, CDCl$_3$): δ 10.39 (bs, 1H, NH), 8.70-8.63 (m, 1H, ArH), 7.76 (bs, 1H, NH), 7.72-7.66 (m, 2H, ArH), 4.80 (bs, 1H, NH), 3.46 (q, J=6.4 Hz, 2H, CH$_2$), 3.24 (q, J=5.8 Hz, 2H, CH$_2$), 3.16-3.11 (m, 2H, CH$_2$), 1.83-1.70 (m, 4H, CH$_2$), 1.45 (s, 9H, CH$_3$), 1.40-1.19 (m, 10H, CH$_2$), 0.86 (t, J=6.7 Hz, 3H, CH$_3$); $^{13}$C NMR (100 MHz, CDCl$_3$): δ 190.4 (CO), 162.2 (CO), 157.0 (CO), 141.0 (ArC), 139.3 (ArCH), 137.5 (ArCH), 120.4 (ArC), 119.8 (ArCH), 115.2 (ArC), 80.0 (C), 52.9 (CH$_2$), 37.2 (CH$_2$), 36.4 (CH$_2$), 31.8 (CH$_2$), 30.2 (CH$_2$), 29.0 (CH$_2$), 29.0 (CH$_2$), 28.5 (CH$_3$), 28.2 (CH$_2$), 23.5 (CH$_2$), 22.7 (CH$_2$), 14.2 (CH$_3$); IR (ATR): ν$_{max}$ 3226, 3176, 2922, 2852, 2318, 2117, 1684, 1631, 1519, 1479, 1390, 1334, 1247, 1136, 1010, 914, 835, 723 cm$^{-1}$; UV-Vis (MeOH): λ$_{max}$ 231 nm (ε 19,000 cm$^{-1}$M$^{-1}$), 347 (950); HRMS (+ESI): Found m/z 598.1559 [M+Na]$^+$, C$_{24}$H$_{38}$BrN$_3$O$_6$SNa required 598.1557.

Synthesis of Compounds 44a, 45a, 46a, 46b and 46c

5-Phenylindoline-2,3-dione (44a)

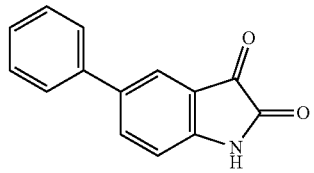

To a solution of 5-bromoisatin (1.13 g, 4.98 mmol) and phenylboronic acid (0.67 g, 5.50 mmol) in degassed 1:1 toluene/ethanol solution (30 mL) was added 2 M potassium carbonate solution (5.0 mL). The solution mixture was stirred and degassed for 30 min, followed by the addition of tetrakis(triphenylphosphine)palladium(0) (68 mg, 0.059 mmol). The reaction mixture was then heated at 90° C. under nitrogen atmosphere for 18 hours. After completion of reaction, water (50 mL) was added to the reaction mixture. 2 M HCl was then added to acidify the reaction mixture until pH 1. The organic layer was extracted into dichloromethane (3×30 mL), washed with brine, dried over anhydrous sodium sulfate and concentrated in vacuo to afford the product 44a as a red solid (0.79 g, 71%); $^1$H NMR (400 MHz, DMSO-d$_6$): δ 11.13 (s, 1H, NH), 7.90 (d, J=8.3 Hz, 1H, ArH), 7.75 (s, 1H, ArH), 7.64 (d, J=7.8 Hz, 2H, ArH), 7.45 (t, J=7.8 Hz, 2H, ArH), 7.35 (t, J=7.4 Hz, 1H, ArH), 7.00 (d, J=8.1 Hz, 1H, ArH); $^{13}$C NMR (100 MHz, DMSO-d$_6$): δ 184.4 (CO), 159.6 (CO), 150.0 (ArC), 138.7 (ArC), 136.5 (ArCH), 134.9 (ArC), 129.0 (ArCH), 127.5 (ArCH), 126.2 (ArCH), 122.5 (ArCH), 118.4 (ArC), 112.7 (ArCH).

1-(Octylsulfonyl)-5-phenylindoline-2,3-dione (45a)

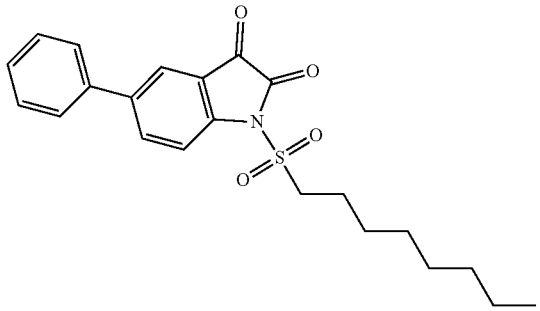

The title compound 45a was synthesised from 5-phenylindoline-2,3-dione 44a (0.75 g, 3.19 mmol), triethylamine (0.50 mL, 3.59 mmol) and octane-1-sulfonyl chloride (0.65 mL, 3.32 mmol) following general synthetic procedure 5.1.A. Reaction was stirred for 3 h. The product 45a was obtained as a yellow solid (0.29 g, 23%); $^1$H NMR (400 MHz, DMSO-$d_6$): δ 8.08 (dd, J=8.5, 2.1 Hz, 1H, ArH), 7.98 (d, J=2.0 Hz, 1H, ArH), 7.80 (d, J=8.5 Hz, 1H, ArH), 7.75-7.71 (m, 2H, ArH), 7.52-7.46 (m, 2H, ArH), 7.44-7.38 (m, 1H, ArH), 3.67-3.59 (m, 2H, CH$_2$), 1.86-1.75 (m, 2H, CH$_2$), 1.43-1.16 (m, 10H, CH$_2$), 0.83 (t, J=6.6 Hz, 3H, CH$_3$); $^{13}$C NMR (100 MHz, DMSO-$d_6$): δ 178.7 (CO), 156.6 (CO), 146.1 (ArC), 138.0 (ArC), 137.0 (ArC), 135.9 (ArCH), 129.2 (ArCH), 129.1 (ArCH), 128.1 (ArCH), 126.5 (ArCH), 126.5 (ArCH), 122.4 (ArCH), 120.1 (ArC), 114.6 (ArCH), 53.7 (CH$_2$), 31.1 (CH$_2$), 28.4 (CH$_2$), 28.3 (CH$_2$), 27.3 (CH$_2$), 22.2 (CH$_2$), 22.0 (CH$_2$), 13.9 (CH$_3$).

N-(3-(Dimethylamino)propyl)-2-(4-(octylsulfonamido)-[1,1'-biphenyl]-3-yl)-2-oxoacetamide (46a)

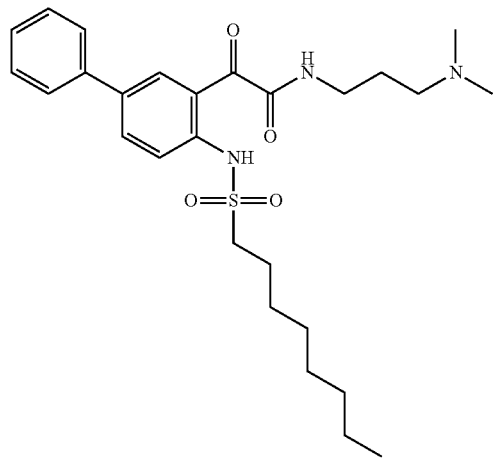

The title compound 46a was synthesised from 1-(octylsulfonyl)-5-phenylindoline-2,3-dione 45a (0.11 g, 0.28 mmol) and N,N-dimethylpropane-1,3-diamine (35 μL, 0.28 mmol) following general synthetic procedure 5.1.C. Reaction was stirred for 6 h. The product 46a was obtained as a yellow oil (0.13 g, 96%); $^1$H NMR (400 MHz, CDCl$_3$): δ 8.78 (bs, 1H, NH), 8.72 (d, J=1.9 Hz, 1H, ArH), 7.87-7.80 (m, 2H, ArH), 7.60-7.55 (m, 2H, ArH), 7.47-7.41 (m, 2H, ArH), 7.40-7.33 (m, 1H, ArH), 3.53 (t, J=6.1 Hz, 2H, CH$_2$), 3.21-3.15 (m, 2H, CH$_2$), 2.55 (t, J=6.2 Hz, 2H, CH$_2$), 2.33 (s, 6H, CH$_3$), 1.86-1.76 (m, 4H, CH$_2$), 1.43-1.17 (m, 10H, CH$_2$), 0.85 (t, J=7.1 Hz, 3H, CH$_3$); $^{13}$C NMR (100 MHz, CDCl$_3$): δ 192.0 (CO), 162.8 (CO), 140.9 (ArC), 139.1 (ArC), 135.8 (ArC), 134.9 (ArCH), 133.6 (ArCH), 129.1 (ArCH), 127.9 (ArCH), 127.0 (ArCH), 119.7 (ArC), 118.6 (ArCH), 58.6 (CH$_2$), 52.7 (CH$_2$), 45.2 (CH$_3$), 39.8 (CH$_2$), 31.8 (CH$_2$), 29.1 (CH$_2$), 29.0 (CH$_2$), 28.2 (CH$_2$), 25.3 (CH$_2$), 23.5 (CH$_2$), 22.7 (CH$_2$), 14.2 (CH$_3$).

N,N-Dimethyl-3-(2-(4-(octylsulfonamido)-[1,1'-biphenyl]-3-yl)-2-oxoacetamido)propan-1-aminium chloride (46b)

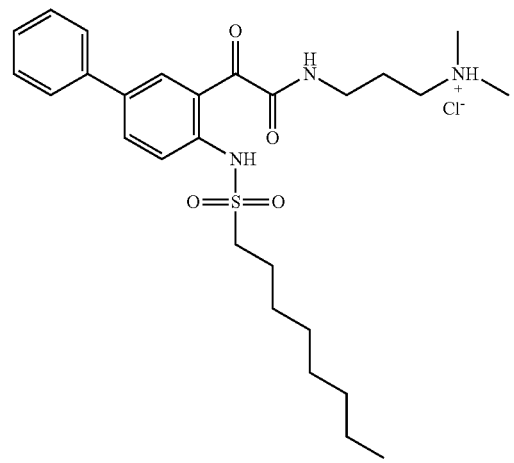

The title compound 46b was synthesised from N-(3-(Dimethylamino)propyl)-2-(4-(octylsulfonamido)-[1,1'-biphenyl]-3-yl)-2-oxoacetamide 46a (33 mg, 0.066 mmol) and 4 M HCl/dioxane (0.10 mL, 0.40 mmol) in diethyl ether (3 mL) following general synthetic procedure 5.1.D. Reaction was stirred for 30 min. The product 46b was obtained as a yellow sticky solid (33 mg, 93%); $^1$H NMR (600 MHz, DMSO-$d_6$): δ 10.25 (bs, 2H, NH), 9.03 (t, J=5.7 Hz, 1H, NH), 8.02-7.98 (m, 2H, ArH), 7.68-7.60 (m, 3H, ArH), 7.52-7.48 (m, 2H, ArH), 7.40 (t, J=7.4 Hz, 1H, ArH), 3.32 (t, J=6.1 Hz, 2H, CH$_2$), 3.25-3.19 (m, 2H, CH$_2$), 3.12-3.07 (m, 2H, CH$_2$), 2.73 (s, 6H, CH$_3$), 1.98-1.90 (m, 2H, CH$_2$), 1.71-1.63 (m, 2H, CH$_2$), 1.37-1.16 (m, 10H, CH$_2$), 0.82 (t, J=7.2 Hz, 3H, CH$_3$); $^{13}$C NMR (150 MHz, DMSO-$d_6$): δ 192.1 (CO), 163.8 (CO), 138.3 (ArC), 137.9 (ArC), 135.9 (ArC), 132.9 (ArCH), 130.3 (ArCH), 129.2 (ArCH), 127.9 (ArCH), 126.5 (ArCH), 125.8 (ArC), 122.3 (ArCH), 54.4 (CH$_2$), 51.3 (CH$_2$), 42.0 (CH$_3$), 36.0 (CH$_2$), 31.1 (CH$_2$), 28.4 (CH$_2$), 28.3 (CH$_2$), 27.3 (CH$_2$), 23.9 (CH$_2$), 22.9 (CH$_2$), 22.0 (CH$_2$), 13.9 (CH$_3$).

N,N,N-Trimethyl-3-(2-(4-(octylsulfonamido)-[1,1'-biphenyl]-3-yl)-2-oxoacetamido)propan-1-aminium iodide (46c)

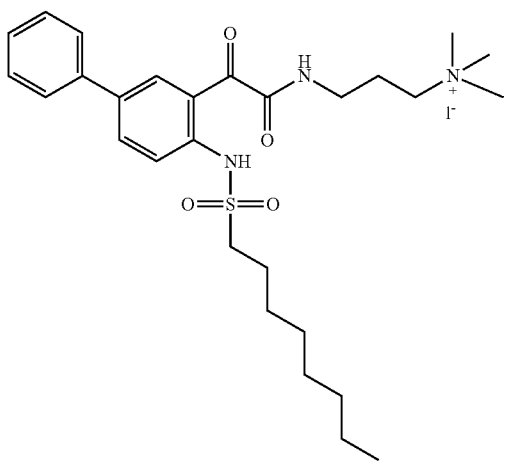

The title compound 46c was synthesised from N-(3-(Dimethylamino)propyl)-2-(4-(octylsulfonamido)-[1,1'-biphenyl]-3-yl)-2-oxoacetamide 46a (30 mg, 0.060 mmol) and iodomethane (10 µL, 0.16 mmol) in tetrahydrofuran (3 mL) following general synthetic procedure 5.1.D. Reaction was stirred for 48 h. The product 46c was obtained as a yellow sticky solid (31 mg, 80%); $^1$H NMR (600 MHz, DMSO-$d_6$): 10.10 (bs, 1H, NH), 8.98 (t, J=5.8 Hz, 1H, NH), 8.02-7.98 (m, 2H, ArH), 7.68-7.64 (m, 2H, ArH), 7.59-7.55 (m, 1H, ArH), 7.52-7.47 (m, 2H, ArH), 7.43-7.39 (m, 1H, ArH), 3.39-3.30 (m, 4H, $CH_2$), 3.21-3.15 (m, 2H, $CH_2$), 3.06 (s, 9H, $CH_3$), 2.02-1.95 (m, 2H, $CH_2$), 1.72-1.63 (m, 2H, $CH_2$), 1.40-1.14 (m, 10H, $CH_2$), 0.83 (t, J=7.2 Hz, 3H, $CH_3$); $^{13}$C NMR (150 MHz, DMSO-$d_6$): δ 191.8 (CO), 163.7 (CO), 138.3 (ArC), 132.7 (ArCH), 130.1 (ArCH), 129.2 (ArC), 129.2 (ArCH), 128.0 (ArCH), 126.8 (ArC), 126.5 (ArCH), 126.2 (ArC), 122.9 (ArCH), 63.5 ($CH_2$), 52.3 ($CH_3$), 51.2 ($CH_2$), 35.9 ($CH_2$), 31.1 ($CH_2$), 28.4 ($CH_2$), 28.3 ($CH_2$), 27.3 ($CH_2$), 22.9 ($CH_2$), 22.6 ($CH_2$), 22.0 ($CH_2$), 13.9 ($CH_3$).

Minimal Inhibitory Concentration (MIC) Assay

Compounds 24a, 38b, 42d and 43d were assessed by determining their minimum inhibitory concentration (MIC) according to a previously published protocol (see Wiegand, I.; Hilpert, K.; Hancock, R. E. W. Nat. Protocols 2008, 3 (2), 163-175). A single colony of bacteria was cultured overnight in TSB at 37° C. The resulting bacterial culture was collected by centrifugation and re-suspended in TSB twice. The optical density (OD) of the resulting culture was adjusted to $OD_{600}$=0.1 in TSB (equivalent to $10^8$ colony forming unit (CFU)/mL bacteria), and was further diluted to $10^5$ CFU/mL in TSB. 100 µL of the bacterial solution was then added to wells of a 96-well plate containing 100 µL serially diluted compound, with final concentration ranging from 8-250 µM. The plates were then incubated at 37° C. for 24 h and the data was recorded by measuring the OD value at 600 nm using a Wallac Victor (Perkin-Elmer) microplate reader. The MIC value of each compound was determined as the lowest concentration that completely inhibited the growth of bacteria. Each experiment was performed in triplicate and was repeated in two independent experiments. The results of the MIC assay are given below in Table 2.

TABLE 2

Minimum inhibitory concentration of compounds against S. aureus (SA38).

| Compound | MIC (µM) |
| --- | --- |
| 24a | 47 |
| 38b | 63 |
| 42d | 47 |
| 43d | 12 |
| MSI-78* | 13 |

(*Literature value (see Ge, Y.; MacDonald, D. L.; Holroyd, K. J.; Thornsberry, C.; Wexler, H.; Zasloff, M. Antimicrob. Agents Chemother. 1999, 43 (4), 782-788))

Membrane Conduction

Tethered bilayer lipid membranes (tBLMs) associated with alternating current electrical impedance spectroscopy techniques were employed to determine whether the compounds (24a, 38b, 42d, 43d) are lytic to cell membranes. Sparsely tethered tBLMs containing 30% palmitoyl-oleoyl-phosphati-dylglycerol (POPG) were created using the solvent-exchange technique described by Cranfield et al. in 2015 (see Cranfield, C. G.; Bettler, T.; Cornell, B. Langmuir 2015, 31 (1), 292-298). The tBLM conduction responses of compounds (24a, 38b, 42d, 43d) were compared to that of LL-37, a cathelicidin AMP that is known to permeabilise membranes.

Figure 8:
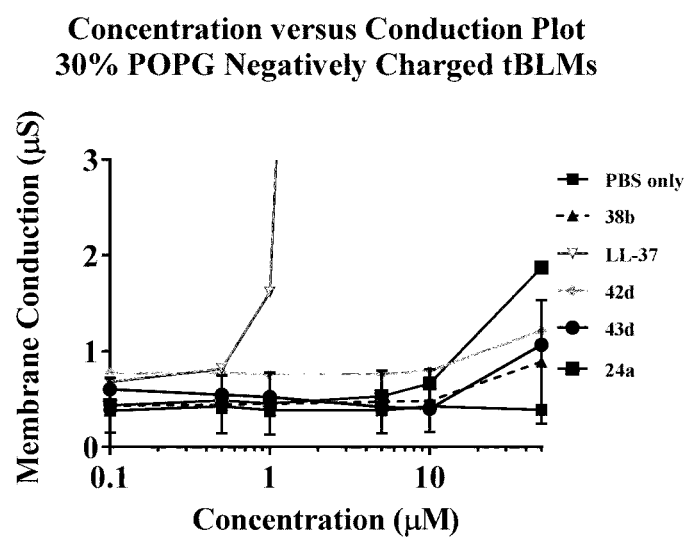
FIG. 8 is a graph of membrane conduction (pS) versus concentration of compounds 24a, 38b, 42d, 43d and LL-37 in tethered bilayer lipid membranes (tBLMs).

In a preliminary study, all tested compounds (24a, 38b, 42d, 43d) showed conduction responses against a negatively charged lipid at 50 µM concentration (FIG. 8), which suggested that compounds (24a, 38b, 42d, 43d) were able to affect membrane packing and thus membrane permeability. Although these compounds have a similar MIC as that of the antimicrobial peptide LL-37 (MIC=49 µM), they showed much less activity than LL-37 in the assay. It was postulated that the change in lipid morphology could have increased the pore surface area of lipid and thereby increase overall membrane conduction (see Cranfield, C. G.; Berry, T.; Holt, S. A.; Hossain, K. R.; Le Brun, A. P.; Came, S.; Al Khamici, H.; Coster, H.; Valenzuela, S. M.; Cornell, B. Langmuir 2016, 32 (41), 10725-10734). Regardless of the mechanism, the increase in membrane conduction demonstrates the potential of these compounds to act as antimicrobial pore forming agents. Further investigation using a dye release study could further confirm such a mechanism.

Cytotoxicity Assay

The in vitro toxicity of the compounds (24a, 38b, 42d, 43d) was determined against MRC-5 normal human lung fibroblasts using the Alamar blue assay (see O'Brien, J.; Wilson, I.; Orton, T.; Pognan, F. Eur. J. Biochem. 2000, 267 (17), 5421-5426). A dose-response curve for each compound was generated to determine the $IC_{50}$ values (concentration of compound which killed half of the cells) and the $IC_{50}$ values were then used to determine the therapeutic window ($IC_{50}$ value divided by MIC value) and specificity of the compounds (Table 3).

TABLE 3

Minimum inhibitory concentration of compounds against S. aureus (SA38) and their toxicity against MRC-5 normal human lung fibroblasts.

| Compound | $IC_{50}$ (µM) | MIC (µM) | Therapeutic window |
| --- | --- | --- | --- |
| 24a | 37.4 | 47 | 0.80 |
| 38b | 75.5 | 63 | 1.20 |

TABLE 3-continued

Minimum inhibitory concentration of compounds against
S. aureus (SA38) and their toxicity against MRC-5 normal
human lung fibroblasts.

| Compound | IC$_{50}$ (µM) | MIC (µM) | Therapeutic window |
|---|---|---|---|
| 42d | 373 | 47 | 7.94 |
| 43d | 178 | 12 | 14.83 |

As expected, the glyoxamide compound 24a showed a high level of toxicity to human cells. This can be explained by the lack of cationic charge at the terminal group of compound 24a. Without a cationic charge at the terminal group, compound 24a has higher hydrophobicity and can more easily bind to the uncharged human cell membrane. Moreover, compound 24a showed a therapeutic window of less than 1, meaning that it cannot be used as an antibacterial agent.

Comparison between the two guanidine hydrochloride salts 42d-43d showed that compound 43d with a more hydrophobic bromine substituent at the 5-position of the phenyl ring was more toxic than compound 42d which has a hydrogen atom at that position (IC$_{50}$=178 µM vs. 373 µM). This suggested that there might be a positive correlation between the hydrophobicity and the toxicity of the compounds towards human cells.

Although the guanidine hydrochloride salt 43d has a relatively low IC$_{50}$ value compared to compound 42d, it also had a significantly lower MIC value which resulted in a higher therapeutic window value. Overall, these data suggest that guanidine hydrochloride salts of glyoxamides are useful scaffolds for the further development of antimicrobial drugs to treat human bacterial infection.

Example 3

Various compounds of Formula (ID and Formula (Ik) were prepared as described in Schemes 4 and 5 described below.

Scheme 4: General scheme for the synthesis of isatoic anhydride derived peptidomimetics

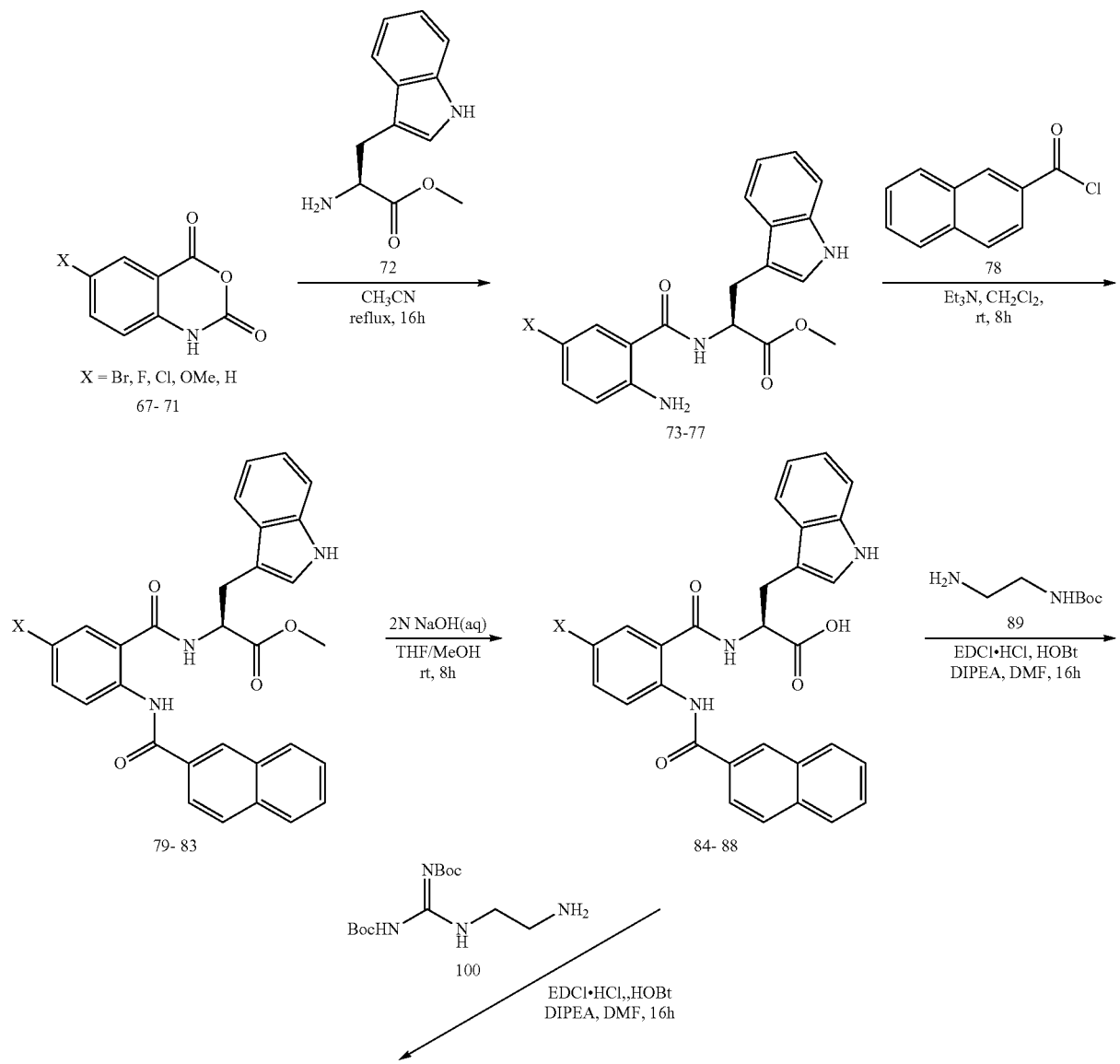

-continued
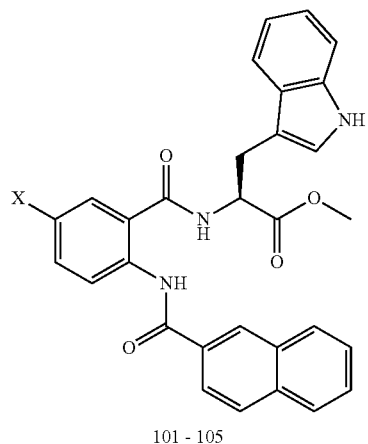
101 - 105
TFA, CH₂Cl₂
8h
4N HCl in dioxane ↓
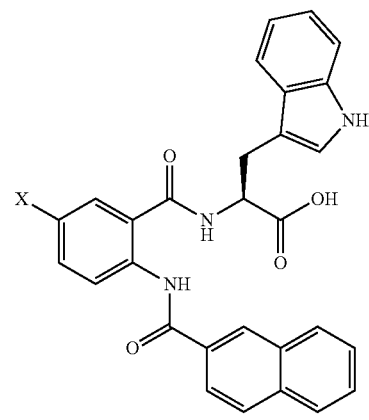
90 - 94
4N HCl in dioxane
CH₂Cl₂, 4h ↓
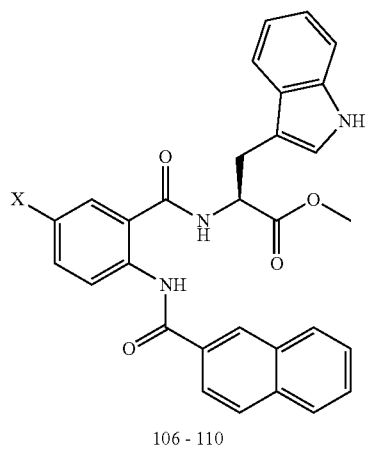
106 - 110
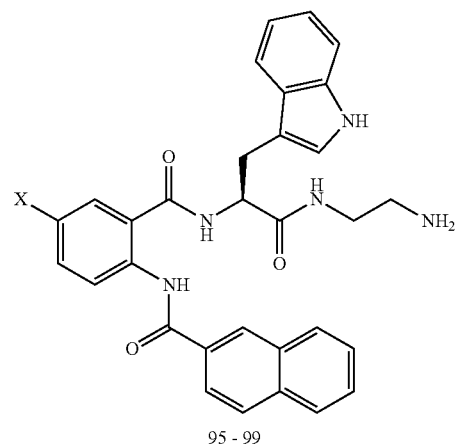
95 - 99
Scheme 5: General scheme for the synthesis of isatoic anhydride derived peptidomimetics
84-88
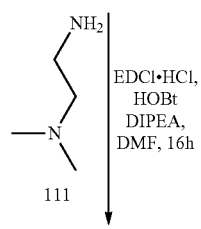
111
EDCl·HCl,
HOBt
DIPEA,
DMF, 16h ↓

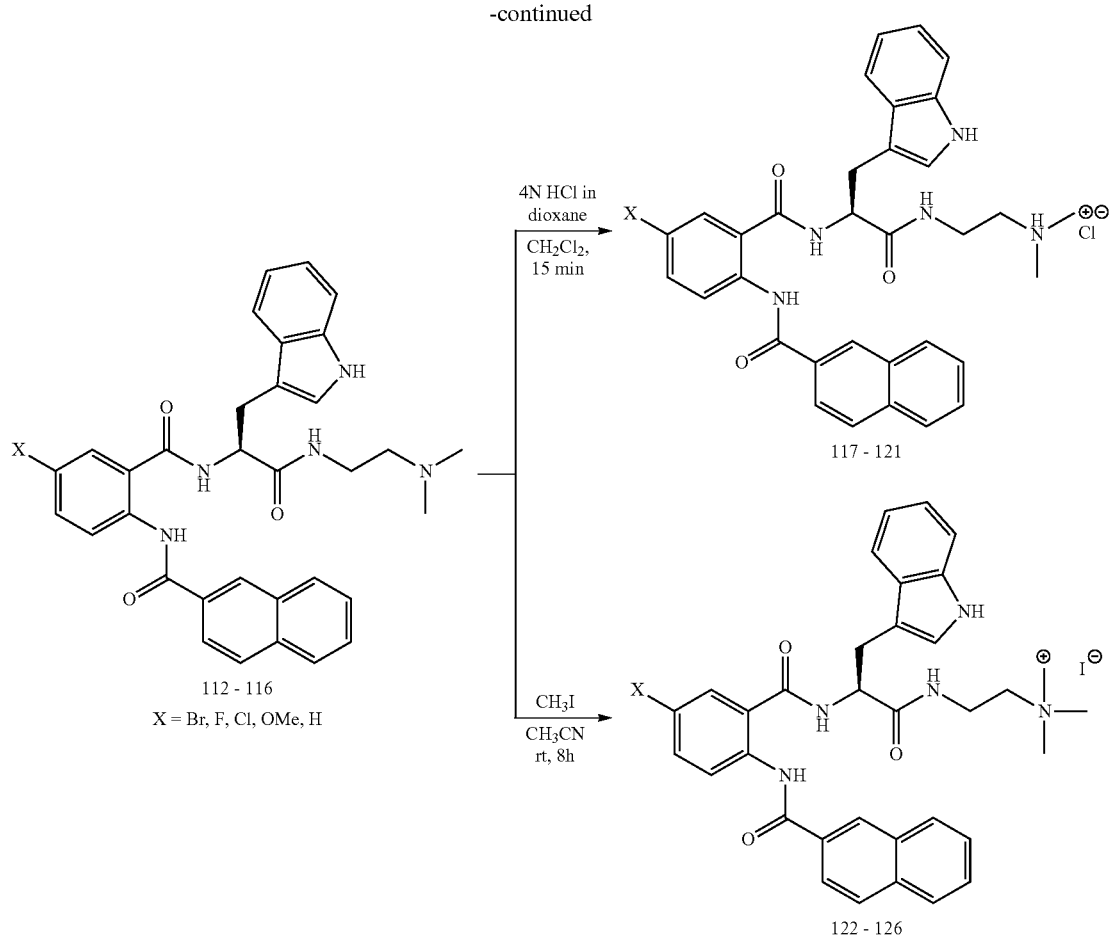

The synthesis of scaffold (84-88) was achieved via ring-opening reaction of isatoic anhydrides (67-71) with equimolar amount of methyl-L-tryptophanate in acetonitrile over 16 h under reflux condition, gave anthranilate compounds (73-77) in good to excellent yields (63-88%) (Scheme 4). The corresponding amines (73-77) were reacted with 1.2 equivalents of 2-naphthoyl chloride 78 in dichloromethane at room temperature using 3.0 equivalents of triethylamine as a base yielded (79-83) in quantitative amount. Hydrolysis of methyl ester with 2 N NaOH in THF and MeOH at room temperature for 2 h gave the acids (84-88) in good yields (82-95%).

These acid scaffolds (84-88) were then coupled with tert-butyl (2-aminoethyl)carbamate (89), 1-(2-aminoethyl) boc guanidine (100), and N, N-dimethyl-1,2-ethanediamine (111) using EDC.HCl/HOBt and (i-Pr)$_2$NEt in DMF at rt for 8 h, afforded amides (90-94), (101-105) and (106-110) in yields of 50-78%, respectively. Deprotection of Boc group of (90-94) with 4 M HCl/dioxane in DCM gave amine hydrochlorides (95-99) in quantitative yields (90%-95%). Compounds (101-105) were deprotected using TFA in DCM at 0° C. for 4 h and subsequent salt exchange with 4 M HCl/dioxane in DCM afforded compounds (106-110) in moderate yields ranging from 50-70% respectively.

Finally, the aminium chloride (117-121) salts were prepared from (112-116) by treating with 4 M HCl/dioxane in DCM for 15 min in good yields and the aminium iodide (122-126) salts were derived quantitatively by treating (112-116) with equimolar amount of methyl iodide in acetonitrile at room temperature for 8 h (Scheme 5).

General Procedure N for Synthesis of Compounds 90-94, 101-105, and 112-116

To a stirred solution of an acid (84-88) (1 equiv), amine 89 or 100 or 111 (1.0 equiv), HOBt (1.0 equiv), DIEA (2.5 equiv) in DMF (3-5 mL), EDCI (1.2 equiv) was added portionwise. The reaction was stirred overnight before the solvent was removed under reduced pressure and the resulting residue was subjected to flash chromatography (2-5% MeOH/CH$_2$Cl$_2$ as the eluent) to afford the desired compounds 90-94 or 101-105 or 112-116 respectively.

General Procedure O for Synthesis of Compounds 95-99

To a solution of 8a-8e (1 mmol) in dichloromethane was added HCl in dioxane (4 M solution) (5.0 equiv) at 0° C. The reaction mixture was warmed to room temperature and stirred for 16 h. After completion of the reaction, solvent was removed under reduced pressure and treated with diethyl ether and compound was dried under high vacuum to yield the product.

General Procedure P for Synthesis of Compounds 106-110

To a solution of 101-105 (1 mmol) in dichloromethane (1 mL) was added TFA (1 mL). The reaction mixture was warmed to room temperature and stirred for 8 h. After completion of the reaction, excess solvent was removed under reduced pressure and treated with excess HCl in dioxane (4M solution) to exchange the TFA anion with HCl. After that reaction mixture was again concentrated to get sticky solid. This was dissolved in minimum amount of MeOH (10 drops) and diethyl ether (5-10 mL) was added to get precipitate out the product (50%-70%). (see Wales, S. M.; Hammer, K. A.; King, A. M.; Tague, A. J.; Lyras, D.; Riley, T. V.; Keller, P. A.; Pyne, S. G. *Org. Biomol. Chem.* 2015, 13, 5743.)

General Procedure Q for Synthesis of Compounds 117-121

To a solution of 112-116 (1 mmol) in DCM was added 4 M HCl/dioxane (1.0 mL). The reaction mixture was stirred at room temperature for 15 min. After completion of the reaction, solvent was removed under reduced pressure and treated with diethyl ether and compound was dried under high vacuum to yield the product.

General Procedure R for Synthesis of Compounds 122-126

To a solution of 112-116 (1 mmol) in $CH_3CN$ was added $CH_3I$ (1.0 mmol). The reaction mixture was stirred at room temperature for 8 h. After completion of the reaction, solvent was removed under reduced pressure and treated with diethyl ether and compound was dried under high vacuum to yield the product.

(S)—N-(2-((1-((2-Aminoethyl)amino)-3-(1H-indol-3-yl)-1-oxopropan-2-yl)carbamoyl)-4-bromophenyl)-2-naphthamide (95)

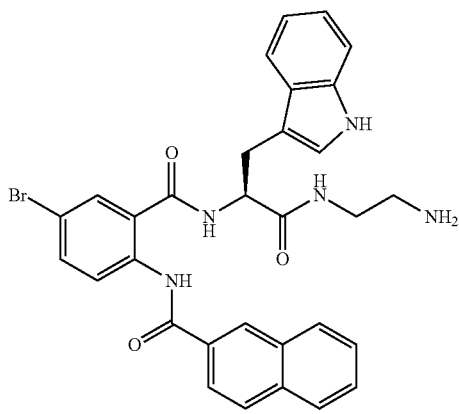

95

The title compound 95 was prepared from compound 90 (70 mg, 0.1 mmol), treating with HCl in dioxane (4 M solution) according to the general procedure O. The product was obtained as off-white solid (39 mg, 67%); $^1$H NMR 400 MHz, DMSO-$d_6$: δ 10.81 (s, 1H), 9.18 (br s, 1H), 8.53 (dd, J=4.0, 10.0 Hz, 1H), 8.44 (br s, 1H), 8.21 (t, J=4.00 Hz, 1H), 8.07-8.01 (m, 5H), 7.85 (d, J=8.00 Hz, 1H), 7.76 (dd, J=4.0, 12.0 Hz, 1H), 7.71-7.61 (m, 4H), 7.26-7.21 (m, 2H), 7.03-6.93 (m, 2H), 4.74 (q, J=4.0 Hz, 1H), 3.18-3.10 (m, 6H); $^{13}$C NMR (DMSO-$d_6$, 100 MHz): δ 171.5, 167.7, 165.1, 136.5, 135.2, 134.9, 132.6, 132.0, 131.6, 129.6, 129.1, 128.6, 128.4, 128.1, 127.7, 127.5, 124.0, 123.6, 123.1, 122.9, 121.3, 118.9, 118.7, 115.1, 111.8, 110.9, 79.6, 55.2, 39.2, 27.8; HRMS (ESI): m/z calcd for $C_{31}H_{28}BrN_5O_3$ [M+H]$^+$ 598.1376, found 598.1412.

(S)—N-(4-Bromo-2-((1-((2-guanidinoethyl)amino)-3-(1H-indol-3-yl)-1-oxopropan-2-yl)carbamoyl)phenyl)-2-naphthamide (106)

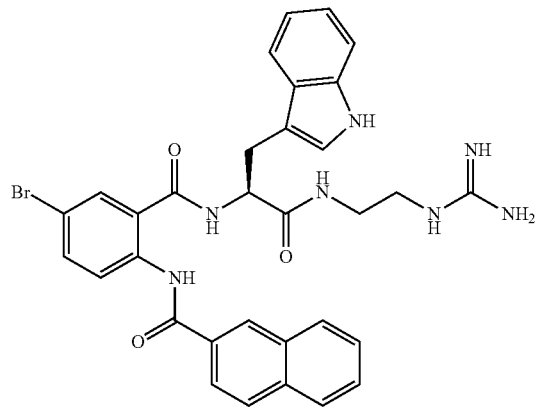

106

The title compound 106 was prepared from compound 101 (100 mg, 0.11 mmol), TFA and HCl in dioxane (4 M solution) according to the general procedure P. The product was obtained as off-white solid (35 mg, 50%); $^1$HNMR (DMSO-$d_6$, 400 MHz): δ 12.15 (s, 1H), 10.81 (br s, 1H), 9.18 (d, J=8.0 Hz, 1H), 8.54 (d, J=8.0 Hz, 1H), 8.38-8.34 (m, 2H), 8.06-8.01 (m, 4H), 7.83 (dd, J=4.0, 8.0 Hz, 1H), 7.78 (dd, J=4.0, 8.0 Hz, 1H), 7.48-7.47 (m, 1H), 7.26-7.20 (m, 5H), 7.02-6.96 (m, 3H), 4.79-4.74 (m, 1H), 3.31-3.13 (m, 6H); $^{13}$C NMR (DMSO-$d_6$, 100 MHz): δ 172.2, 167.8, 165.1, 157.4, 138.8, 136.5, 135.3, 134.9, 132.6, 132.1, 129.6, 129.1, 128.7, 128.4, 128.2, 127.6, 127.5, 124.1, 123.6, 123.5, 123.0, 122.9, 121.4, 118.8, 118.7, 115.1, 111.8, 110.8, 55.0, 38.5, 27.7, 27.6; HRMS (ESI): m/z calcd for $C_{32}H_{30}BrN_7O_3$ [M+H]$^+$ 640.1594, found 640.1647.

(S)-2-(2-(2-(2-Naphthamido)-5-bromobenzamido)-3-(1H-indol-3-yl)propanamido)-N,N-dimethylethan-1-aminium chloride (117)

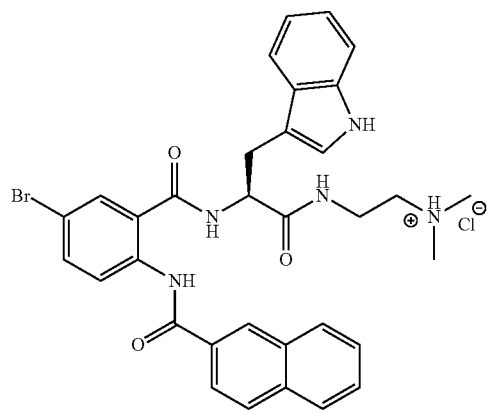

117

The title compound 117 was prepared from compound 112 (50 mg, 0.07 mmol), HCl in dioxane (4 M solution) according to the general procedure Q. The product was obtained as off-white solid (45 mg, 90%); $^1$H NMR (CDCl$_3$, 400 MHz): δ 12.20 (s, 1H), 8.78 (d, J=8.0 Hz, 1H), 8.55 (br s, 1H), 8.15 (br s, 1H), 8.07-8.01 (m, 2H), 7.95 (d, J=8.0 Hz, 1H), 7.90 (d, J=8.0 Hz, 1H), 7.78 (d, J=8.0 Hz, 1H), 7.65-7.54 (m, 4H), 7.43-7.41 (m, 1H), 7.33-7.31 (m, 1H), 7.21-7.13 (m, 3H), 6.23 (br s, 1H), 4.95-4.89 (m, 1H), 3.46 (dd, J=8.0, 14.0 Hz, 1H), 3.29-3.10 (m, 3H), 2.23-2.17 (m, 1H), 2.07-2.01 (m, 1H), 1.98 (s, 6H); $^{13}$CNMR (CDCl$_3$, 400 MHz): δ 170.5, 167.4, 165.5, 139.2, 136.2, 135.7, 135.0, 132.7, 131.8, 129.7, 129.4, 128.6, 128.4, 127.9, 127.7, 127.4, 126.7, 123.6, 123.1, 122.5, 121.5, 120.0, 118.8, 115.3, 111.3, 110.7, 57.1, 54.6, 44.6, 36.7, 29.0; HRMS (ESI): m/z calcd for C$_{33}$H$_{33}$BrClN$_5$O$_3$ [M+H]$^+$ 662.1455, found 626.1757.

(S)—N-(2-((1-((2-Aminoethyl)amino)-3-(1H-indol-3-yl)-1-oxopropan-2-yl)carbamoyl)-4-fluorophenyl)-2-naphthamide (96)

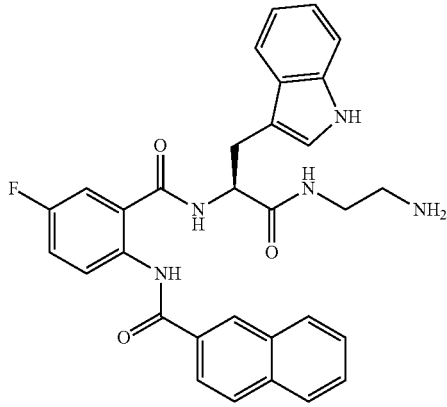

96

The title compound 96 was prepared from compound 91 (60 mg, 0.09 mmol), treating with HCl in dioxane (4M solution) according to the general procedure O. The product was obtained as off-white solid (38 mg, 79%); $^1$HNMR (DMSO-d$_6$, 300 MHz): δ 12.04 (s, 1H), 10.83 (br s, 1H), 9.18 (d, J=12.0 Hz, 1H), 8.58-8.37 (m, 3H), 8.09-8.02 (m, 7H), 7.86 (d, J=12.0 Hz, 1H), 7.74-7.62 (m, 4H), 7.47-7.44 (m, 1H), 7.27-7.23 (m, 1H), 7.03-6.93 (m, 3H), 4.79 (q, J=−12.00 Hz, 1H), 3.24-2.85 (m, 6H); $^{13}$CNMR (DMSO-d$_6$, 75 MHz): δ 171.9, 169.5, 167.8, 165.0, 136.7, 136.5, 134.8, 132.6, 132.1, 131.6, 129.6, 129.1, 128.3, 128.2, 127.7, 127.5, 124.1, 123.6, 123.2, 121.3, 118.9, 118.6, 115.1, 111.8, 110.8, 66.8, 54.9, 38.8, 37.0, 27.8; HRMS (ESI): m/z calcd for C$_{31}$H$_{28}$FN$_5$O$_{63}$ [M+H]$^+$ 538.2176, found 538.2242.

(S)—N-(4-Fluoro-2-((1-((2-guanidinoethyl)amino)-3-(1H-indol-3-yl)-1-oxopropan-2-yl)carbamoyl)phenyl)-2-naphthamide (107)

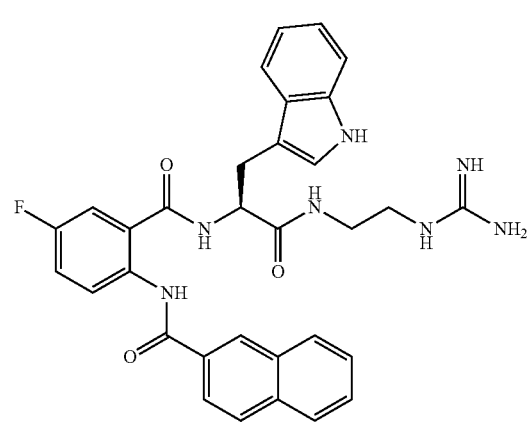

107

The title compound 107 was prepared from compound 102 (100 mg, 0.11 mmol), TFA and HCl in dioxane (4M solution) according to the general procedure P. The product was obtained as off-white solid (35 mg, 50%); $^1$H NMR (DMSO-d$_6$, 400 MHz): δ 12.05 (s, 1H), 10.79 (br s, 1H), 9.24 (d, J=8.0 Hz, 1H), 8.57 (dd, J=4.0, 10.0 Hz, 1H), 8.50-8.39 (m, 4H), 8.07-8.01 (m, 3H), 7.85 (d, J=8.00 Hz, 1H), 7.70-7.58 (m, 8H), 7.26-7.22 (m, 2H), 7.05-6.94 (m, 2H), 6.79 (br s, 1H), 4.77-4.74 (m, 1H), 3.27-3.16 (m, 6H); $^{13}$C NMR (DMSO-d$_6$, 100 MHz): δ 172.1, 167.8, 165.1, 138.4, 136.5, 134.9, 132.6, 132.4, 132.0, 129.6, 129.1, 128.8, 128.7, 128.4, 128.1, 127.6, 127.59, 127.2, 124.1, 123.6, 122.9, 122.7, 121.4, 118.8, 118.7, 111.8, 110.8, 54.9, 38.9, 37.1, 27.6; HRMS (ESI): m/z calcd for C$_{32}$H$_{30}$FN$_7$O$_6$ [M+H]$^+$ 580.2414, found 580.2461.

(S)—N-(2-((1-((2-Guanidinoethyl)amino)-3-(1H-indol-3-yl)-1-oxopropan-2-yl)carbamoyl)-4-methoxyphenyl)-2-naphthamide (109)

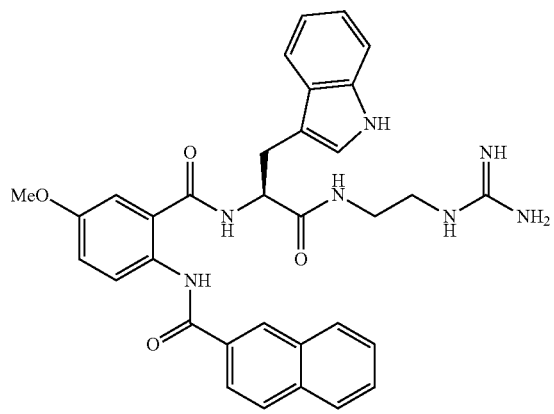

109

The title compound 109 was prepared from compound 104 (100 mg, 0.11 mmol), TFA and HCl in dioxane (4M solution) according to the general procedure P. The product was obtained as off-white solid (35 mg, 50%); $^1$H NMR (DMSO-d$_6$, 600 MHz): δ 11.87 (s, 1H), 10.83 (br s, 1H), 9.14 (d, J=4.0 Hz, 1H), 8.63-8.65 (m, 1H), 8.48-8.41 (m, 4H), 8.06-8.01 (m, 3H), 7.86 (dd, J=4.0, 6.0 Hz, 1H), 7.70-7.62 (m, 7H), 7.31-7.24 (m, 3H), 7.17-7.14 (m, 2H), 7.03-6.95 (m, 2H), 4.78-4.75 (m, 1H), 3.82 (s, 3H), 3.28-3.15 (m, 6H); $^{13}$C NMR (DMSO-d$_6$, 150 MHz): δ 172.1, 168.7, 167.5, 164.7, 157.9, 155.0, 136.5, 134.7, 132.6, 132.59, 129.5, 128.9, 128.4, 128.1, 128.13, 127.6, 127.4, 124.1, 123.7, 123.2, 122.8, 121.3, 118.8, 118.7, 118.2, 113.9, 113.8, 110.9, 55.9, 54.8, 38.5, 27.7; HRMS (ESI): m/z calcd for C$_{33}$H$_{33}$N$_7$O$_4$ [M+H]$^+$ 592.2617, found 592.2662.

Minimal Inhibitory Concentration (MIC) Assay

Compounds 95, 96, 106, 107, 109, 117 were assessed by determining their minimum inhibitory concentration (MIC) according through broth micro dilution assay using the procedure described by M. A. Wikler, Methods for dilution antimicrobial susceptibility tests for bacteria that grow aerobically: approved standard, Clinical and Laboratory Standards Institute, 2006. Briefly, bacteria were grown to mid-log phase in Muller Hinton broth (MHB) with shaking at 120 rpm and incubated at 37° C. for 18-24 hours. Following incubation, bacteria were washed three times in PBS pH 7.4 at 3500 g for 10 minutes. After washing, bacteria were diluted with fresh MHB. The turbidity of the bacterial suspensions were adjusted so that OD660 nm was 0.1, which gave 1×108 cfu/ml, and then further diluted to achieve 1-2×105 cfu/ml as a final bacterial concentration. Each compound was diluted (250-3.9 μM) through two-fold dilution. Wells in microtitre plates were loaded with 100 μl of inoculum containing 1-2×105 cfu/ml bacteria. Wells without any compound and containing only bacteria were used as a negative control (i.e. no inhibition of growth). Wells without bacteria but containing compound acted as another control. The microtitre plate was wrapped with paraffin to prevent evaporation and incubated with shaking at 120 rpm and 37° C. for 18-24 hours. After incubation, spectrophotometric reading was taken. The well without any bacterial growth and showing zero spectrophotometric reading regarded as mic of the compounds. The MIC results are shown in Table 4.

TABLE 4

Minimum inhibitory concentration of compounds against S. aureus (SA38) and E. coli (K12).
Minimum inhibitory concentration (MIC (μM))

| Compound | S. aureus | E. coli |
| --- | --- | --- |
| 95 | 3.9 | >125 |
| 106 | 3.9 | 15.6 |
| 117 | 7.8 | 125 |
| 96 | 7.8 | 15.6 |
| 107 | 1.8 | 125 |
| 109 | 7.8 | 62.5 |

It is to be understood that, if any prior art publication is referred to herein, such reference does not constitute an admission that the publication forms a part of the common general knowledge in the art, in Australia or any other country.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The invention claimed is:

1. A compound of Formula (I):

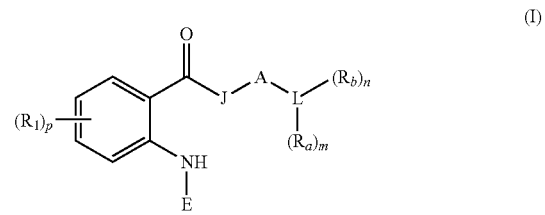

wherein:
J is

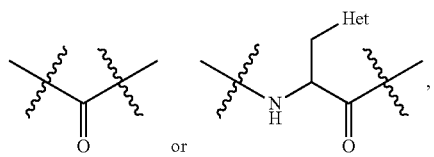

wherein Het is substituted or unsubstituted heteroaryl;
A is —NH—, —O— or —S—;
L is a saturated or unsaturated hydrocarbyl group having 1 to 12 carbon atoms, or L is —(CH$_2$—CH$_2$—O)$_r$— wherein r is 2, 3 or 4;
E is a hydrophobic group selected from —C(=O)R$_e$ or —SO$_2$R$_e$, wherein R$_e$ is C$_{6-18}$alkyl, C$_{6-18}$alkenyl, C$_{6-18}$alkynyl, aryl or heteroaryl, and wherein R$_e$ may optionally be substituted;
R$_a$ is independently selected from a substituted or unsubstituted amino group, a guanidine (—NH—C(=NH)(NH$_2$)) group, a CH$_3$-substituted guanidine (—[NCH$_3$—C(=NH)(NH$_2$)]) group, a substituted or unsubstituted ammonium group, a guanidinium (—[NH—C(=NH)(NH$_3$)]$^+$) group or a CH$_3$-substituted guanidinium (—[NCH$_3$—C(=NH)(NH$_3$)]$^+$) group;
m is 1, 2 or 3;
R$_b$, when present, is independently selected from: a substituted or unsubstituted amino group, a guanidine (—NH—C(=NH)(NH$_2$)) group, a CH$_3$-substituted guanidine (—[NCH$_3$—C(=NH)(NH$_2$)]) group, a substituted or unsubstituted ammonium group, a guanidinium (—[NH—C(=NH)(NH$_3$)]$^+$) group, a CH$_3$-substituted guanidinium (—[NCH$_3$—C(=NH)(NH$_3$)]$^+$) group, a R$_c$-substituted or unsubstituted triazolyl group, —CONHR$_c$ or —COOR$_c$, wherein R$_c$ is H, a straight or branched C$_{1-12}$alkyl group, substituted or unsubstituted aryl, or substituted or unsubstituted heteroaryl, or R$_c$ is -L-(R$_a$)$_m$, wherein L, R$_a$ and m are as defined above and wherein L may optionally be substituted with —CONHR$_d$ or —COOR$_d$, wherein R$_d$ is a straight or branched C$_{1-12}$alkyl group;
n is 0, 1, 2 or 3;
R$_1$, when present, is independently selected from Br, Cl, F, —C$_{1-3}$alkyl, —C$_{1-3}$alkoxy, substituted or unsubstituted aryl, substituted or unsubstituted heteroaryl, —SO$_3$H, —SO$_3$Na, —SO$_2$(C$_{1-3}$alkyl), —SO$_2$(OC$_{1-3}$alkyl) or —SO$_2$(N(C$_{1-3}$alkyl)(C$_{1-3}$alkyl)); and p is 0, 1, 2, 3 or 4;

or a salt thereof;

wherein when:

J is

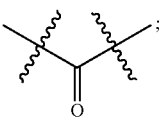 [SMILES: *C(*)=O]

A is —NH—;

L is —(CH$_2$—CH$_2$)—;

E is —C(=O)R$_e$ and R$_e$ is phenyl;

m is 1;

n is 0; and p is 0,

R$_a$ is not dimethylamino or diethylamino; and wherein when:

J is

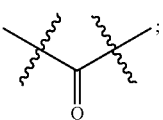 [SMILES: *C(*)=O]

A is —NH—;

L is —(CH$_2$—CH$_2$—CH$_2$)—;

E is —C(=O)R$_e$ and R$_e$ is phenyl;

m is 1;

n is 0; and p is 0,

R$_a$ is not dimethylamino.

2. A compound according to claim 1, wherein J is

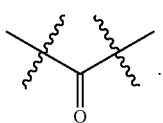 [SMILES: *C(*)=O]

3. A compound according to claim 1, wherein J is

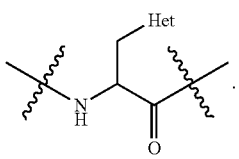

4. A compound according to claim 1, wherein J is

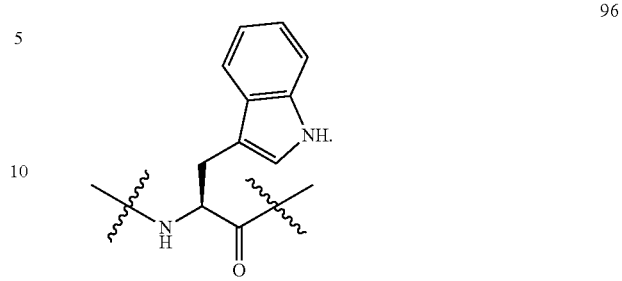

5. A compound according to claim 1, wherein A is —NH—.

6. A compound according to claim 1, wherein L is a straight chain or branched C$_{1-12}$alkyl, C$_{2-12}$alkenyl or C$_{2-12}$alkynyl.

7. A compound according to claim 6, wherein L is —CH$_2$CH$_2$—, —CH$_2$CH$_2$CH$_2$—, —CH$_2$CH$_2$CH$_2$CH$_2$—, —CH(CH$_3$)CH$_2$CH$_2$— or —CH$_2$CH(CH$_3$)CH$_2$—.

8. A compound according to claim 1, wherein E is —C(=O)R$_e$ or —SO$_2$R$_e$, wherein R$_e$ is C$_6$alkyl, C$_6$alkenyl, C$_6$alkynyl, C$_7$alkyl, C$_7$alkenyl, C$_7$alkynyl, C$_8$alkyl, C$_8$alkenyl, C$_8$alkynyl, C$_9$alkyl, C$_9$alkenyl, C$_9$alkynyl, C$_{10}$alkyl, C$_{10}$alkenyl, C$_{10}$alkynyl, C$_{11}$alkyl, C$_{11}$alkenyl, C$_{11}$alkynyl, C$_{12}$alkyl, C$_{12}$alkenyl, C$_{12}$alkynyl, C$_{13}$alkyl, C$_{13}$alkenyl, C$_{13}$alkynyl, C$_{14}$alkyl, C$_{14}$alkenyl, C$_{14}$alkynyl, C$_{15}$alkyl, C$_{15}$alkenyl, C$_{15}$alkynyl, C$_{16}$alkyl, C$_{16}$alkenyl, C$_{16}$alkynyl, C$_{17}$alkyl, C$_{17}$alkenyl, C$_{17}$alkynyl, C$_{11}$alkyl, C$_{18}$alkenyl, C$_{18}$alkynyk, phenyl, naphthyl, anthracenyl or phenanthrenyl.

9. A compound according to claim 8, wherein E is —C(=O)R$_e$ or —SO$_2$R$_e$, wherein R$_e$ is octyl, phenyl or naphthyl.

10. A compound according to claim 9, wherein E is —C(=O)R$_e$ wherein R$_e$ is naphthyl.

11. A compound according to claim 1, wherein R$_a$ is selected from —NH$_2$, —NH(CH$_3$), —N(CH$_3$)$_2$, a guanidine (—NH—C(=NH)(NH$_2$)) group, a CH$_3$-substituted guanidine (—[NCH$_3$—C(=NH)(NH$_2$)]) group, —[NH(CH$_3$)$_2$]$^+$, a guanidinium (—[NH—C(=NH)(NH$_3$)]$^+$) group, and a CH$_3$-substituted guanidinium (—[NCH$_3$—C(=NH)(NH$_3$)]$^+$) group.

12. A compound according to claim 1, wherein n is 0.

13. A compound according to claim 1, wherein R$_b$ is present and is independently selected from: —NH$_2$, —NH(CH$_3$), —N(CH$_3$)$_2$, a guanidine (—NH—C(=NH)(NH$_2$)) group, a CH$_3$-substituted guanidine —[NCH$_3$—C(=NH)(NH$_2$)) group, —NH$_3^+$, [—NH$_2$(CH$_3$)]$^+$, [—NH(CH$_3$)$_2$]$^+$, [—N(CH$_3$)$_3$]$^+$, a guanidinium (—[NH—C(=NH)(NH$_3$)]$^+$) group, a CH$_3$-substituted guanidinium (—[NCH$_3$—C(=NH)(NH$_3$)]$^+$) group, triazolyl

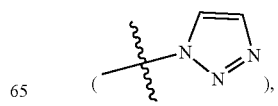

$R_c$-substituted triazolyl

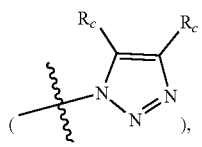

—CONHR$_c$ or —COOR$_c$; wherein each R$_c$ is independently selected from H, C$_1$alkyl, C$_2$alkyl, C$_3$alkyl, C$_4$alkyl, C$_5$alkyl, C$_6$alkyl, C$_7$alkyl, C$_8$alkyl, C$_9$alkyl, C$_{10}$alkyl, C$_{11}$alkyl, C$_{12}$alkyl, substituted or unsubstituted aryl, or substituted or unsubstituted heteroaryl.

14. A compound according to claim 1, wherein p is 0.

15. A compound according to claim 1, wherein R$_1$ is present and is independently selected from Br, Cl, F, —CH$_3$, —CH$_2$CH$_3$, —OCH$_3$, —OCH$_2$CH$_3$, —C$_6$H$_5$, —SO$_3$H, —SO$_3$Na, —SO$_2$(CH$_3$), —SO$_2$(CH$_2$CH$_3$), —SO$_2$(OCH$_3$), —SO$_2$(OCH$_2$CH$_3$), —SO$_2$N(CH$_3$)$_2$, —SO$_2$N(CH$_3$)(CH$_2$CH$_3$) and —SO$_2$N(CH$_2$CH$_3$)$_2$.

16. A compound according to claim 15, wherein R$_1$ is Br, Cl, F, —CH$_3$ or —OCH$_3$.

17. A compound according to claim 16, wherein R$_1$ is Br or F.

18. A compound according to claim 17, wherein p is 1 and the Br is in the para-position to the amino group.

19. A compound according to claim 17, wherein p is 1 and the F is in the para-position to the amino group.

20. A composition comprising a compound of Formula (I) as defined in claim 1 or a salt thereof, and a carrier.

21. A method of treating or preventing a bacterial infection in a subject, the method comprising administering to the subject an effective amount of a compound of Formula (I) as defined in claim 1 or a pharmaceutically acceptable salt thereof, wherein the bacterial infection is caused by *S. aureus* or *E. coli*.

22. A method of treating a surface to prevent, reduce or inhibit biofilm formation on the surface, the method comprising applying to the surface, or contacting the surface with, an effective amount of a compound of Formula (I) as defined in claim 1 or a salt thereof.

23. A method of preventing, reducing or inhibiting biofilm formation on a surface, the method comprising applying to the surface, or contacting the surface with, an effective amount of a compound of Formula (I) as defined in claim 1 or a salt thereof, or exposing a biofilm, or a microorganism capable of forming a biofilm, to a compound of Formula (I) as defined in claim 1 or a salt thereof.

* * * * *